United States Patent [19]

Liebenberg et al.

[11] Patent Number: 5,609,874
[45] Date of Patent: Mar. 11, 1997

[54] METHOD OF TREATING VIRAL INFECTIONS

[75] Inventors: Roelof W. Liebenberg, Pierneff Park; Petrus B. Kruger, Camps Bay; Patrick J. D. Bouic, Rondebosch East; Carl F. De Vos Albrecht, Amanda Glen, all of South Africa

[73] Assignee: Virostat (NA) NVQ, Kralendijk, Netherlands Antilles

[21] Appl. No.: 398,865

[22] Filed: Mar. 6, 1995

Related U.S. Application Data

[63] Continuation-in-part of Ser. No. 116,665, Sep. 3, 1993, abandoned.

[30] Foreign Application Priority Data

Sep. 7, 1992 [ZA] South Africa ............................ 92/6775
Jun. 4, 1993 [ZA] South Africa ............................ 93/3949

[51] Int. Cl.$^6$ ........................... A61K 35/78; A61K 31/70; A61K 31/095; A61K 31/045
[52] U.S. Cl. ......................... 424/195.1; 514/25; 514/706; 514/738; 514/986; 514/934
[58] Field of Search .......................... 424/195.1; 536/4.1, 536/12.8; 514/25, 738, 706, 934, 886

[56] References Cited

FOREIGN PATENT DOCUMENTS

| 92226 | 4/1983 | European Pat. Off. ....... A61K 35/78 |
| 86/4482 | 2/1987 | South Africa . |

OTHER PUBLICATIONS

Marini Bettolo, et al., Tetrahedron, 1982, 38(11):1683–1687.
Betto, et al., J. Chrom. 1992, 594(1):131–135.

*Primary Examiner*—John W. Rollins
*Attorney, Agent, or Firm*—Curtis, Morris & Safford PC

[57] ABSTRACT

This invention relates to a method and means for the treatment of a viral infection and for reducing the rate of decrease in CD4 lymphocyte counts in a subject having a viral infection. It relates, in particular, to a use of an extract of corms of the family Hypoxidaceae in the preparation of a medicament for the treatment of a viral infection; to the use of the said extract in the preparation of a medicament for reducing the rate of decrease of CD4 lymphocyte counts in a subject with a viral infection; to a method of treating a viral infection, to a method of reducing the rate of decrease in CD4 lymphocyte counts in a subject having a viral infection; to a medicament for the treatment of a viral infection, and to a medicament for reducing the rate of CD4 lymphocyte counts in a subject having a viral infection.

25 Claims, 49 Drawing Sheets

METHOD OF TREATING VIRAL INFECTIONS

CROSS REFERENCES TO RELATED APPLICATION

This application is a Continuation-in-Part of U.S. Ser. No. 08/116,665, now abandoned, incorporated herein by reference. Reference is made to concurrently filed appln. Ser. No. 08/398,851 as a CIP of U.S. Ser. No. 08/116,665 incorporated herein by reference.

FIELD OF THE INVENTION

This invention relates to a method and means for the treatment of a viral infection and for reducing the rate of decrease in CD4 lymphocyte counts in a subject having a viral infection. It relates, in particular, to a use of an extract of corms of the family Hypoxidaceae in the preparation of a medicament for the treatment of a viral infection; to the use of the said extract in the preparation of a medicament for reducing the rate of decrease of CD4 lymphocyte counts in a subject with a viral infection; to a method of treating a viral infection, to a method of reducing the rate of decrease in CD4 lymphocyte counts in a subject having a viral infection; to a medicament for the treatment of a viral infection, and to a medicament for reducing the rate of CD4 lymphocyte counts in a subject having a viral infection.

More particularly, the invention relates to said use, to said method and to said medicament for the treatment of human immunodeficiency viral (HIV) infection respiratory syncytial viral (RSV) infection and cytomegalo viral (CMV) infection and for reducing the rate of decrease in CD4 lymphocyte counts in a subject having human immunodeficiency viral (HIV) infection, respiratory syncytial viral (RSV) infection and cytomegalo viral (CMV) infection.

SUMMARY OF THE INVENTION

According to one aspect of the invention, there is provided the use of an extract from at least one plant species which is a member of the plant family Hypoxidaceae in the preparation of a medicament for the treatment of a viral (eg HIV) infection.

The invention extends to the use of said extract in the preparation of a medicament for reducing the rate of decrease of CD4 lymphocyte counts in a subject having a viral (eg HIV) infection.

The extract may be from at least one plant species which is a member of a plant genus selected from the plant genera Hypoxis, Spiloxene, Curculigo and Campynema.

More particularly, the extract may be from at least one plant species selected from the group consisting of *Hypoxis nitida, H. obtusa, H. rigidula, H. villosa, H. interjecta, H. multeceps, H. nyasica, H. rooperi, H. accuminata, H. latifolia, Spiloxene schlechteri* and hybrids thereof and, more particularly, from the group consisting of *H. rooperi, H. accuminata* and *H. latifolea*. The extract may be a dried extract.

Compounds of general formula (1)

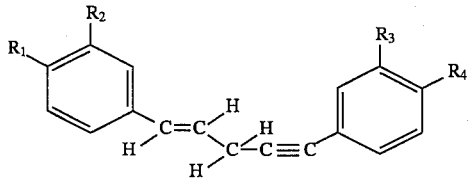

in which:
$R_1$, $R_2$, $R_3$ and $R_4$ are the same or different and are selected from —H, —OH, A, B, C and D in which:

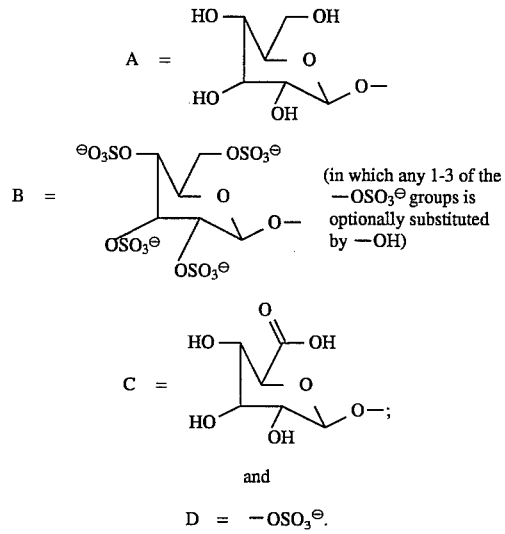

and $D = -OSO_3^\ominus$.

and, in particular, in which $R_2$ and $R_3$ are selected from —OH, —H and D in which $R_1$ and $R_4$ are selected from —OH, A, B, C and D (as set out in Table 1 below) are Found in the extract of corms of Hypoxis species or are metabolites of said compounds. In particular compounds V–VIII of Table 1 are found in the said extract whilst compounds I–IV and IX–XXVIII are metabolites thereof. Metabolites I–IV are produced in the intestine of the human body, and metabolites IX–XXVIII are produced by phase II biotransformation in the human body. By a phase II biotransformation is meant a biosynthetic reaction whereby a substituent is added to a precursor molecule, which generally renders the precursor molecule more water-soluble and/or biologically less reactive.

TABLE 1

| N° | $R_1$ | $R_2$ | $R_3$ | $R_4$ |
|---|---|---|---|---|
| I | OH | OH | OH | OH |
| II | OH | H | H | OH |
| III | OH | OH | H | OH |
| IV | OH | H | OH | OH |
| V | A | OH | OH | A |
| VI | A | H | H | A |
| VII | A | OH | H | A |
| VIII | A | H | OH | A |
| IX | B | OH | OH | B |
| X | B | H | H | B |
| XI | B | OH | H | B |
| XII | B | H | OH | B |
| XIII | C | OH | OH | C |
| XIV | C | H | H | C |
| XV | C | OH | H | C |
| XVI | C | H | OH | C |
| XVII | D | OH | OH | D |
| XVIII | D | H | H | D |

TABLE 1-continued

| N° | R₁ | R₂ | R₃ | R₄ |
|---|---|---|---|---|
| XIX | D | OH | H | D |
| XX | D | H | OH | D |
| XXI | C | OH | OH | D |
| XXII | C | H | H | D |
| XXIII | C | OH | H | D |
| XXIV | C | H | OH | D |
| XXV | D | OH | OH | C |
| XXVI | D | H | H | C |
| XXVII | D | OH | H | C |
| XXVIII | D | H | OH | C |

Any of the hydroxyl groups in compounds IX, XI and XII in Table 1 at the $R_2$ and $R_3$ positions can be substituted by D.

The present invention makes possible a method of treating a viral infection, which comprises administering to a subject an active therapeutic agent which comprises an extract from a plant species which is a member of the plant family Hypoxidaceae. The invention also makes possible a method of reducing the rate of decrease in CD4 lymphocyte counts in a subject having a viral infection, which comprises administering to the subject an active therapeutic agent which comprises an extract from a plant species which is a member of the plant family Hypoxidaceae. The viral infection may be human immunodeficiency viral infection.

The compound E-1,5-bis (3'-hydroxy-4'-O-β-D-glucopyranosylphenyl) pent-4-en-1-yne (also known as hypoxoside) is the compound V in accordance with formula (1) in which $R_2$ and $R_3$ are —OH and $R_1$ and $R_4$ are A. The abovementioned extracts from plants of the family Hypoxidaceae contain one or more of compounds V–VIII, particularly V–VII. The isolation of hypoxoside and related 1,5-disubstituted pent-4-en-1-yne compounds from plants of the family Hypoxidaceae is described in Marini-Bettolo et al:.Tetrahedron, 1982, 38, 1683–1687, and synthesis thereof is described in South African Patent No. 86/4482.

As indicated above, it should be noted that, optionally, any 1–3 of the sulphate groups in B can be substituted by —OH; any of the hydroxyl groups in compounds IX, XI and XII can be substituted by D.

The plant extract, may be administered orally, or parenterally.

The invention extends to a medicament for the treatment of a viral (eg HIV) infection, which comprises, as an active therapeutic agent, an extract as hereinbefore described, and a physiologically acceptable carrier.

The invention extends, further, to a medicament for reducing the rate of decrease in CD4 lymphocyte counts in a subject having a viral (eg HIV) infection which comprises, as an active therapeutic agent, an extract as hereinbefore described, and a physiologically acceptable carrier.

The medicament may be in a dosage form selected from tablets, capsules, powders and liquids containing the active therapeutic agent (ie the extract), the tablets, powders and capsules each containing 20–1000 mg of the active therapeutic agent and the liquids containing 4–200 mg/ml of the active therapeutic agent, eg 40 mg/ml.

The invention thus extends to a method of treating a viral (eg HIV) infection which method comprises administering to a subject an active therapeutic agent comprising an extract from a plant species which is a member of the plant family Hypoxidaceae as hereinbefore described.

The invention extends, further, to a method of reducing the rate of decrease in CD4 lymphocyte counts in a subject having a viral (eg HIV) infection, which method comprises administering to the subject an active therapeutic agent comprising an extract from a plant species which is a member of the plant family Hypoxidaceae as hereinbefore described.

The therapeutic agent for treating a viral infection or for reducing the rate of reduction in CD4 lymphocyte counts may comprise said extract and, in addition, another compound of general formula (1) eg any one of compounds I–XXVIII.

In the case of parenteral administration, the plant extract may be administered intravenously, dissolved in a suitable aqueous solution, such as a saline solution. Intravenous administration may be continuous or intermittent, and may be such as to obtain, on average, blood plasma levels of the compounds I–XXVIII and/or metabolites thereof, such as phase II biotransformation products thereof, of 0.1–400 µg/ml, such as 25–200 µg/ml, and preferably 50–150 µg/ml, e.g. 100 µg/ml.

It is expected that, for intravenous administration, the extract will be administered in sterile solution at a concentration of 1–200 mg/ml; typically 50–100 mg/ml, at a rate to achieve steady state plasma levels as described above of said compounds I–XXVIII of up to 400 µg/ml blood plasma.

In the case of oral administration, the plant extract may be in the form of a tablet or in the form of a powder or in the form of a solution, and may be contained in a capsule. The solution may be an aqueous solution of the plant extract. Similarly, the tablet, powder or capsule may comprise the plant extract. Each tablet or capsule may contain 20–1000 mg of the extract.

Trials with human volunteers with untreatable large cell cancer of the lung have been carried out using dried methanolic extract from plant species of Hypoxidaceae. Such dried methanolic extract is described hereinafter in Example 2. These trials revealed that oral administration of the dried methanolic plant extract at rates up to 3200 mg/day, to provide blood plasma levels in subjects of the order of 200 µg/ml, are well tolerated. The only side-effects were limited to a degree of nausea, vomiting and diarrhoea in a small proportion (3 out of 25) of subjects. Further trials with human volunteers showed that oral administration of 1200–3200 mg of extracts of H. rooperi and H. accuminata daily for up to five years to maintain a steady state metabolite blood level of about 100 µg/ml produced no toxic effects, in clinical examinations, clinical chemistry or haematological analysis, that could be ascribed to the ingestion of the extract. Clinical trials which demonstrate non-toxicity are described in Example 15.

In further trials the dried methanolic extract was administered intravenously, after dissolving in a saline solution, to sheep at a dosage rate of 200 mg hypoxoside/kg/day, for at least 30 days and up to 60 days, with no significant drug-related effects other than a reduced mass gain and some discolouration of connective tissue at the site of administration. The method accordingly extends to the parenteral and in particular intravenous administration of the plant extract particularly the high pressure liquid chromatograph purified fraction containing compounds V–VIII from the methanolic plant extract dissolved in an aqueous solution, preferably a saline solution. Furthermore, as compounds IX–XXVIII have been found to be present at combined or total concentration levels in plasma of tip to 400 µg/ml plasma after oral ingestion by humans of the extract, or of a high-pressure liquid chromatographed purified fraction of the extract, containing compounds V–VII, compounds IX–XXVIII are particularly suitable for direct intravenous infusion, dissolved in saline solutions.

In trials it has been found, surprisingly, that the plant extract exhibits anti-HIV activity in vitro. Furthermore, surprisingly, it has also been found that the compounds V–VIII of the plant extract in pure form or as part of the plant extract, when biotransformed (phase II biotransformation) show anti-HIV activities both in vitro and in vivo. Said compounds and plant extract are effective in the reduction of the rate of decrease in CD4 lymphocyte counts in a subject having HIV infection. The Applicant has, for example, found that the long term oral administration of an extract of corms of the family Hypoxidaceae (particularly, but not exclusively, *H. rooperi, H. accumunata* and *H. latifolia*) reduces the rate of decrease in CD4 lymphocyte counts in subjects having HIV infection. Hypoxosides have been identified as one of the components of the extract which contribute to the observed effect.

The utility of compounds IX–XXVIII is particularly unexpected and surprising, because phase II (hepatic and/or extrahepatic) biotransformation of compounds usually leads to their biological deactivation. The anti-pathogenic or antiviral effect of these metabolites is thus completely unexpected. In these trials the treated subjects exhibited a mean decrease in p24 HIV core protein levels, a decrease in the rate of decrease of CD4 lymphocyte counts and a mean increase in the levels of certain lymphocyte subsets, when compared with the mean values characteristic of HIV infections for untreated subjects.

BRIEF DESCRIPTION OF THE DRAWINGS

The invention will now be described, by way of example, with reference to tests which have been conducted to demonstrate activity, in vitro, against HIV, with reference to clinical trials, with reference to Examples for the preparation of novel compounds IX–XXVIII, and with reference to the accompanying Figures, in which.

| Compound | Retention Time (minutes) |
|---|---|
| I | 12.18 |
| II | 14.84 |
| (III + IV) | 13.55 |
| V | 8.25 |
| VI | 8.76 |
| (VII + VIII) | 8.50; |

Figure 1:
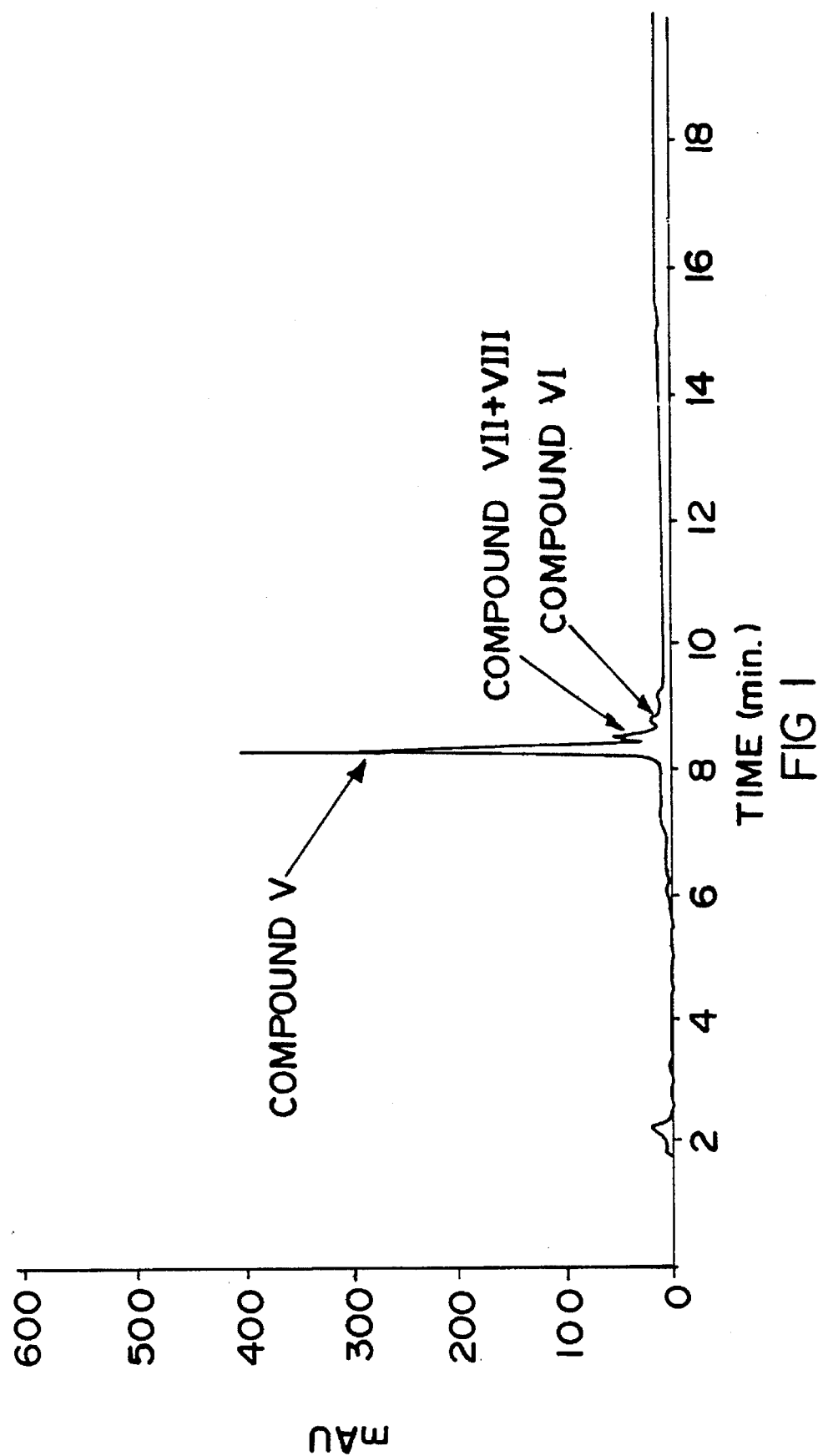
FIG. 1 shows a chromatogram plotting mAU (milliabsorbence units) against time (minutes) of a methanolic extract of compounds V–VIII from corms of *Hypoxis rooperi*, to illustrate the relative amounts of compound V, compound VI and compounds (VII+VIII) in the extract, employing a signal wavelength of 260 nm at a bandwidth of 20 nm, with a reference wavelength of 550 nm at a bandwidth of 50 nm.
Figure 3:
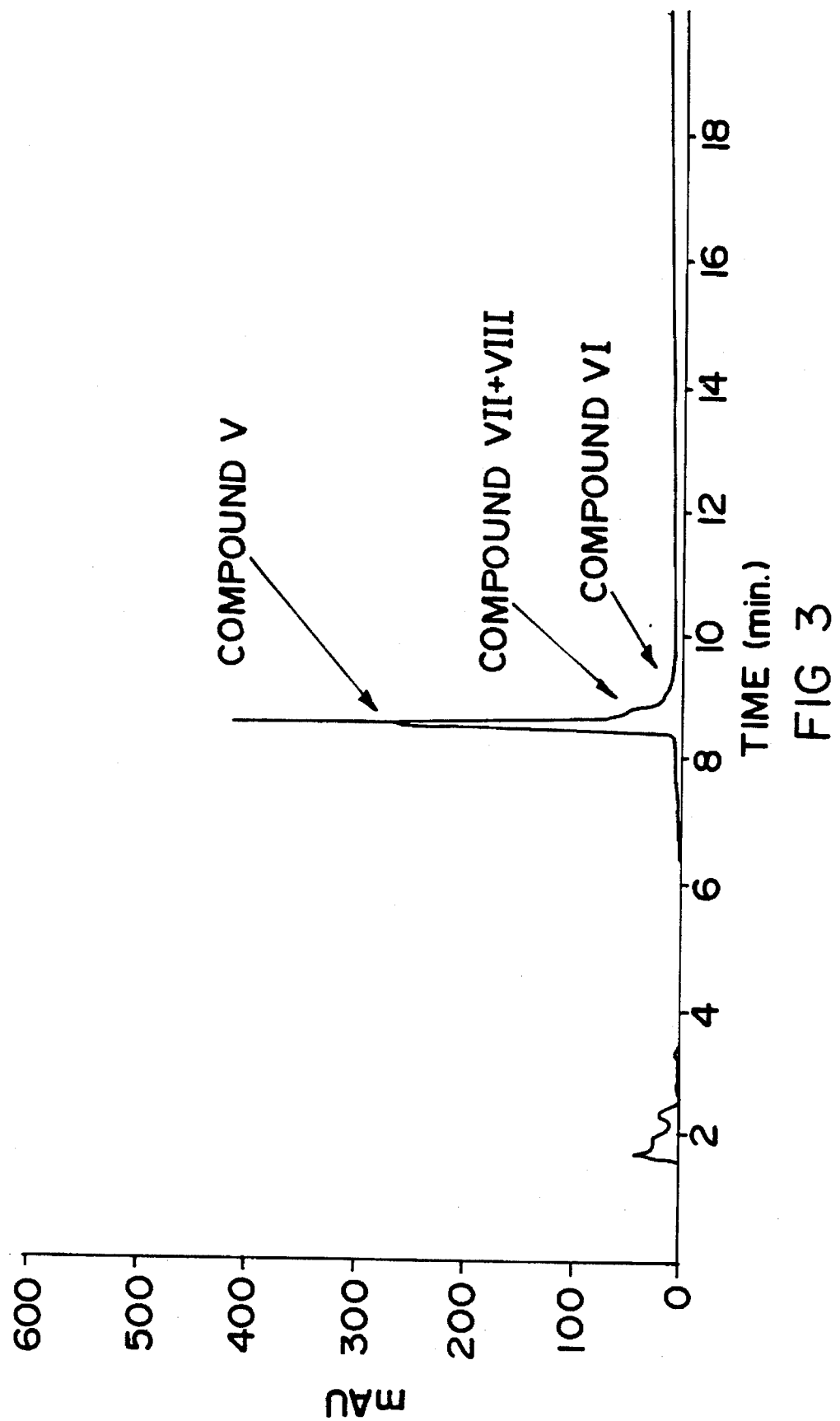

FIG. 3 shows a chromatogram, similar to FIG. 1, of compounds V–VIII as purified by HPLC from a methanolic extract of *H. rooperi*, retention times being:

| Compound | Retention Times (minutes) |
|---|---|
| V | 8.28 |
| VI | 8.79 |
| (VII + VIII) | 8.54; |

Figure 4:
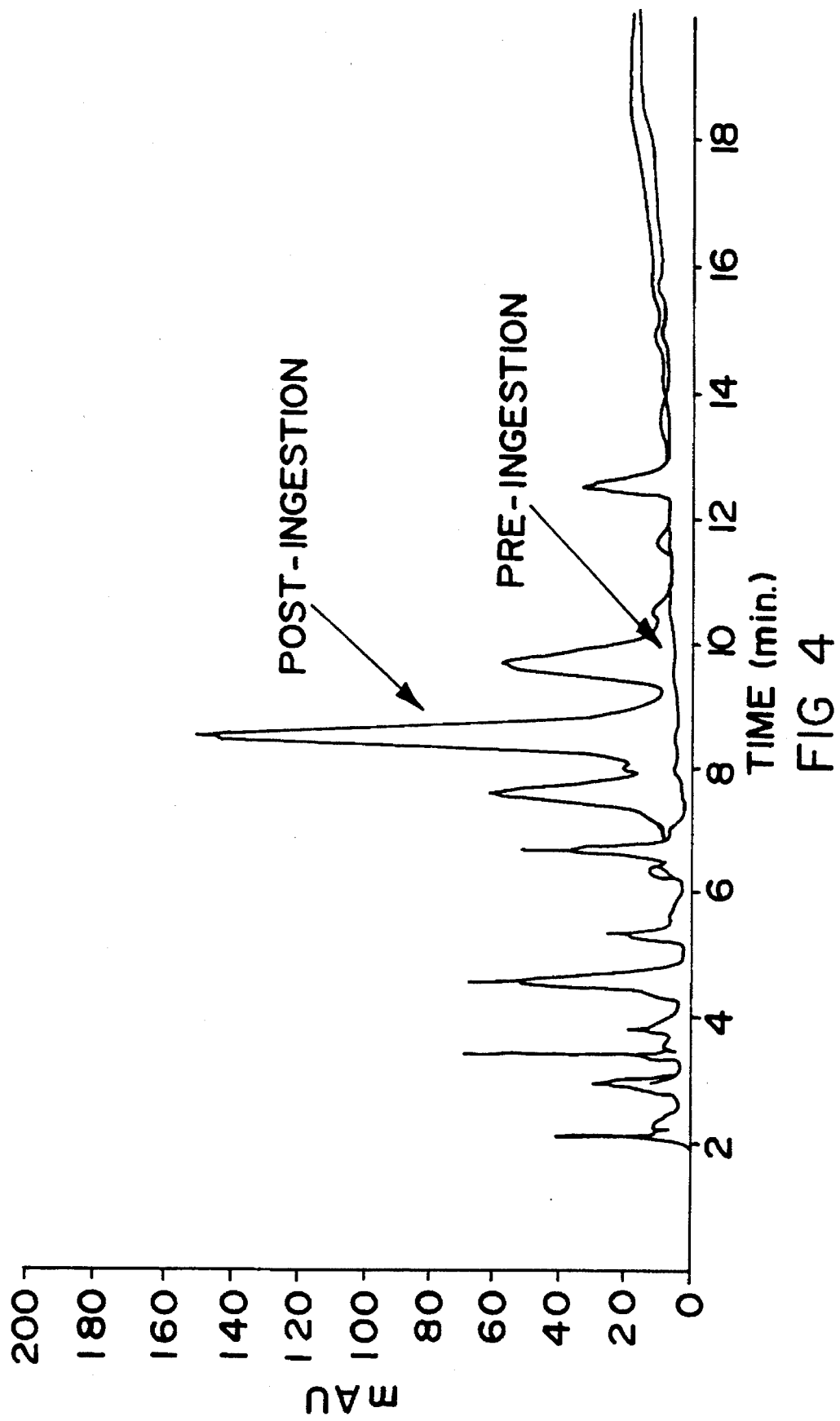
Figure 5:
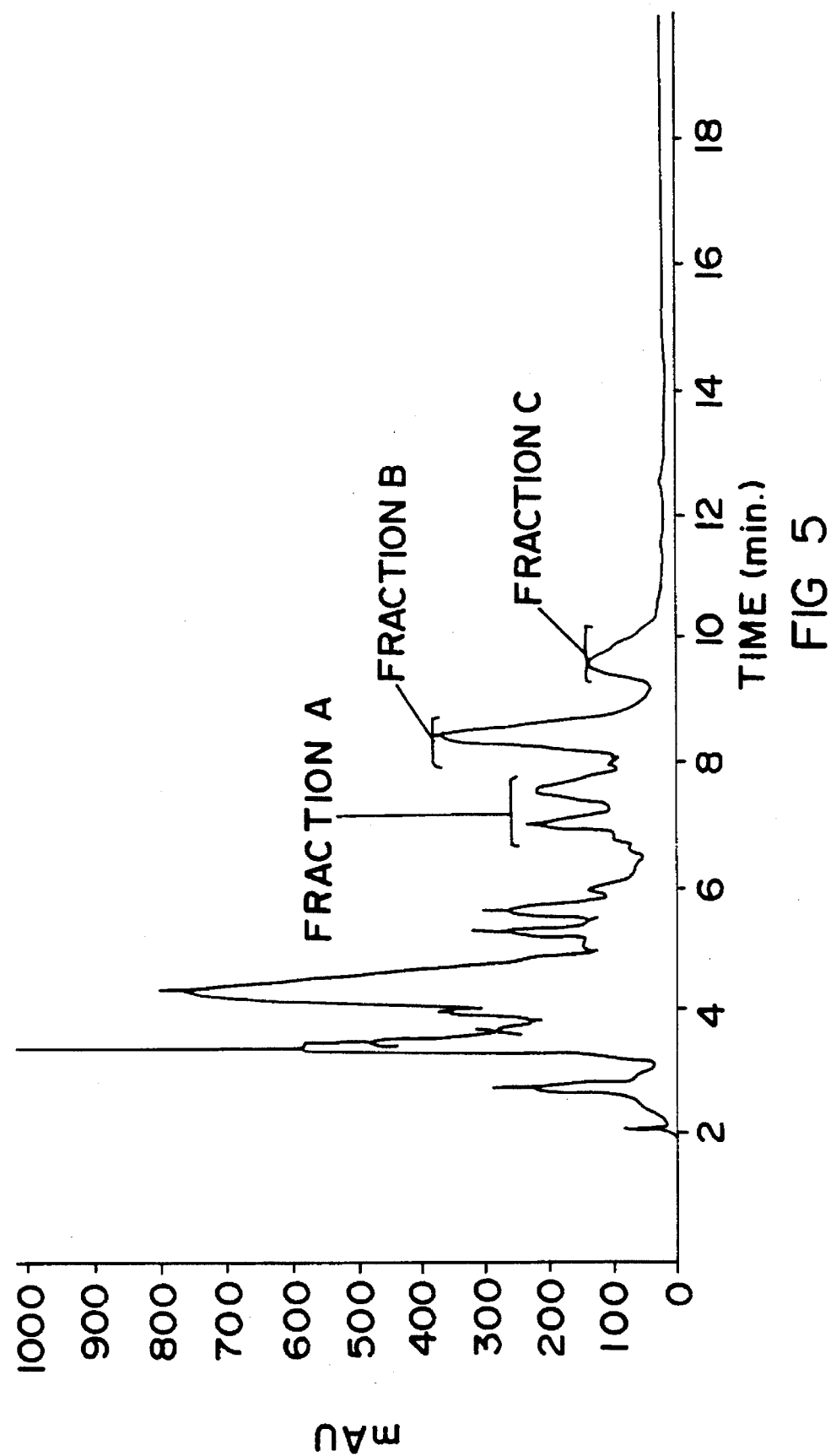
Figure 6:
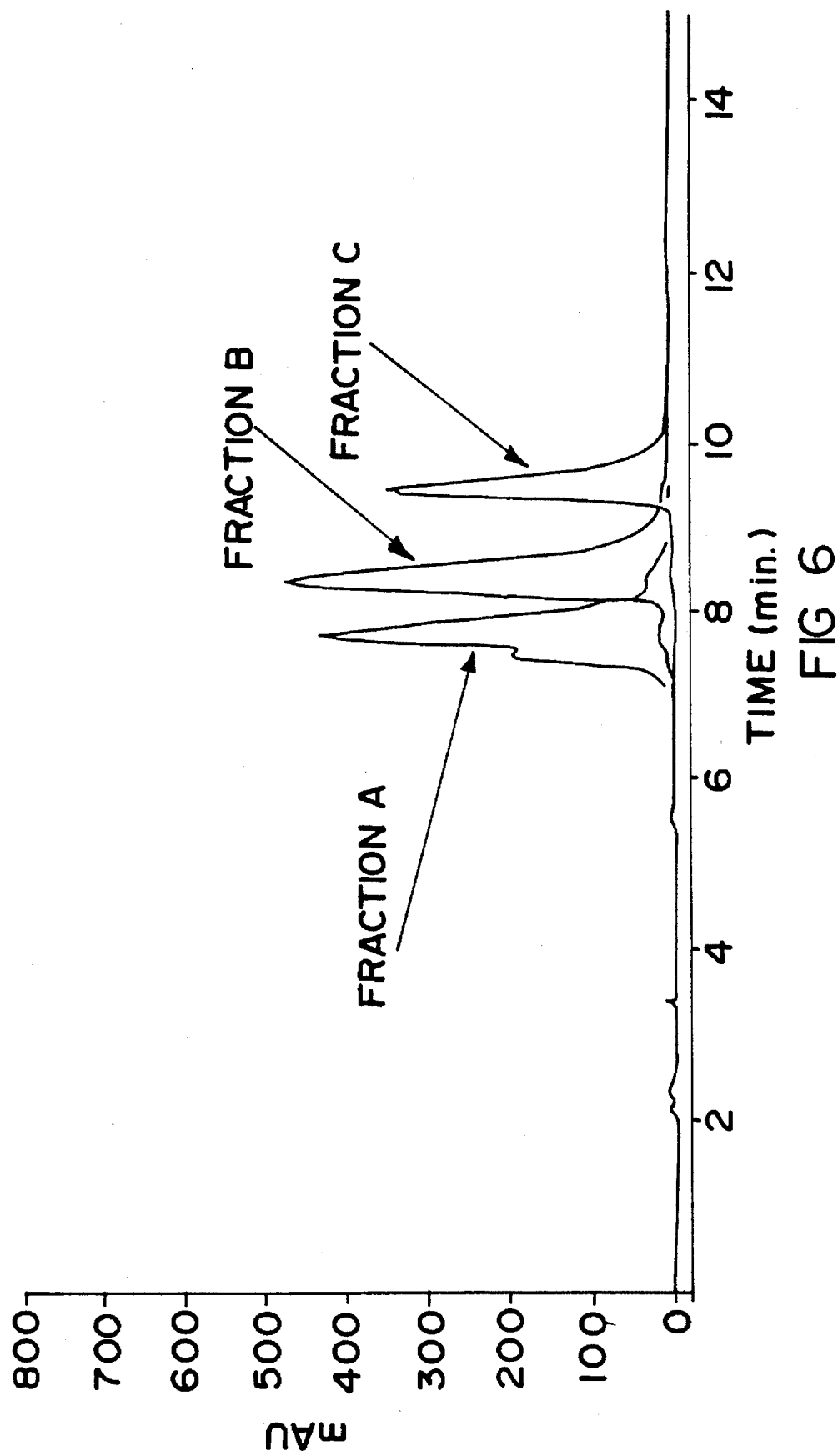

FIG. 4 shows a chromatogram, similar to FIG. 1, of human serum analysed before ingestion of 1 g of the purified compounds V–VIII whose chromatogram is shown in FIG. 3, and, superimposed thereon, a chromatogram of serum from the same subject 90 minutes after ingestion of said compounds, the metabolites of compounds V–VIII comprising the three major peaks of the post-ingestion chromatogram, being analogous to the urinary fractions A, B and C respectively of FIGS. 5 and 6 hereunder;

FIG. 5 shows a chromatogram, similar to FIG. 1, of human urine three hours after the ingestion of the purified compounds V–VIII whose chromatogram is shown in FIG. 3 and which illustrates the three urinary fractions A, B and C which are illustrated also in FIG. 6;

FIG. 6 shows three chromatograms, similar to FIG. 1, superimposed to illustrate three tractions, namely fractions A, B and C, of purified metabolites preperatively isolated by HPLC from the urine whose chromatogram is shown in FIG. 5, their retention times being:

| Fraction | Retention Time (minutes) |
|---|---|
| A | 7.19 |
| B | 7.90 |
| C | 9.03; |

Figure 7:
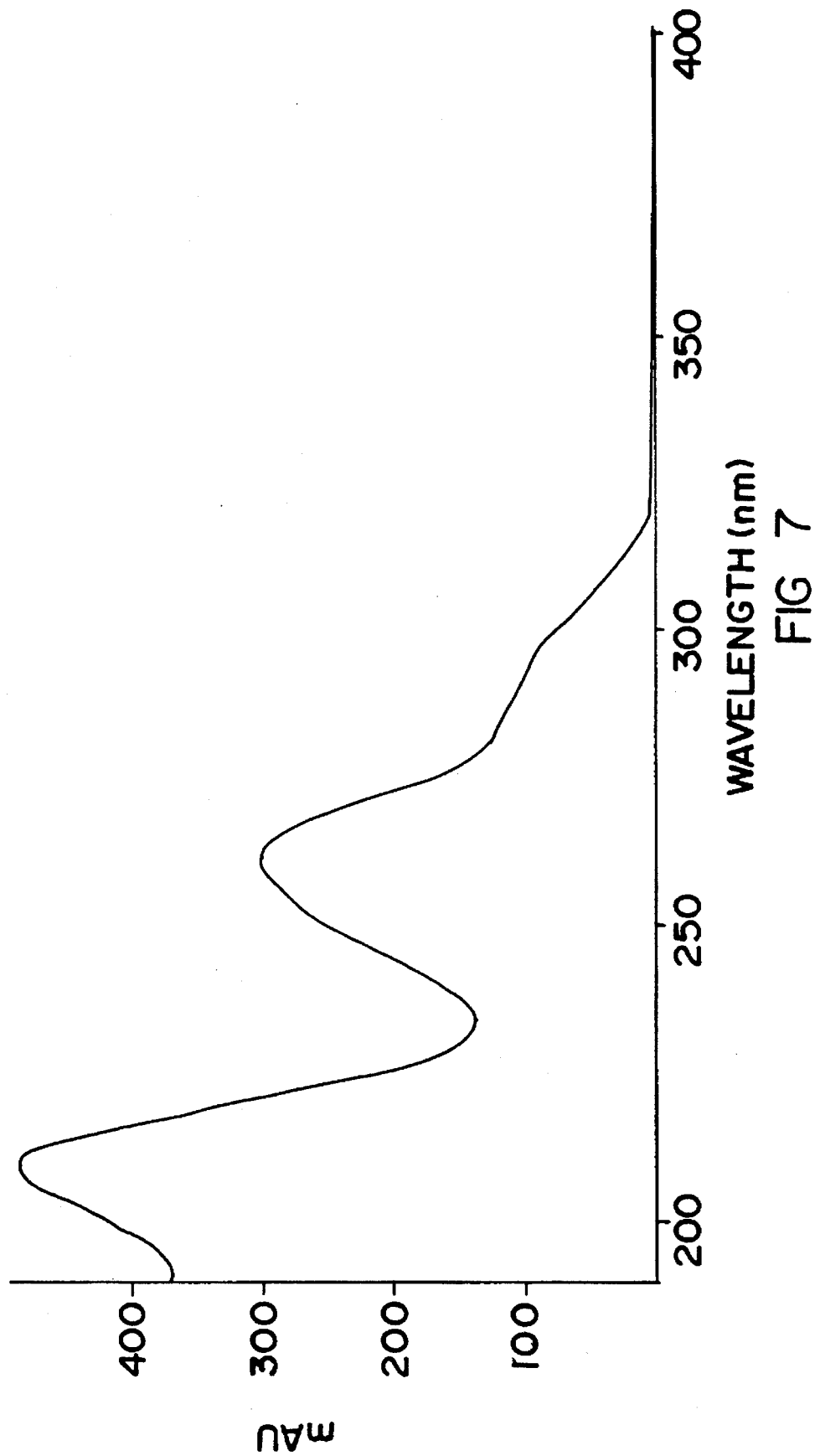
Figure 8:
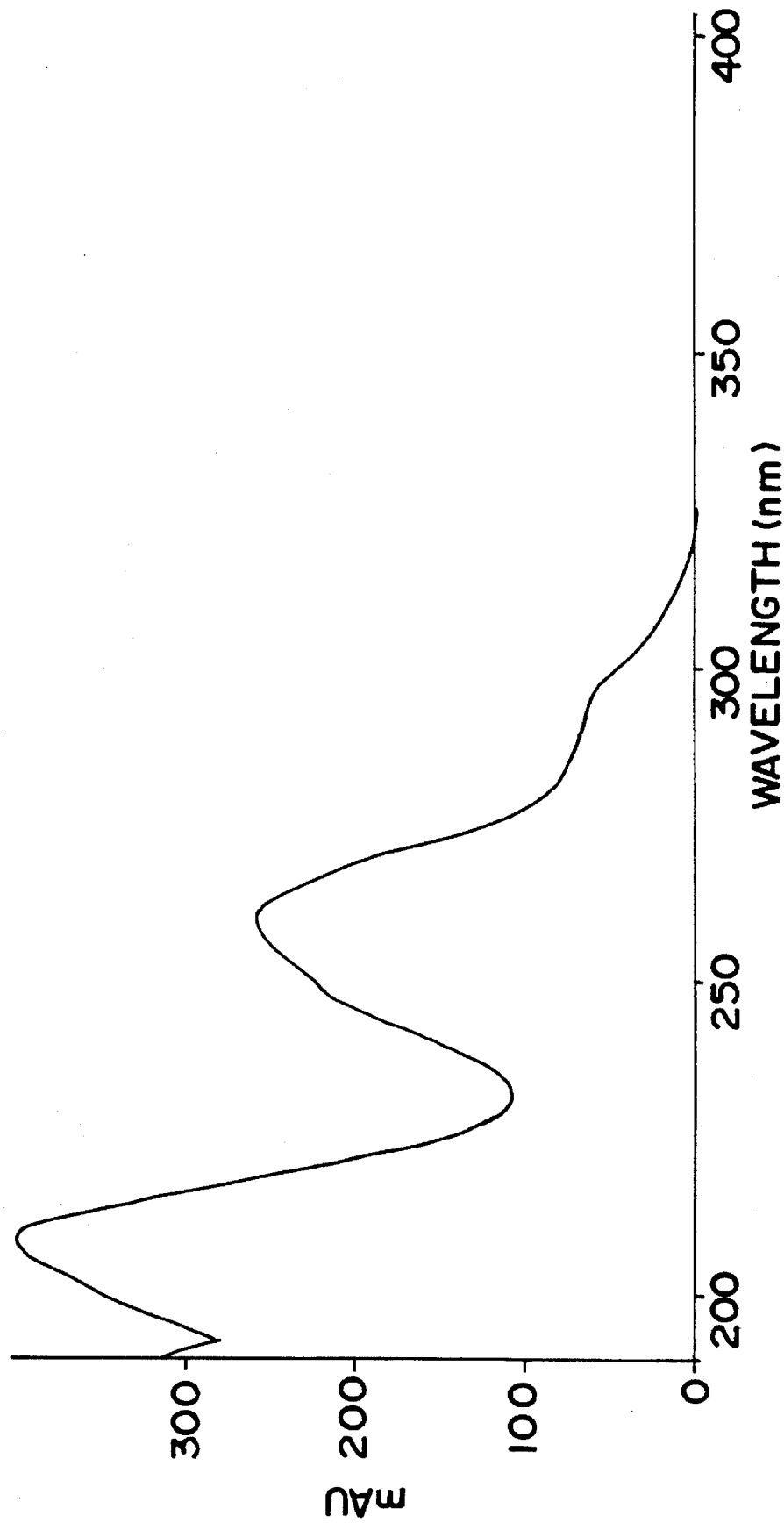
Figure 9:
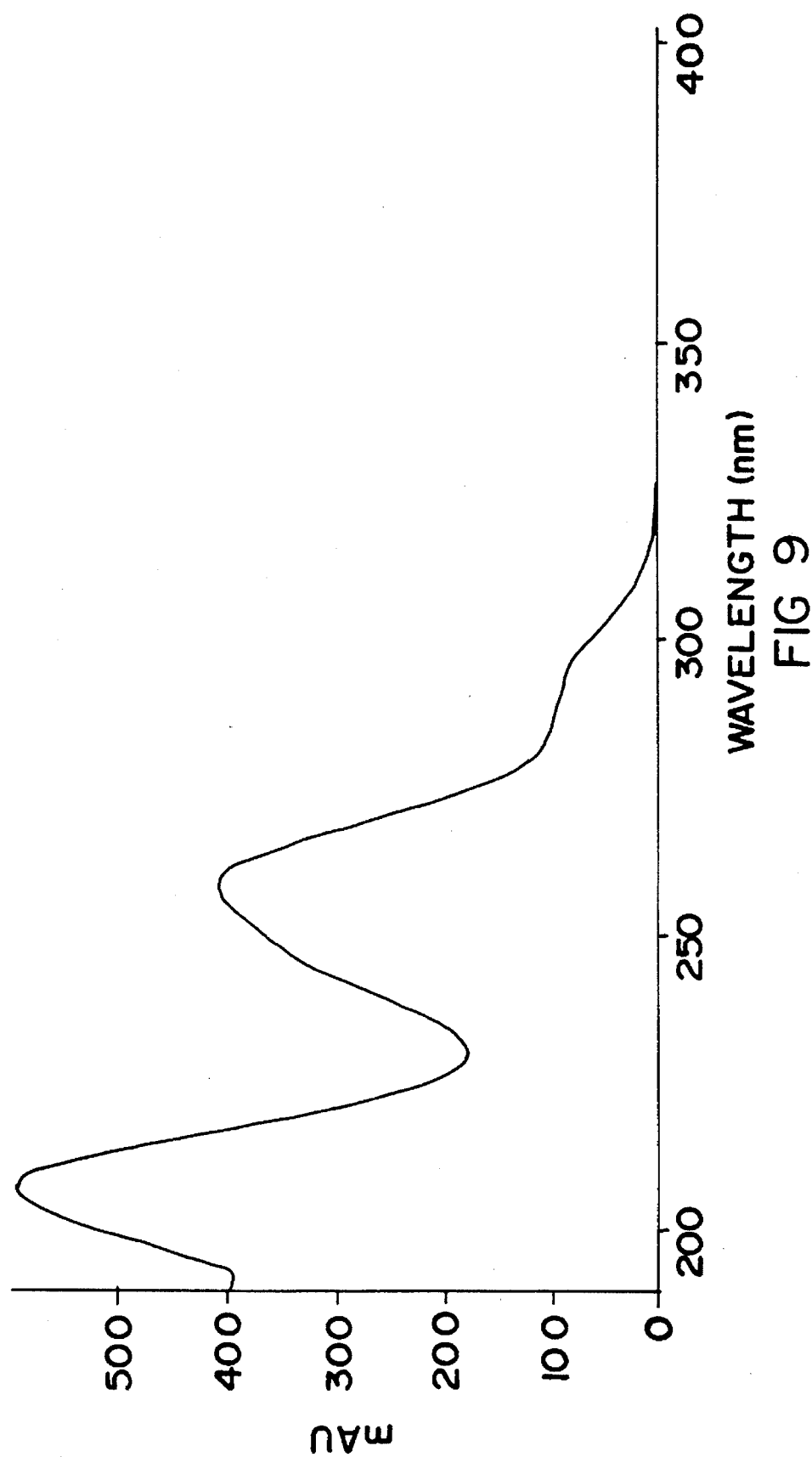
Figure 10:
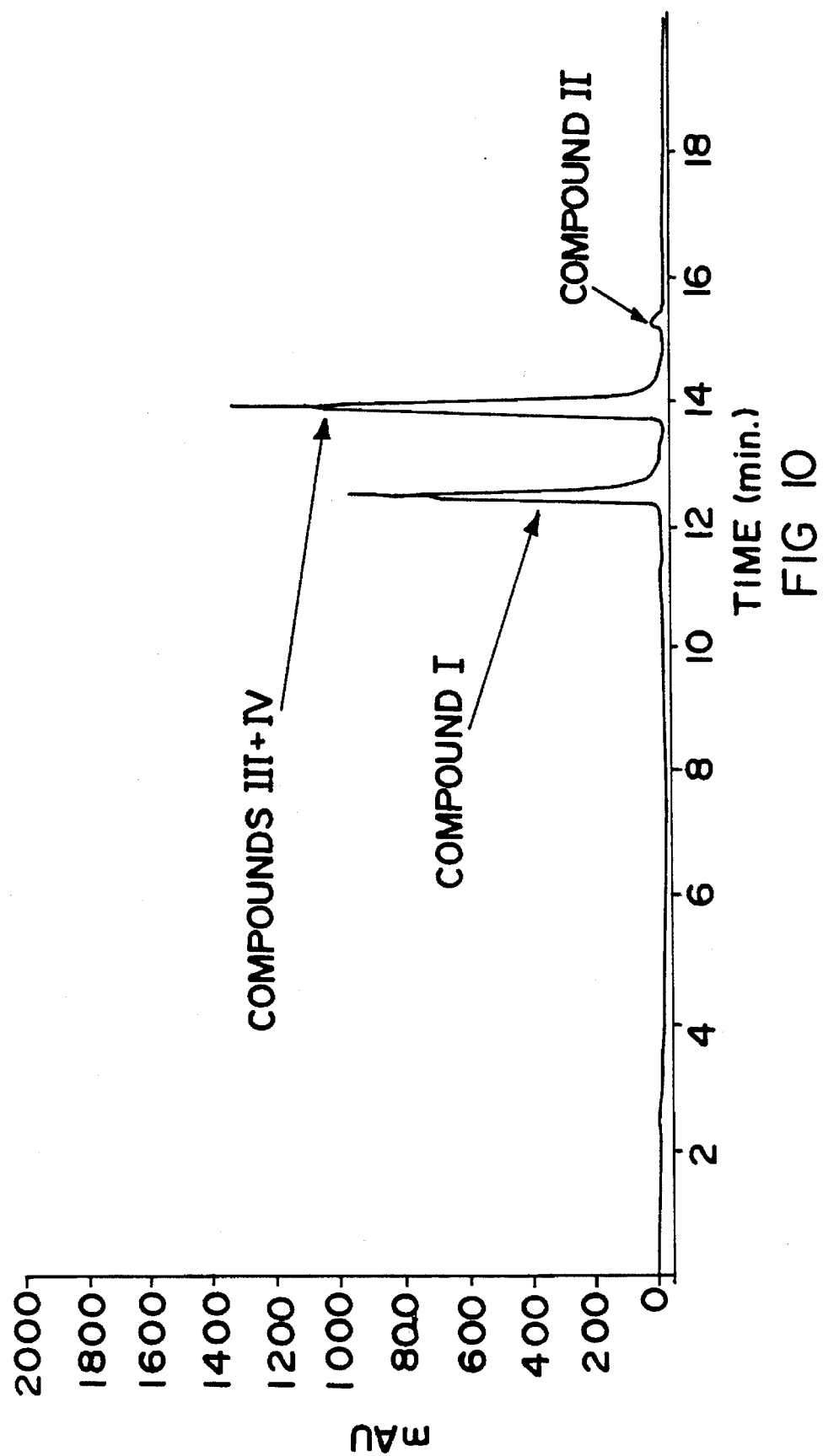

FIG. 7 shows a diode array detector ultraviolet (UV) absorption spectrogram illustrating the absorption spectrum of purified urine metabolite fraction A of FIG. 6, being a plot of mAU against wavelength (nm), the spectrogram having absorption wavelength maxima at 206.5–210.5 nm and 258.5–262.5 nm respectively, and an absorption wavelength minimum at 230.5–234.5 nm;

FIG. 8 shows a spectrogram, similar to FIG. 7, for the absorption spectrum of fraction B of FIG. 6, the spectrogram having absorption wavelength maxima at 206.5–210.5 nm and 258.5–262.5 nm respectively, and an absorption wavelength minimum at 228.5–232.5 nm;

FIG. 9 shows a spectrogram, similar to FIG. 7, of the absorption spectrum of fraction C of FIG. 6, the absorption spectrum having absorption wavelength maxima at 204.5–208.5 nm and 256.5–260.5 nm respectively, and an absorption wavelength minimum at 228.5–232.5 nm;

FIG. 10 shows an HPLC chromatogram, similar to FIG. 1, of the aconjugates of purified urine fraction A as derived by the hydrolysis of fraction A with β-glucuronidase and aryl-sulphatase at pH 5.5, retention times being:

| Compound | Retention Time (minutes) |
|---|---|
| I | 12.35 |
| II | 14.91 |
| (III + IV) | 13.58 | correspondence being found between these retention data and those respectively of compound I, compound II and compounds (III+IV), as derived by the action of β-glucosidase on the ehtanolic extract of *H. latifolia* as shown in FIG.

Figure 11:
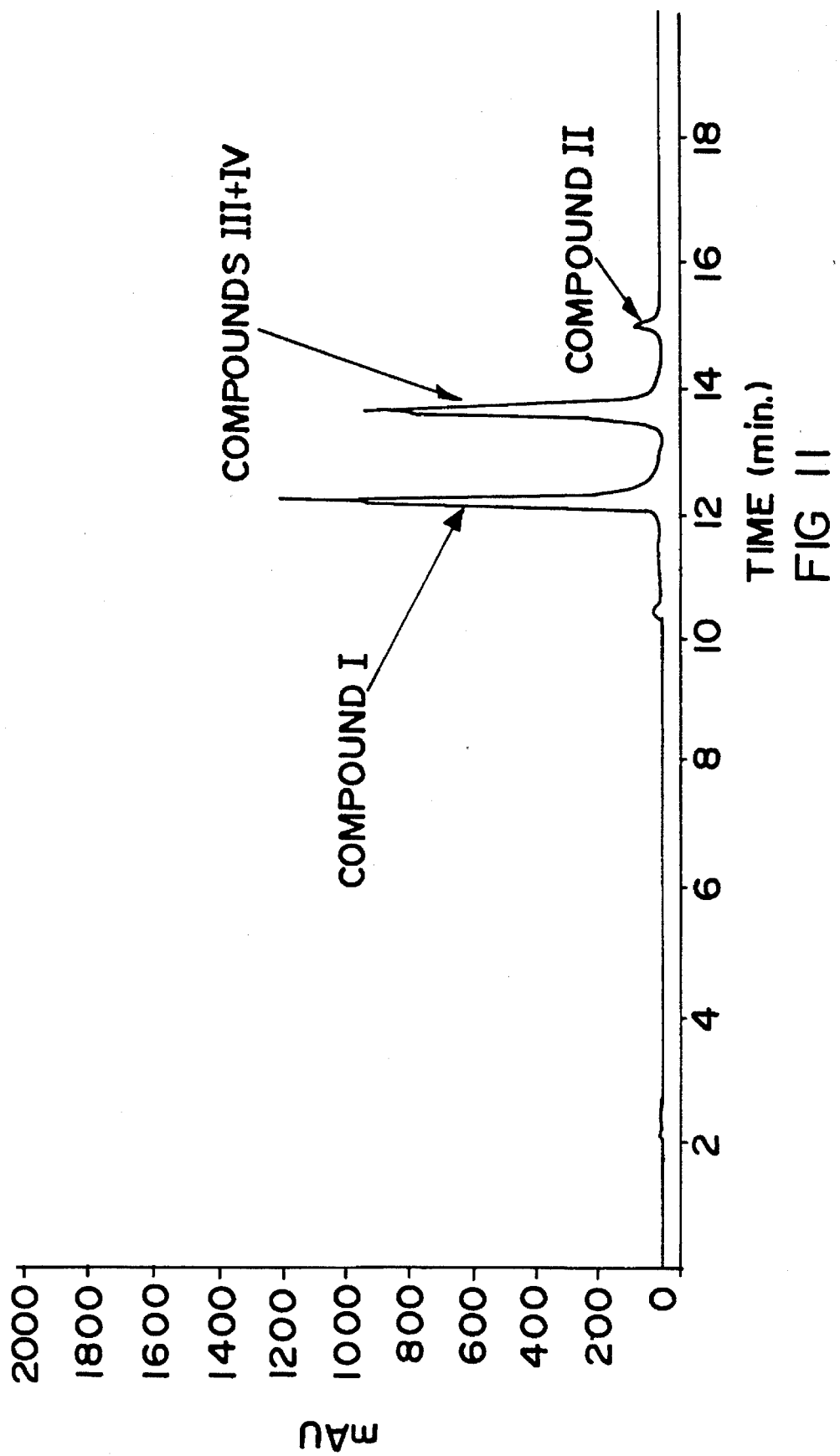
Figure 12:
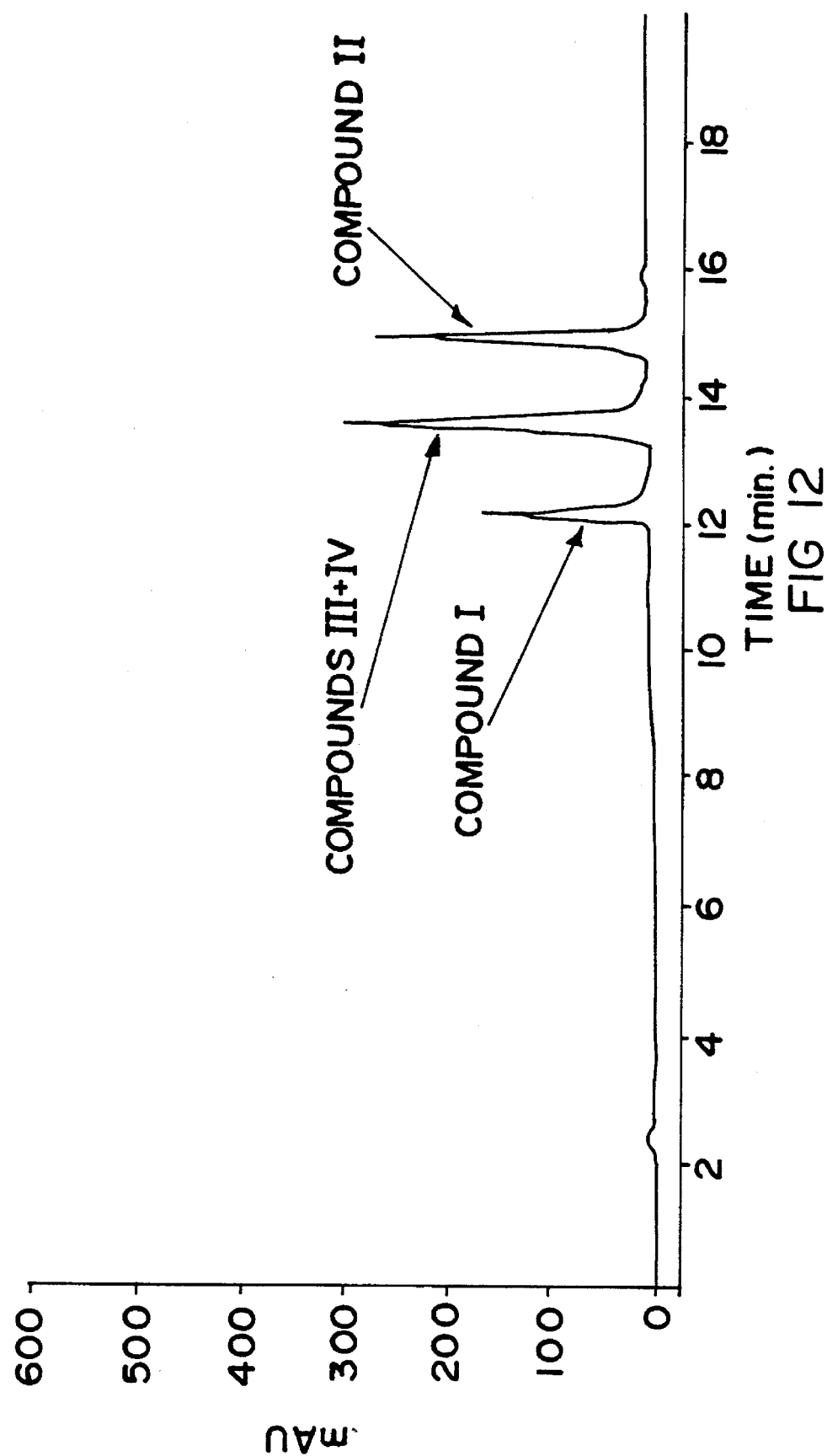
Figure 13:
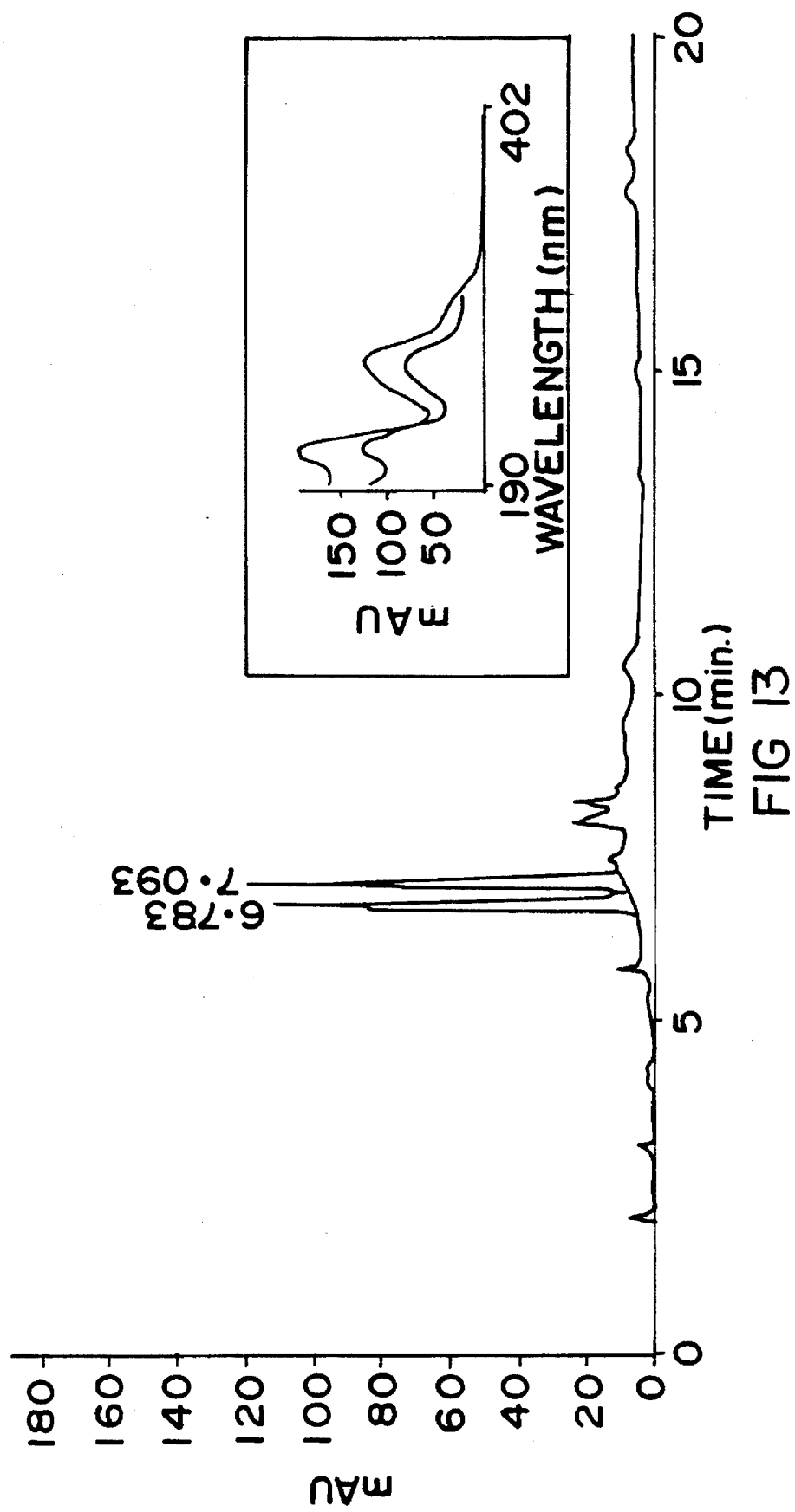
Figure 14:
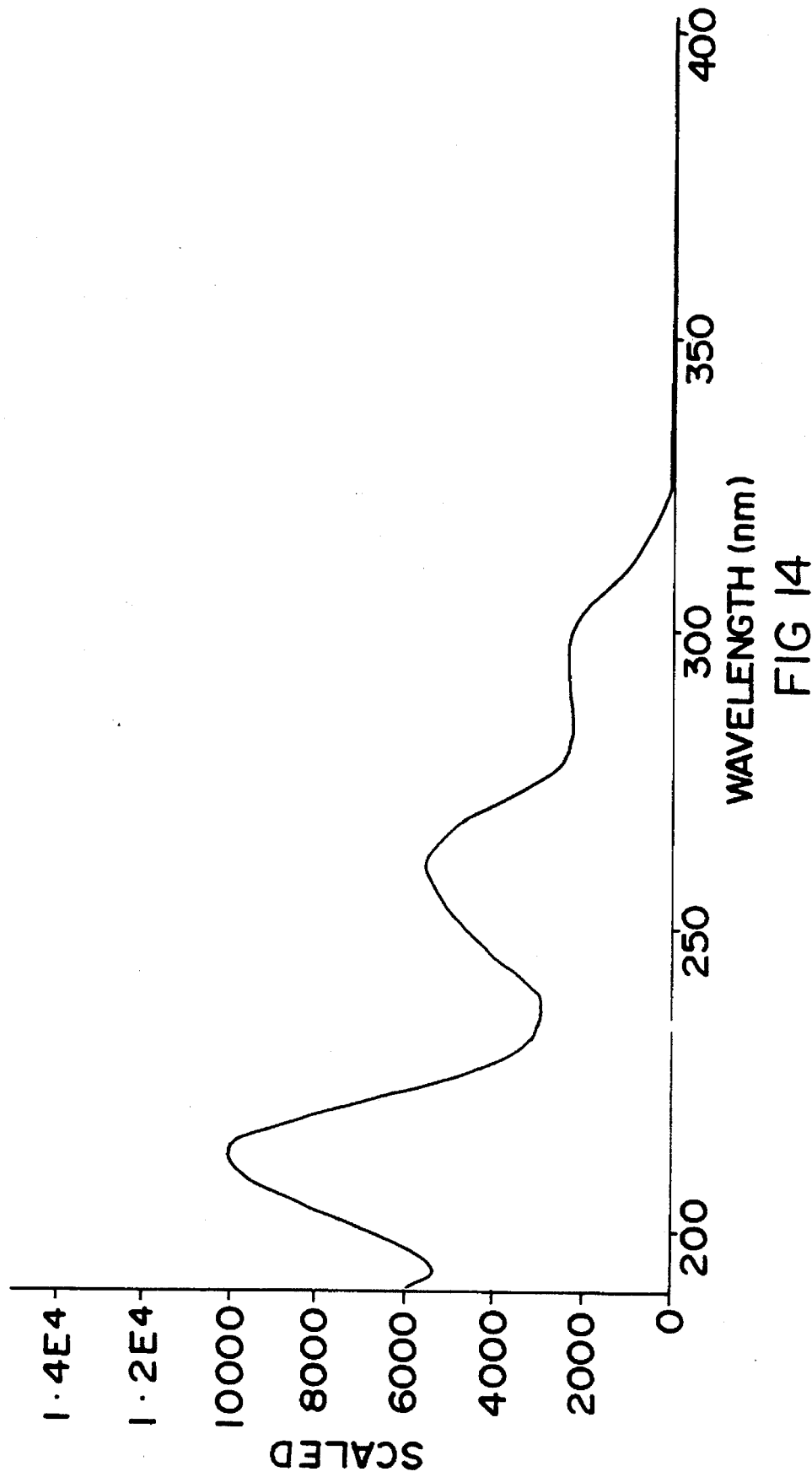
Figure 15:
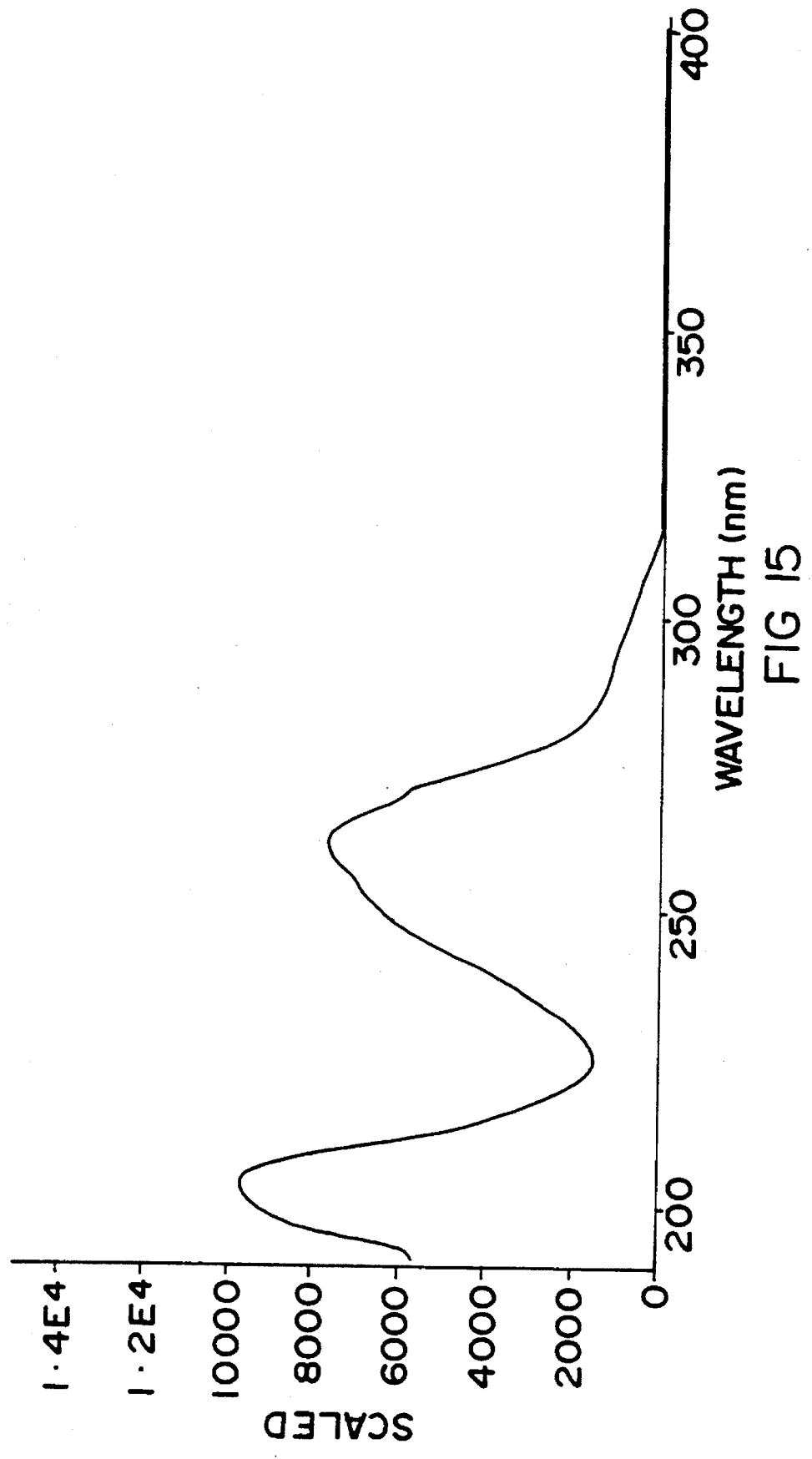
Figure 16:
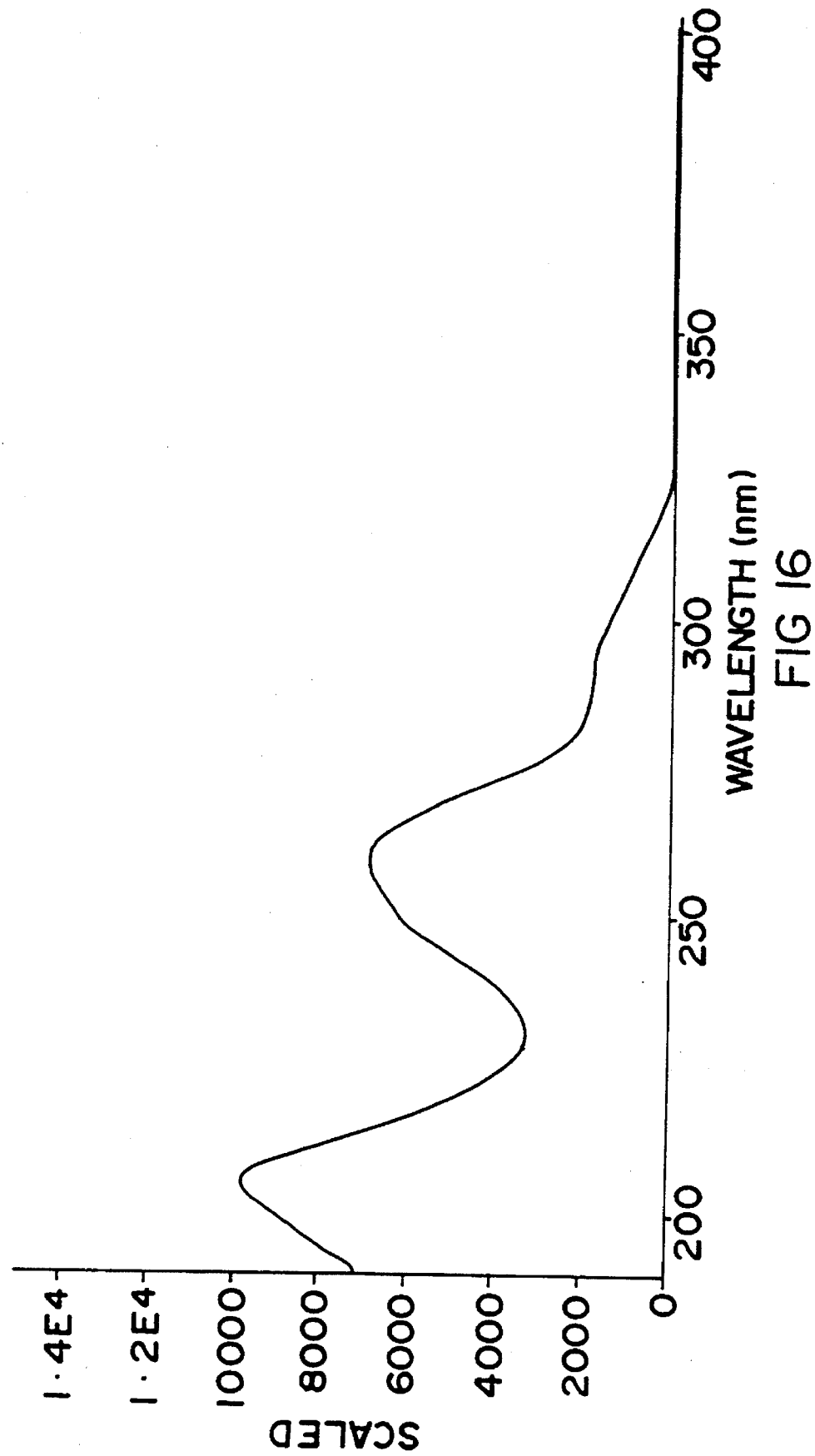
Figure 17:
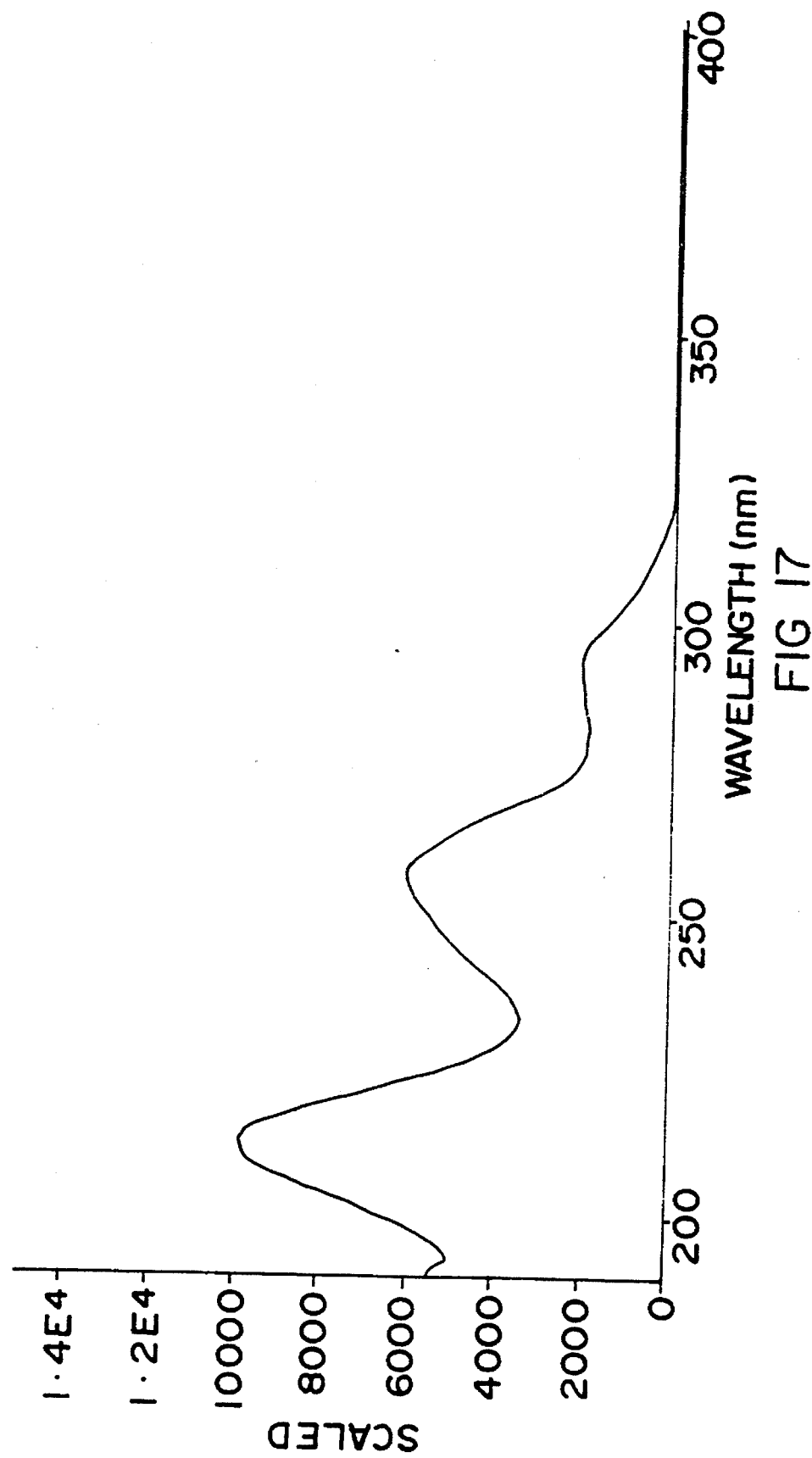
Figure 18:
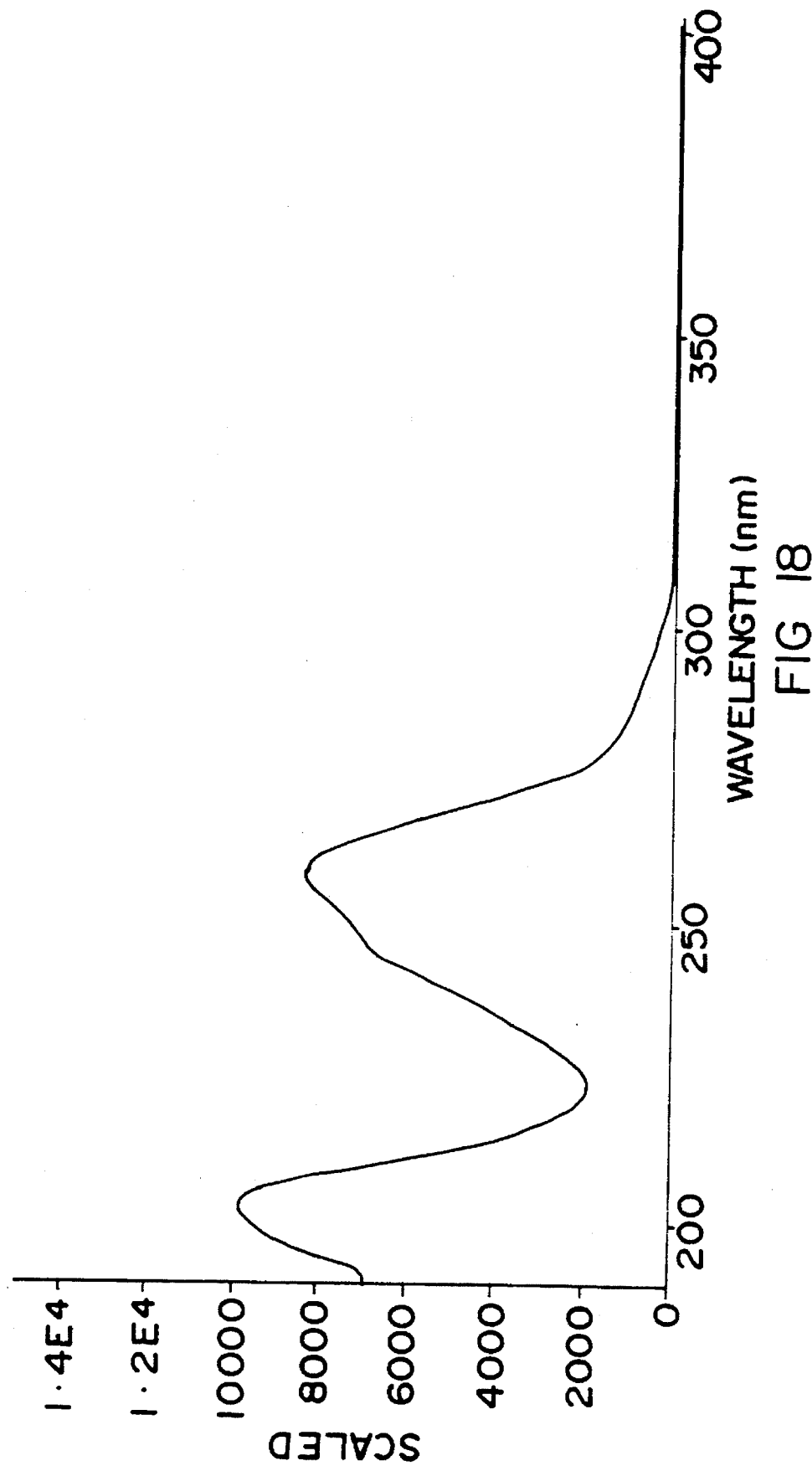
Figure 19:
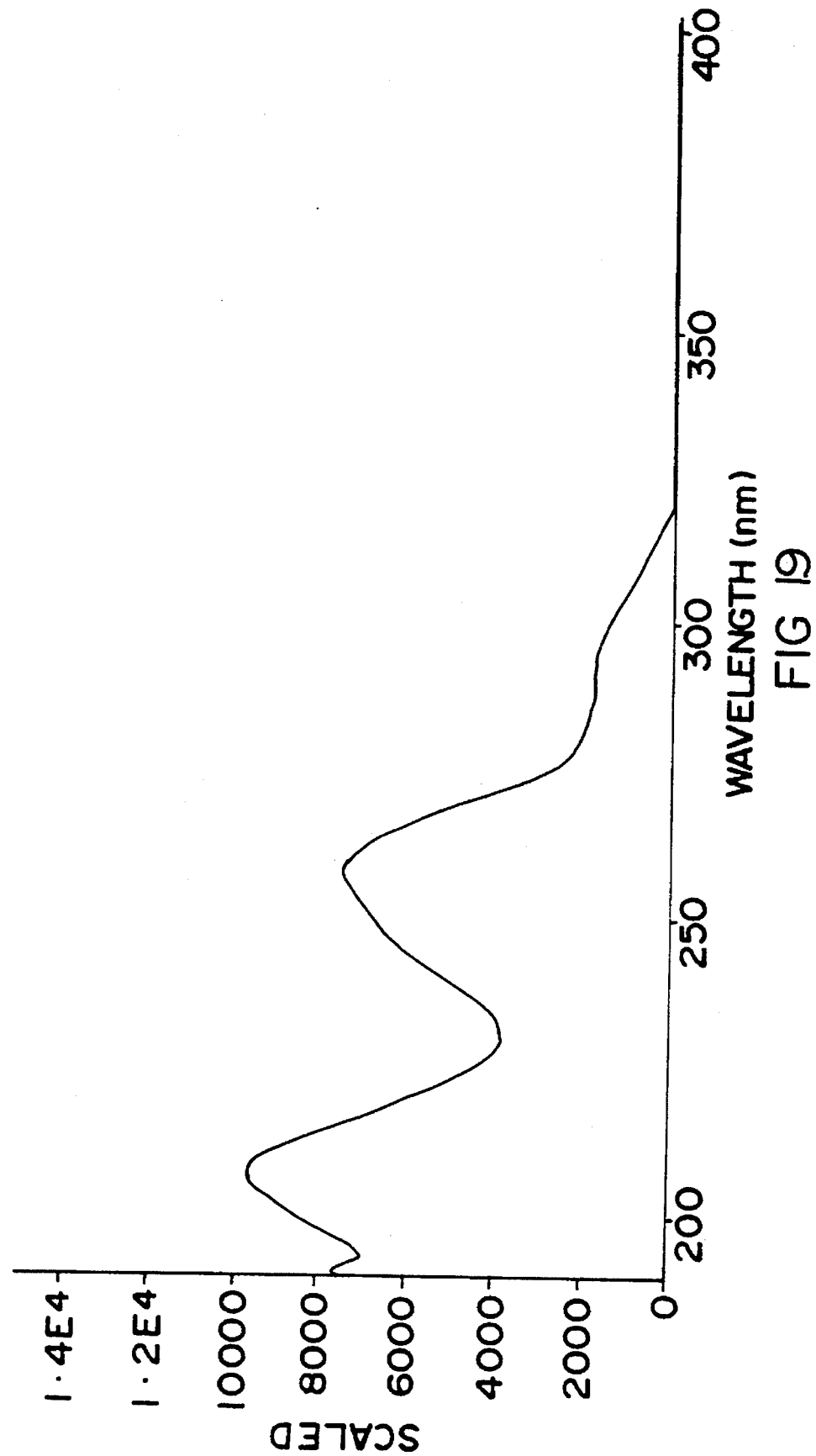
Figure 20:
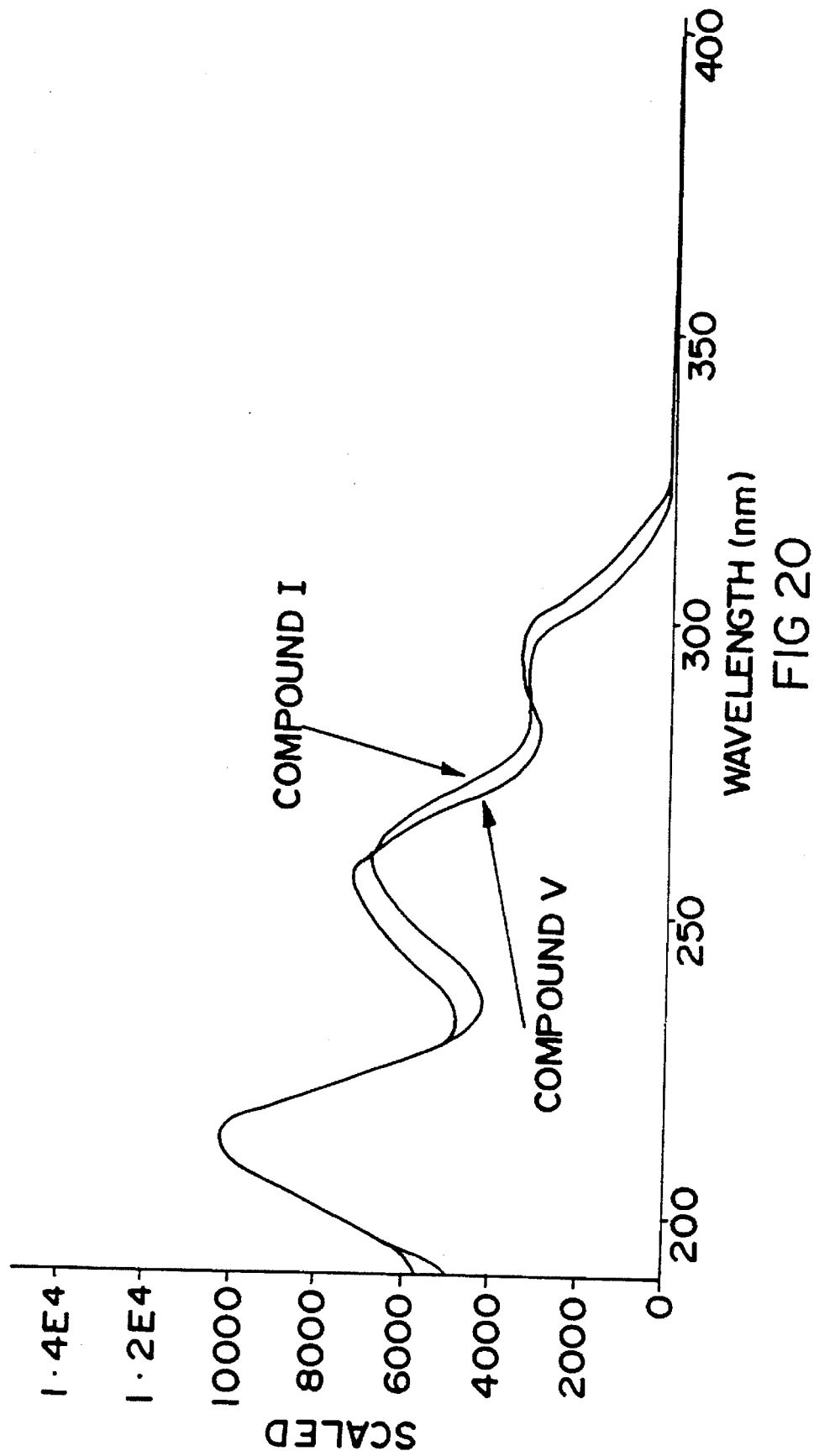
Figure 21:
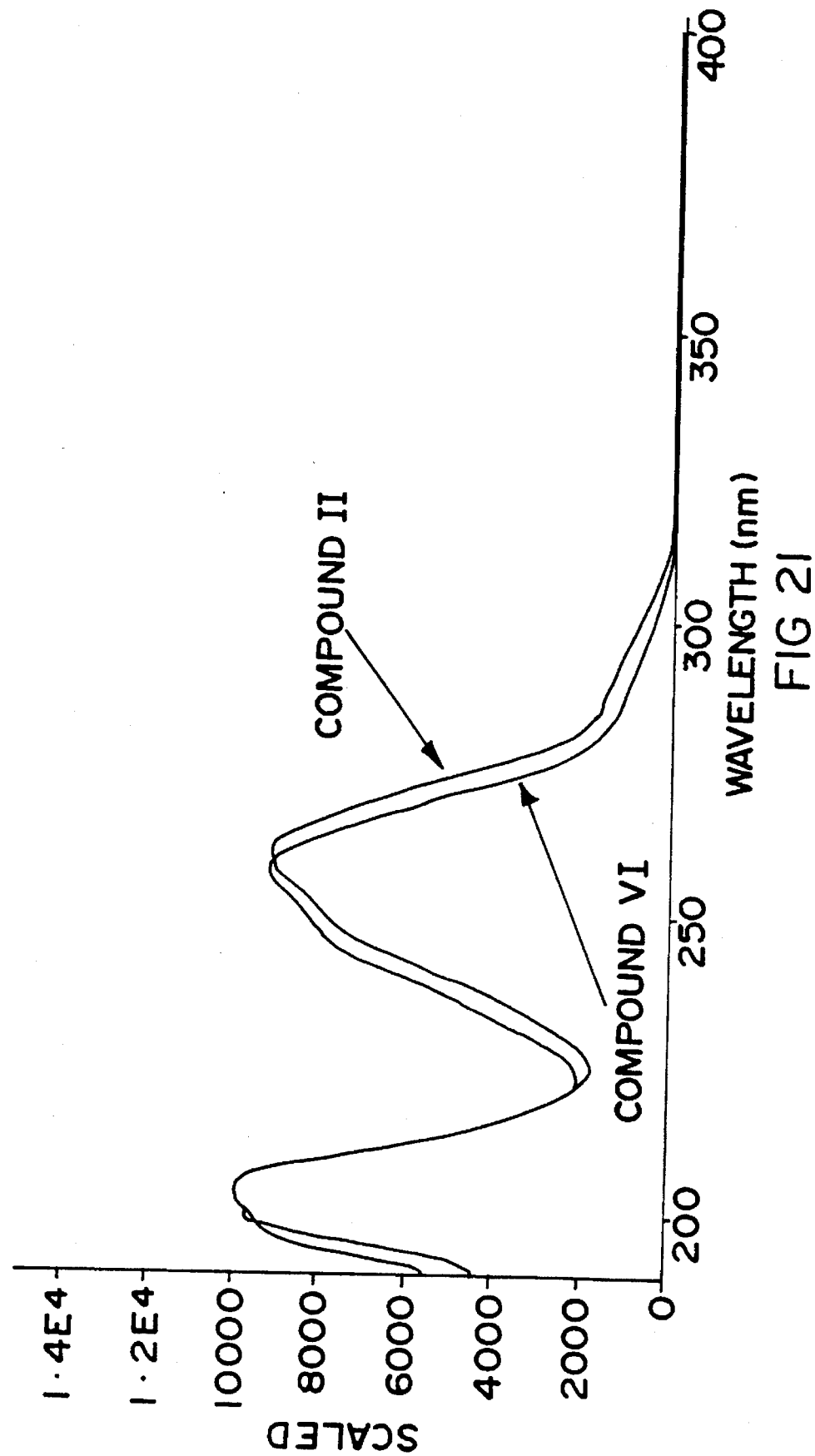
Figure 22:
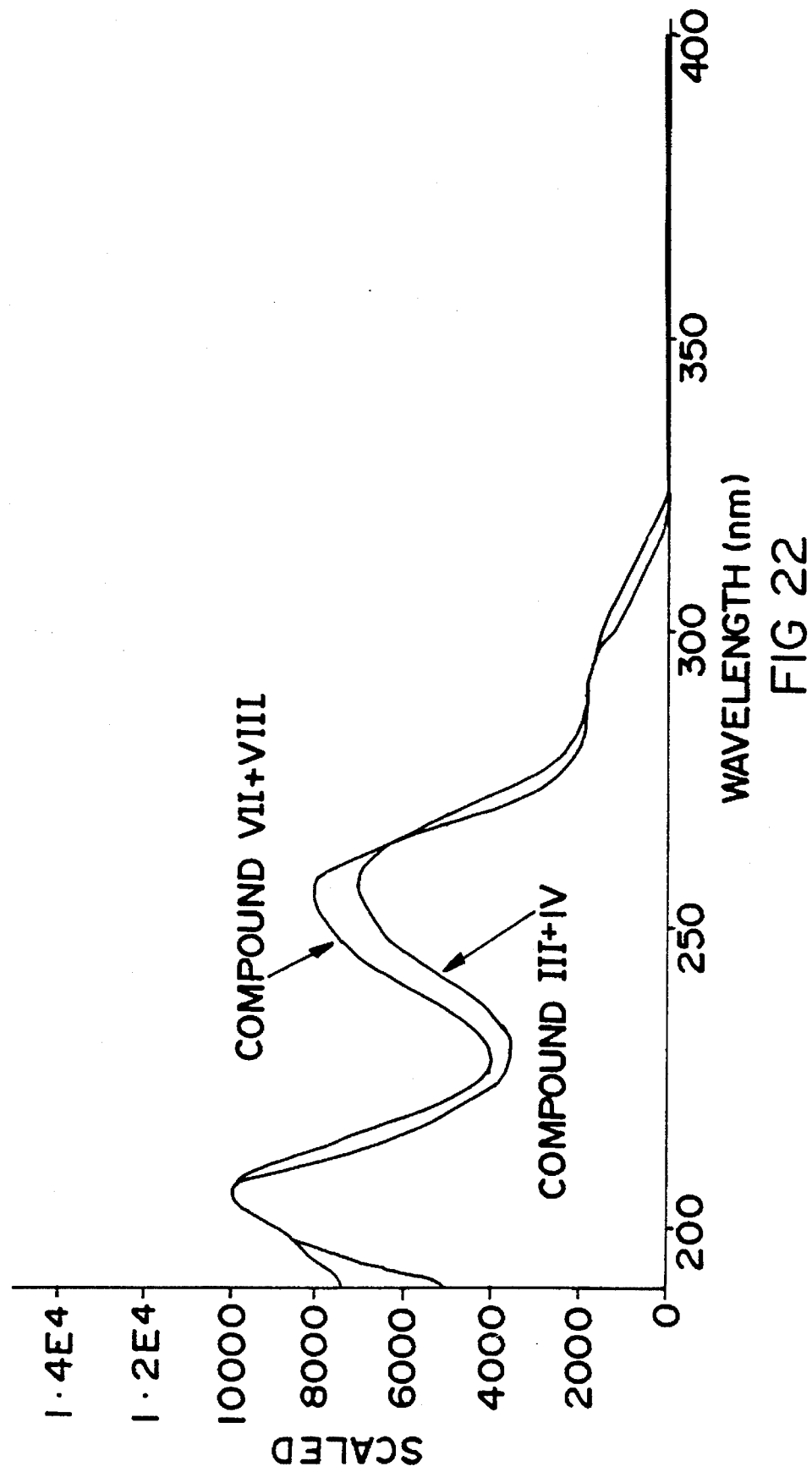
Figure 23:
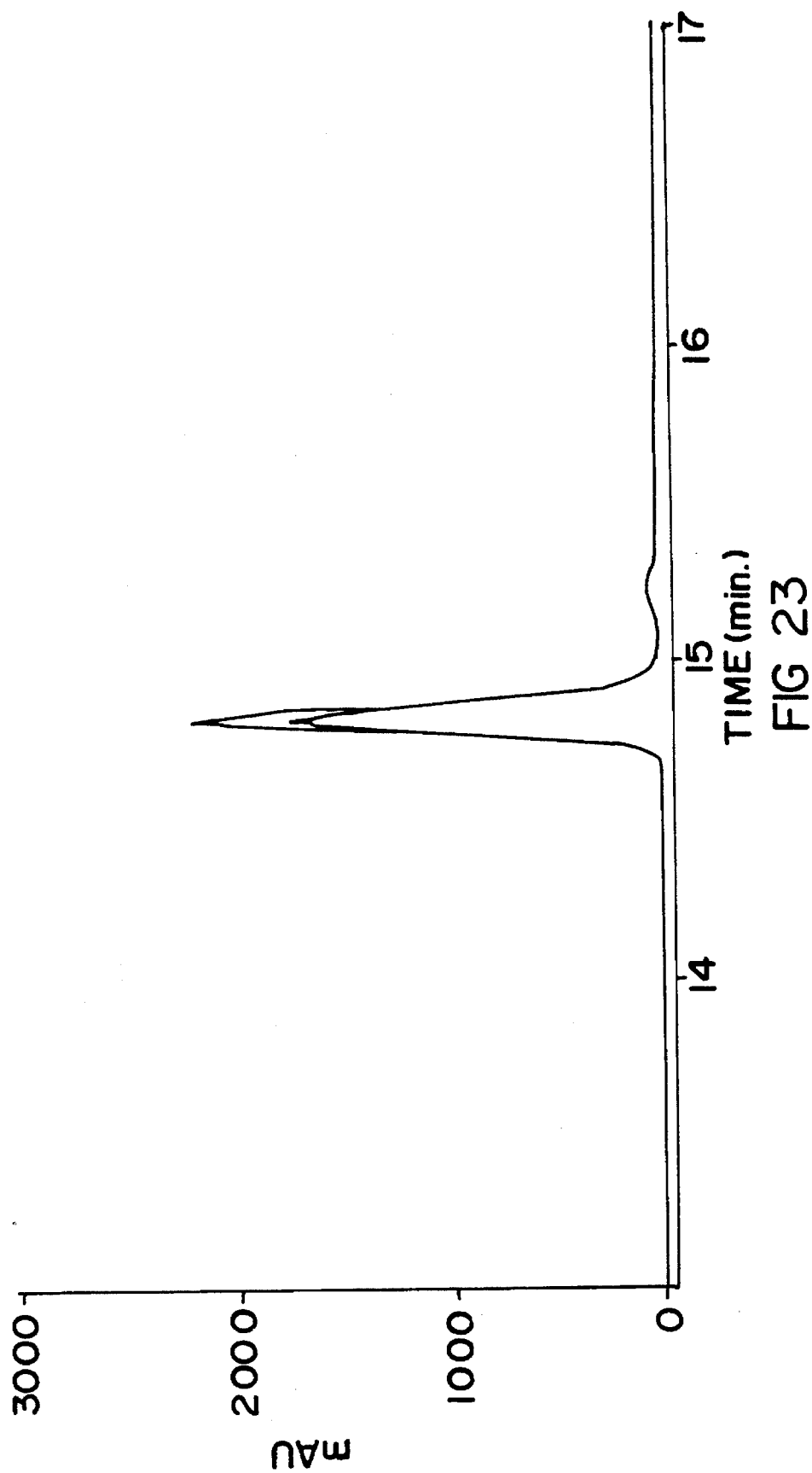
Figure 24:
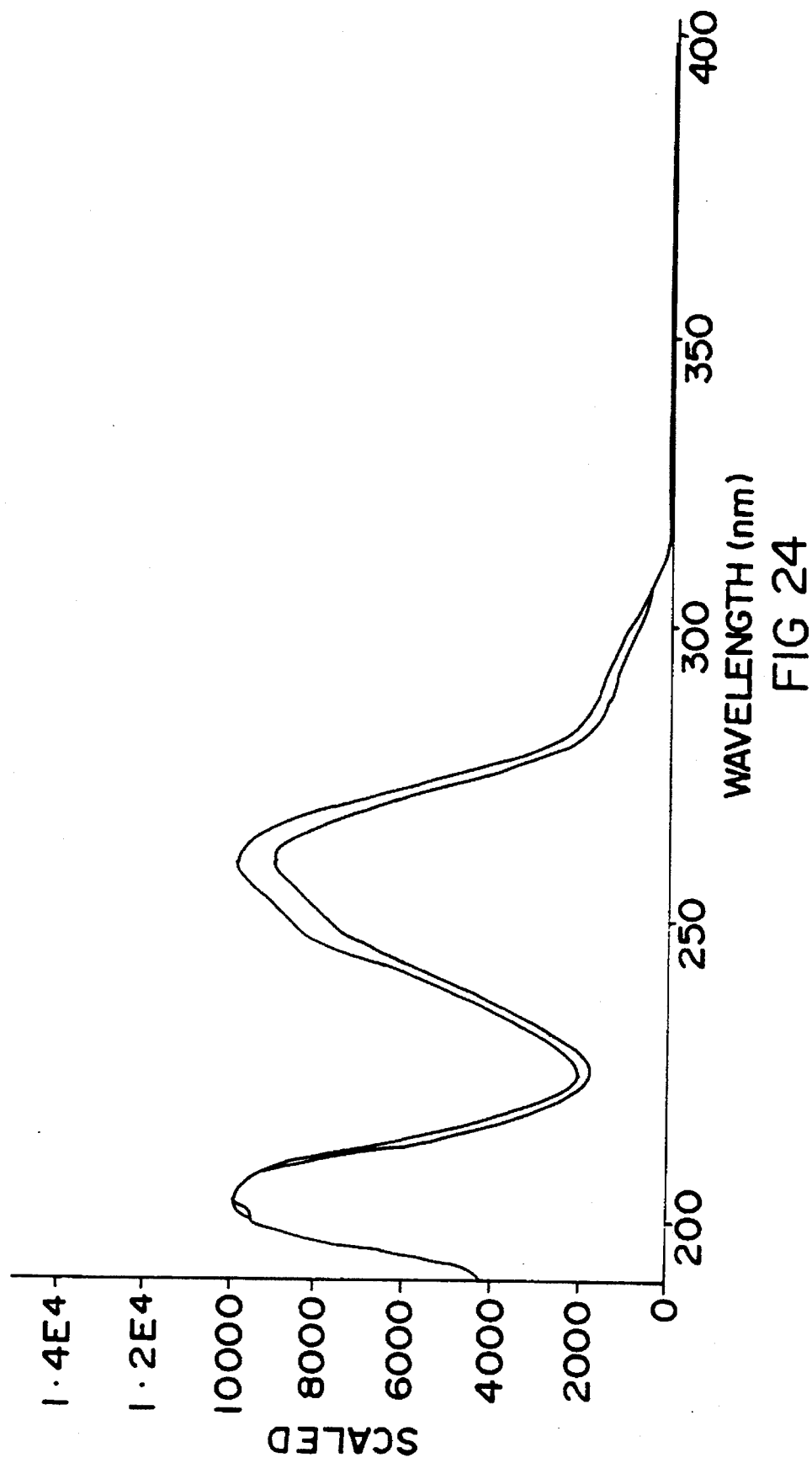
Figure 25:
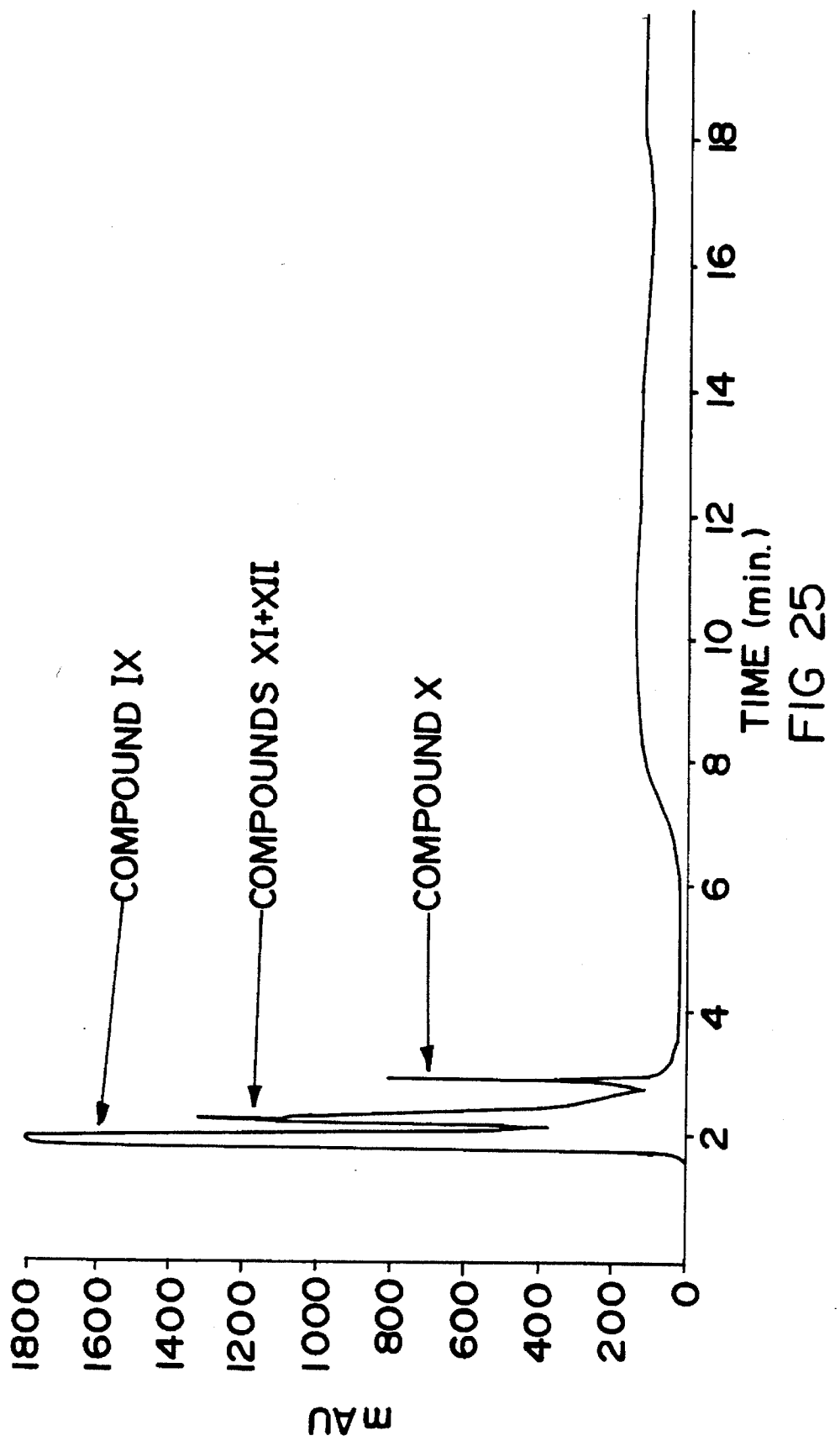
Figure 26:
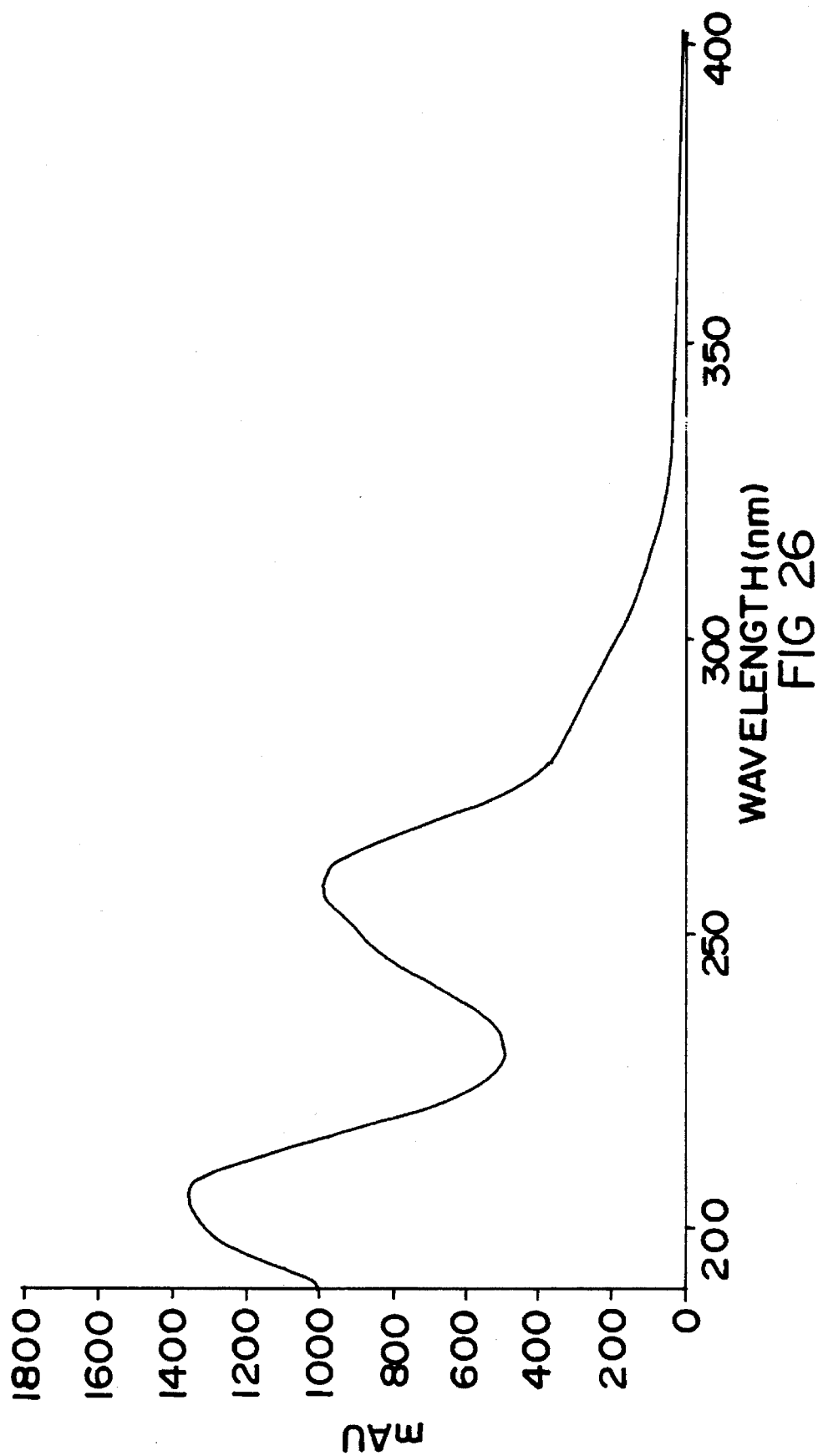
Figure 27:
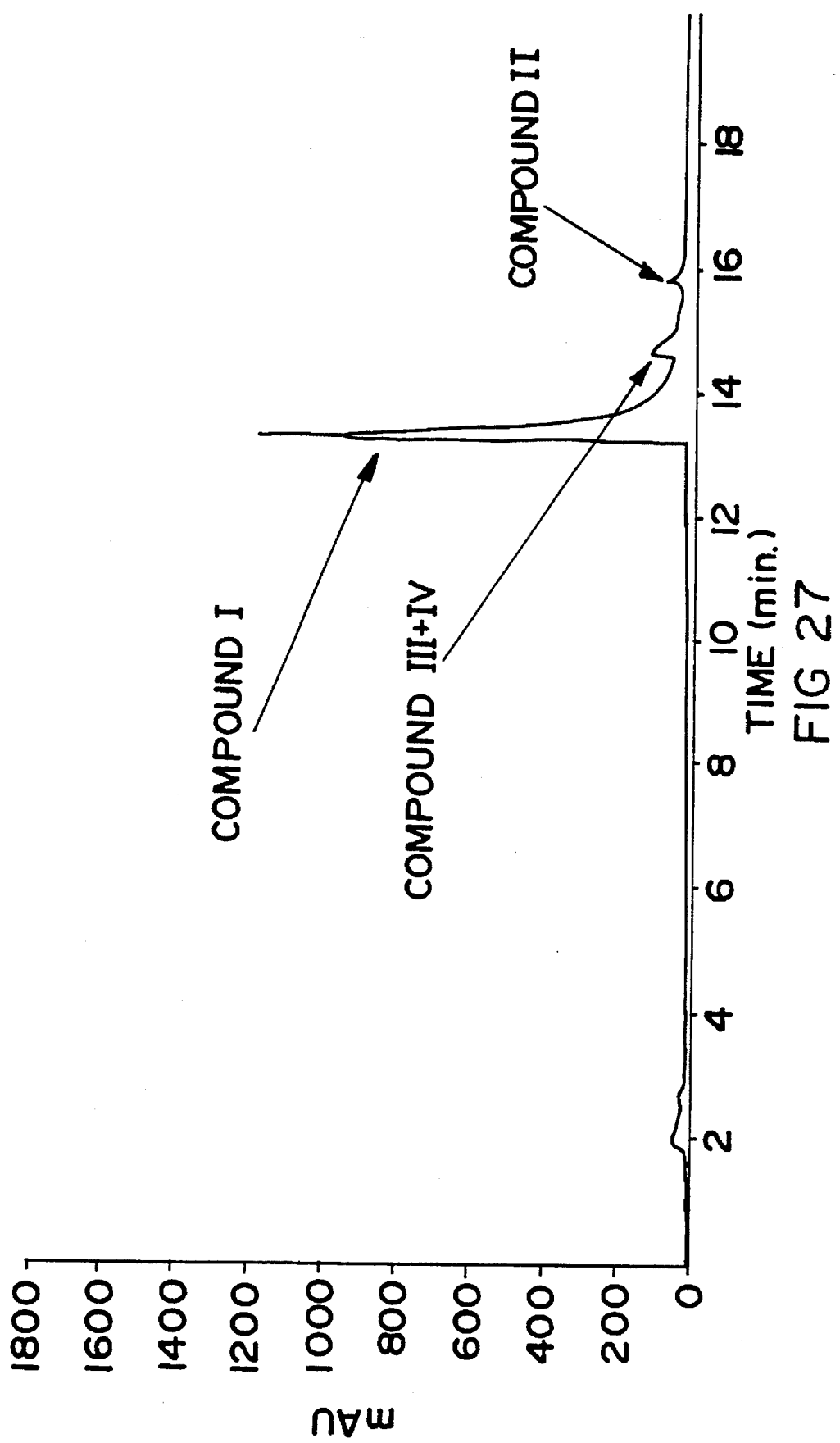

2, the absorption spectra of the urine and plant-derived aconjugates also being superimposable;

FIG. 11 shows a chromatogram, similar to FIG. 10, of said aconjugates derived in similar fashion from purified urine fraction B;

FIG. 12 shows a chromatogram, similar to FIG. 10, of said aconjugates derived in similar fashion from purified urine fraction C;

FIG. 13 shows a chromatogram, similar to FIG. 1, of the products of glucuronidation of compound I, namely the chemically synthesized β-D-glucopyranuronates of compound I obtained by a modified Koenigs-Knorr synthesis, the products being purified by selective solvent partitioning, the chemical β-D-glucuronidation of compound I resulting in two products with retention times and spectra which were coincidental with the urine metabolite fraction A of FIG. 5, the spectrogram in question being superimposed in FIG. 13;

FIG. 14 shows a spectrogram, similar to FIG. 7, but with the mAU axis scaled (normalized), for compound I, having absorption wavelength maxima respectively at 210.5–214.5 nm, 258.5–262.5 nm, and 290.5–294.5 nm, and absorption wavelength minima at 234.5–238.5 nm and 282.5–286.5 nm respectively;

FIG. 15 shows a spectrogram, similar to FIG. 14, but for compound II, having absorption wavelength maxima respectively at 200.5–204.5 nm and 258.5–262.5 nm, and an absorption wavelength minimum at 222.5–226.5 nm;

FIG. 16 shows a spectrogram, similar to FIG. 14, but for compounds (III+IV), having absorption wavelength maxima at 202.5–206.5 nm and 258.5–262.5 nm respectively, and an absorption wavelength minimum at 228.5–232.5 nm;

FIG. 17 shows spectrogram, similar to FIG. 14, but for compound V, having absorption wavelength maxima respectively at 210.5–212.5 nm, 254.5–258.5 nm and 288.5–292.5 nm, and absorption wavelength minima at 232.5–234.5 nm and 278.5–282.5 nm respectively;

FIG. 18 shows a spectrogram, similar to FIG. 14, but for compound VI, having absorption wavelength maxima respectively at 200.5–204.5 nm and 256.5–260.5 nm, and an absorption wavelength minimum at 220.5–224.5 nm;

FIG. 19 shows a spectrogram, similar to FIG. 14, but for compounds (VII+VIII), having absorption wavelength maxima respectively at 204.5–208.5 nm and 256.5–260.5 nm, and an absorption wavelength minimum at 226.5–230.5 nm;

FIG. 20 shows a spectrogram, similar to FIG. 14, but showing superimposed absorption spectra for compounds I and V;

FIG. 21 shows a spectrogram, similar to FIG. 14, but showing superimposed absorption spectra for compounds II and VI;

FIG. 22 shows a spectrogram, similar to FIG. 14, but showing superimposed absorption spectra for compounds (III+IV) and (VII+VIII);

FIG. 23 shows superimposed chromatograms, similar to FIG. 1, of compound II obtained from natural and synthetic sources respectively, the natural compound being obtained by the enzymatic deglucosidation of HPLC-purified compound V obtained from H. rooperi, whereas the synthetic compound was synthesized as described by Drewes et al: Synthetic Communications, 1990, 20, 1671–1679;

FIG. 24 shows a spectrogram, similar to FIG. 14, of superimposed absorption spectra of the synthetic and natural versions of compound II whose chromatograms are shown in FIG. 23;

FIG. 25 shows a chromatogram, similar to FIG. 1, for a mixture of compounds IX–XII obtained by the per-sulphation of a mixture of compounds V–VIII;

FIG. 26 shows a spectrogram, similar to FIG. 7, for the mixture of compounds IX–XII whose chromatogram is shown in FIG. 25;

FIG. 27 shows a chromatogram, similar to FIG. 1, for compounds I–IV as derived from H. rooperi, being the products of hydrolysis of compounds V–VIII whose chromatogram is shown in FIG. 3, by β-D-glucosidase at pH 5.5, the retention times being:

| Compound | Retention Time (minutes) |
|---|---|
| I | 12.31 |
| II | 14.88 |
| (III + IV) | 13.53; |

Figure 28:
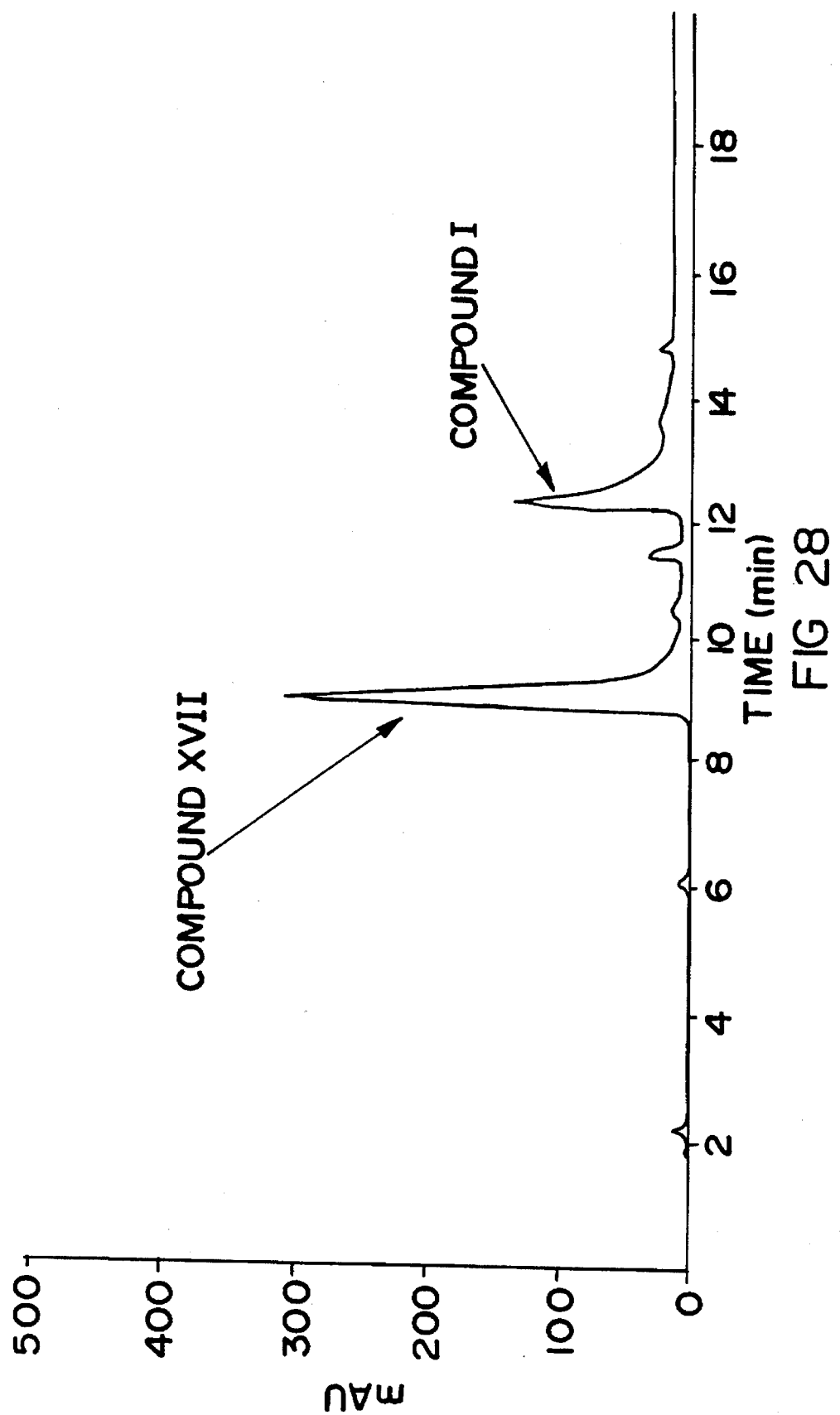

FIG. 28 shows a chromatogram, similar to FIG. 1, of a mixture of compound I and its semisynthetic di-sulphated product, compound XVII, retention times being:

| Compound | Retention Time (minutes) |
|---|---|
| I | 12.29 |
| XVII | 8.95; |

Figure 29:
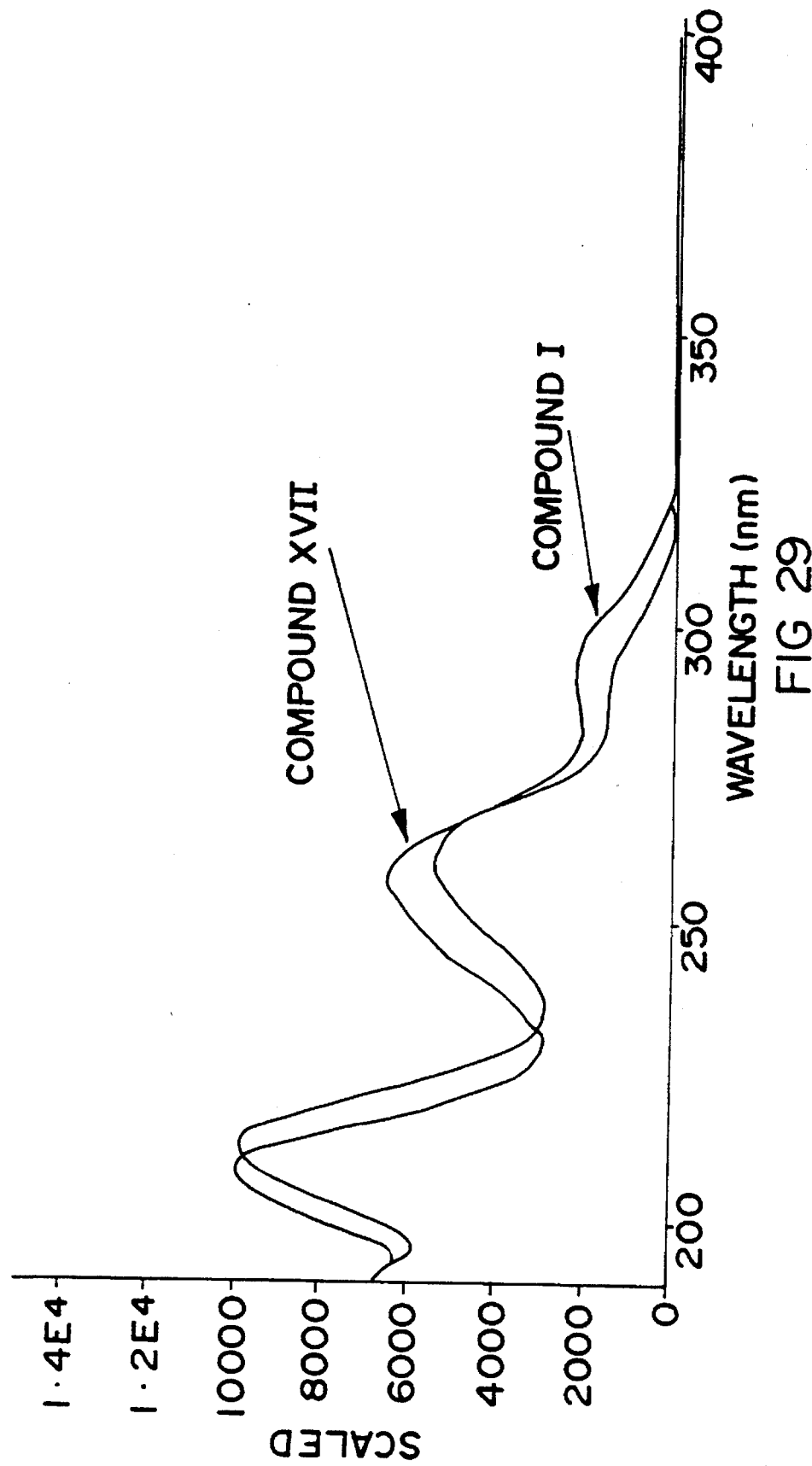
Figure 30:
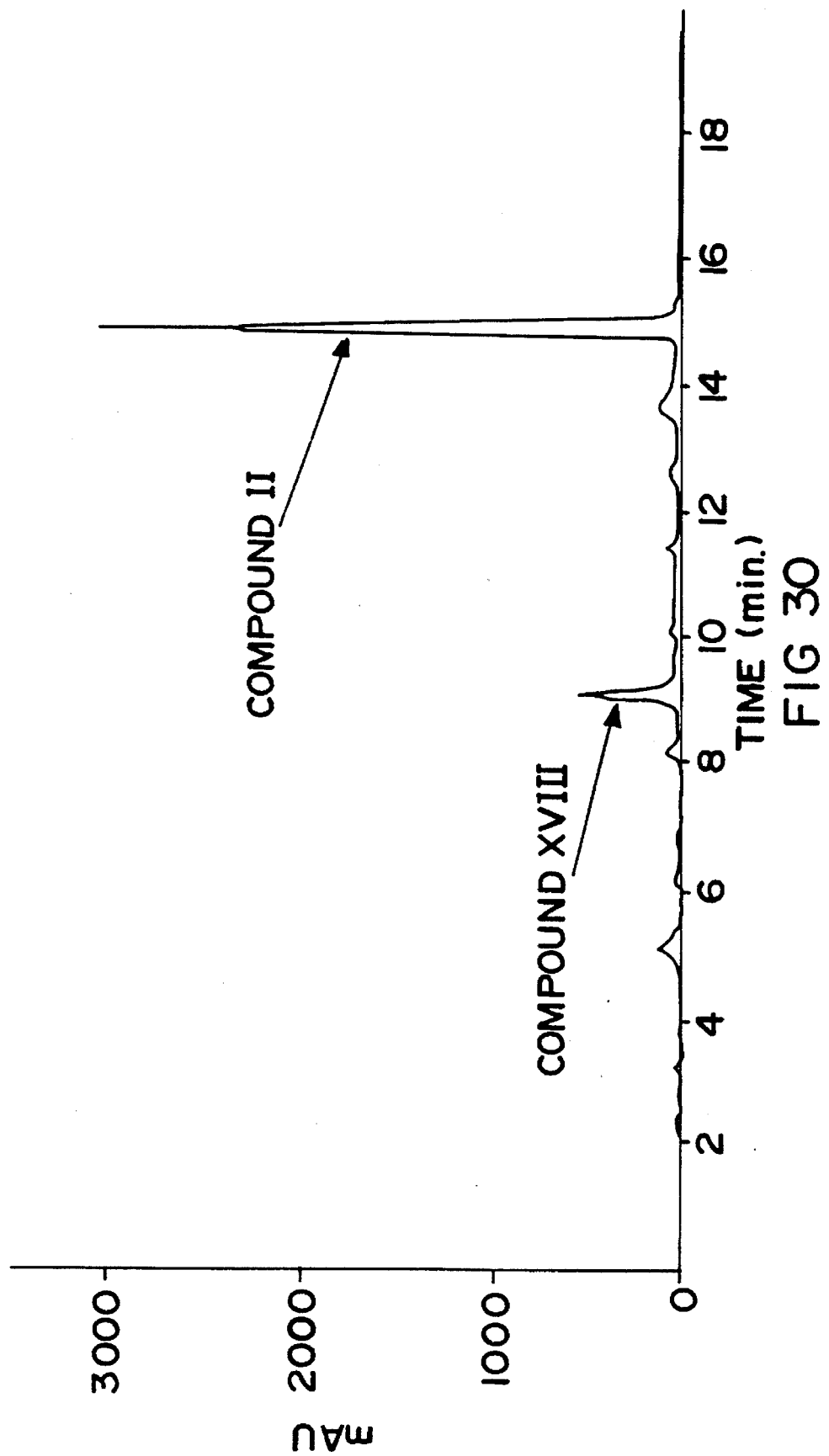

FIG. 29 shows a spectrogram, similar to FIG. 14, for compounds I and XVII whose chromatogram is shown in FIG. 28, compound I having absorption wavelength maxima respectively at 210.5–214.5 nm, 258.5–262.5 nm and 290.5–294.5 nm and absorption wavelength minima at 234.5–238.5 nm and 282.5–286.5 nm, while compound XVII had absorption wavelength maxima at 204.5–208.5 nm and 254.5–258.5 nm and an absorption wavelength minimum at 226.5–230.5 nm;

FIG. 30 shows a chromatogram, similar to FIG. 1, for a mixture of compound II and semi-synthetic compound XVIII which is the di-sulphated conjugate product of compound II, retention times being:

| Compound | Retention Time (minutes) |
|---|---|
| II | 14.86 |
| XVIII | 9.07; |

Figure 31:
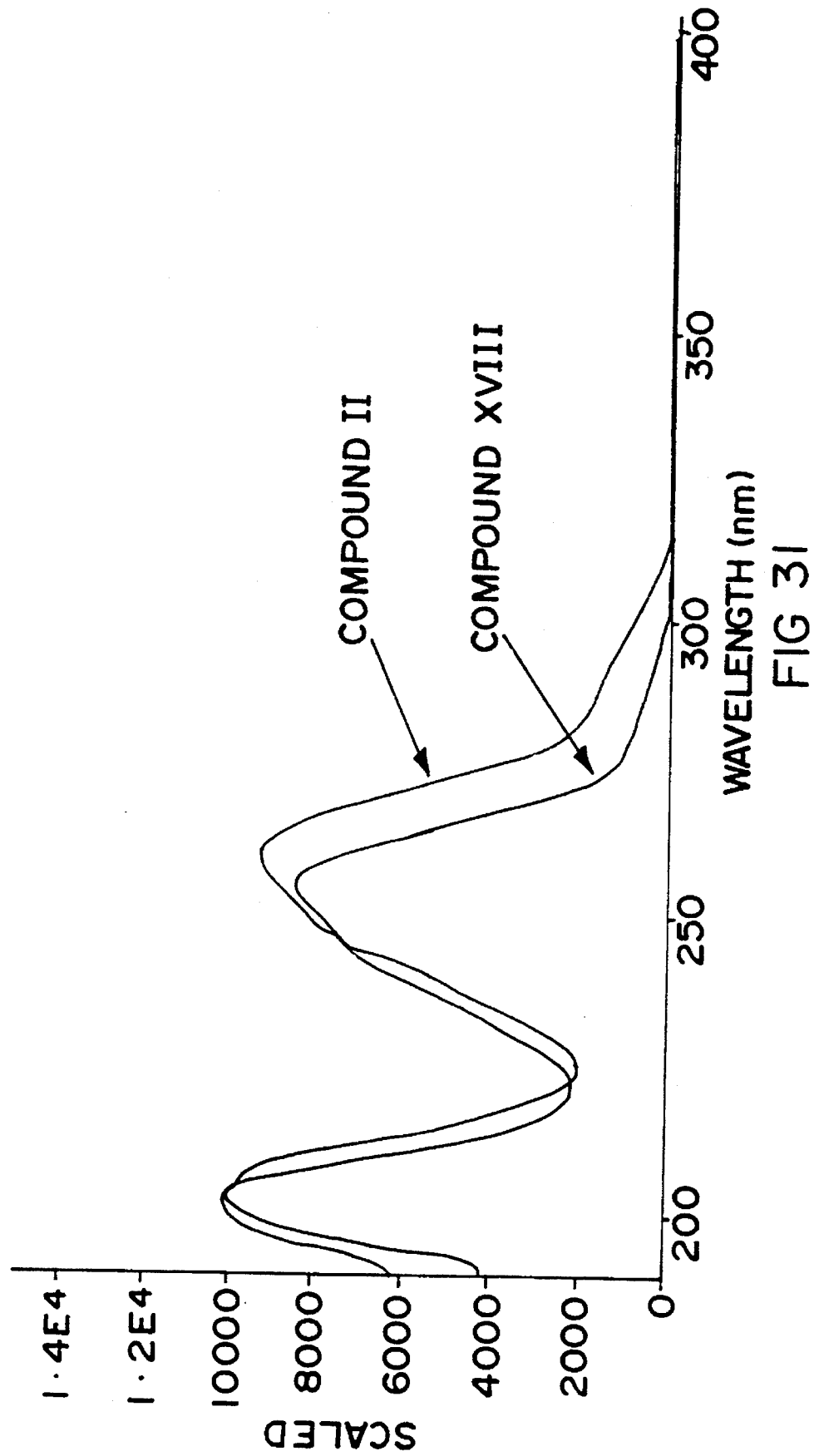
Figure 32:
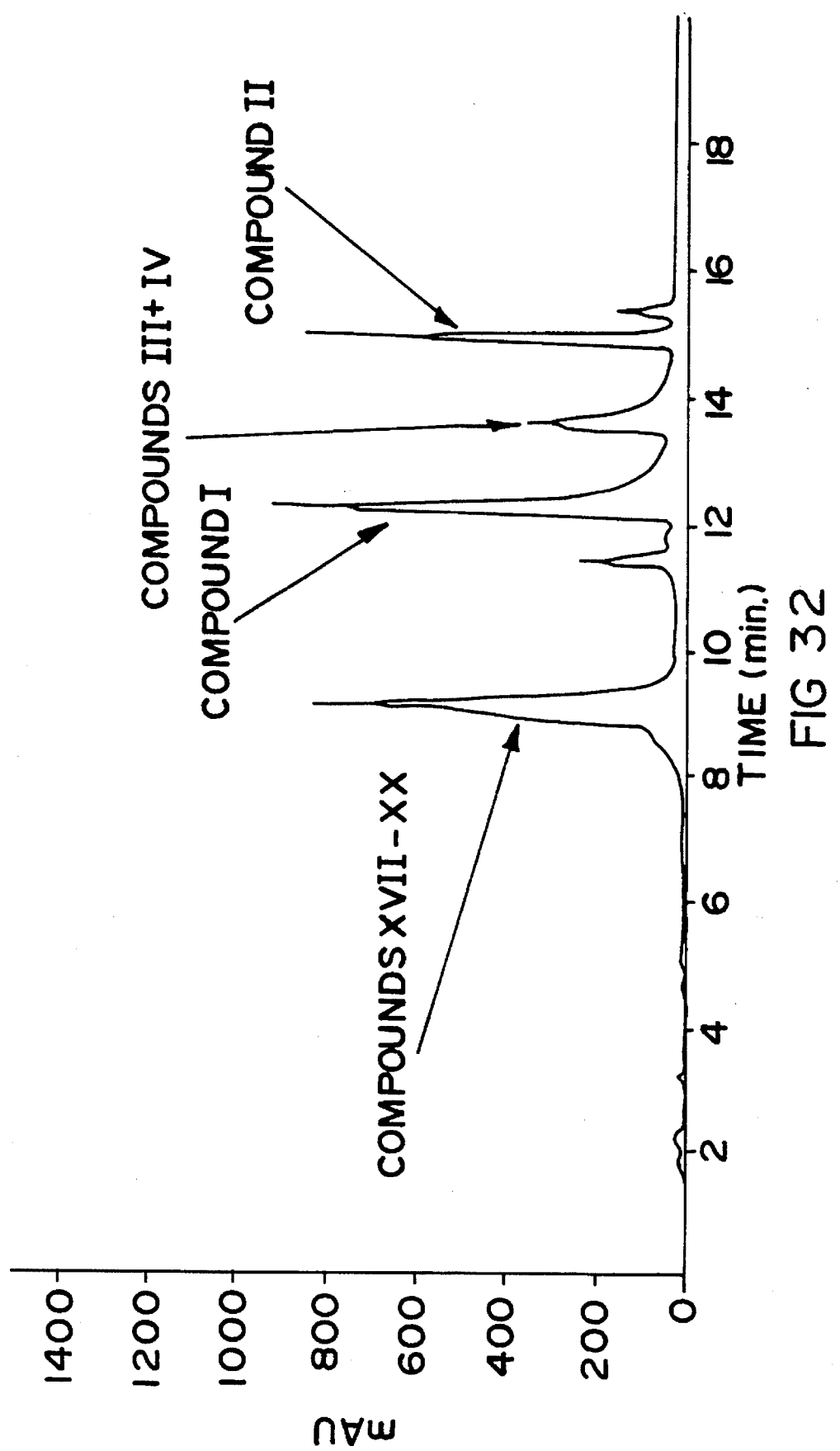

FIG. 31 shows a spectrogram, similar to FIG. 14, for compounds II and XVIII whose chromatogram is shown in FIG. 30, compound II having absorption wavelength maxima respectively at 200.5–204.5 nm and 258.5–262.5 nm, and an absorption wavelength minimum at 222.5–226.5 nm, and compound XVIII having absorption wavelength maxima at 198.5–202.5 nm and 254.5–258.5 nm, and an absorption wavelength minimum at 220.5–224.5 nm, the absorption spectrum of the di-sulphated product, compound XVIII, displaying a shift to a shorter wavelength, compared with that of compound II;

FIG. 32 shows a chromatogram, similar to FIG. 1, of a mixture of compounds I–IV and of their semi-synthetic di-sulphated conjugates, compounds XVII–XX, obtained by the di-sulphatation of the mixture of compounds I–IV, illustrating the co-elution of the di-sulphates of compounds I–IV, namely compounds XVII–XX, retention times being:

| Compound | Retention Times (minutes |
|---|---|
| I | 12.14 |
| II | 14.80 |
| (III + IV) | 13.51 |
| XVII–XX | 9.00. |

Figure 33:
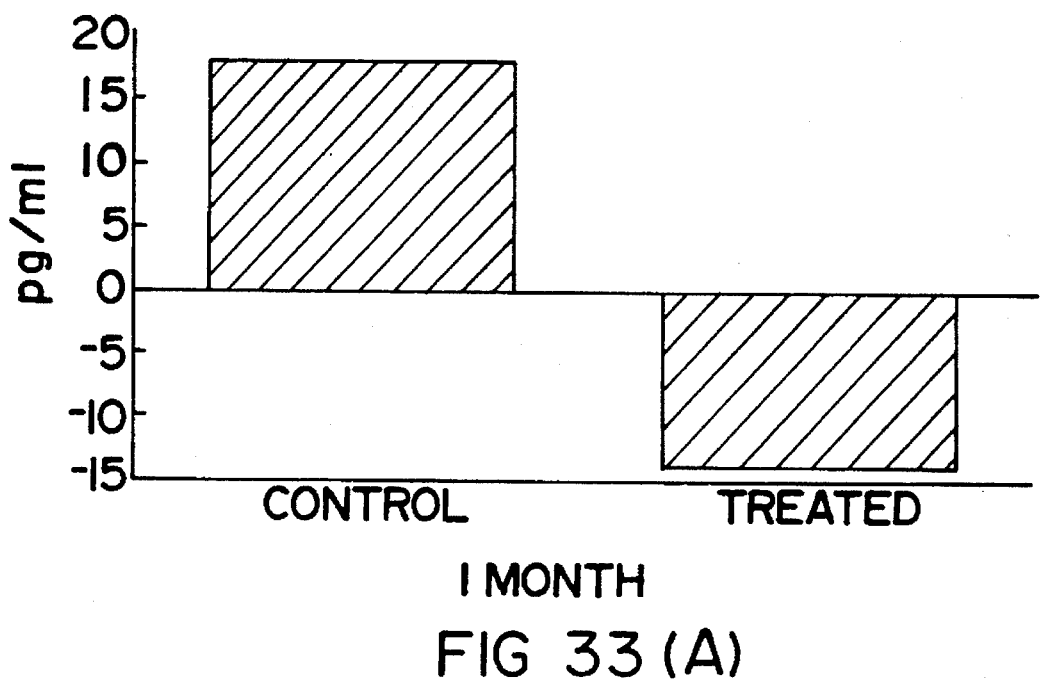
Figure 33:
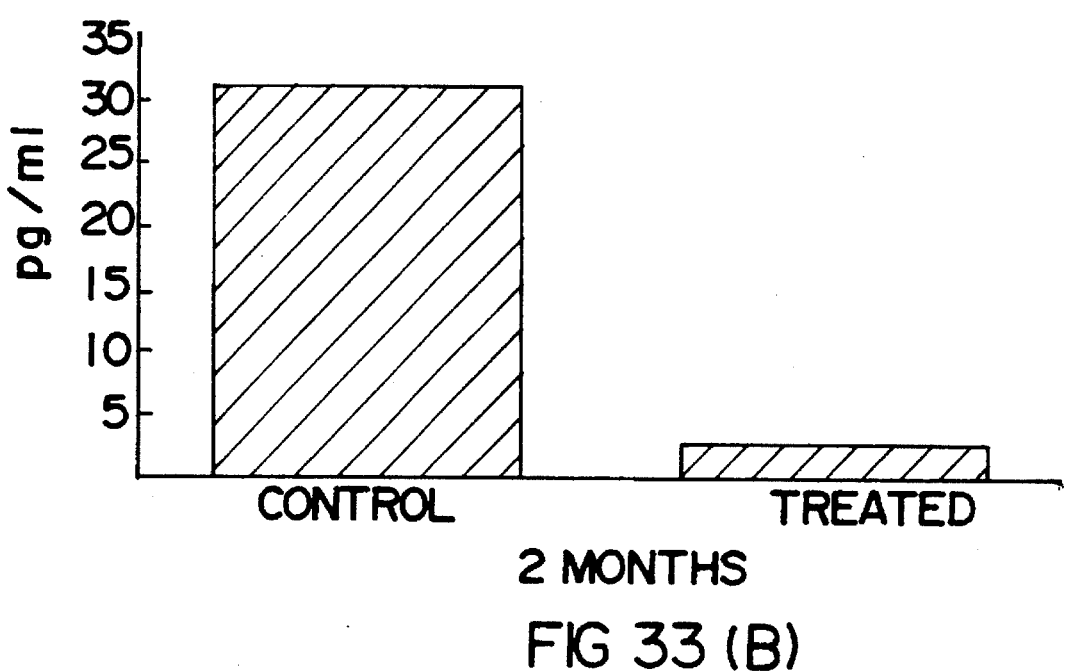
Figure 34A:
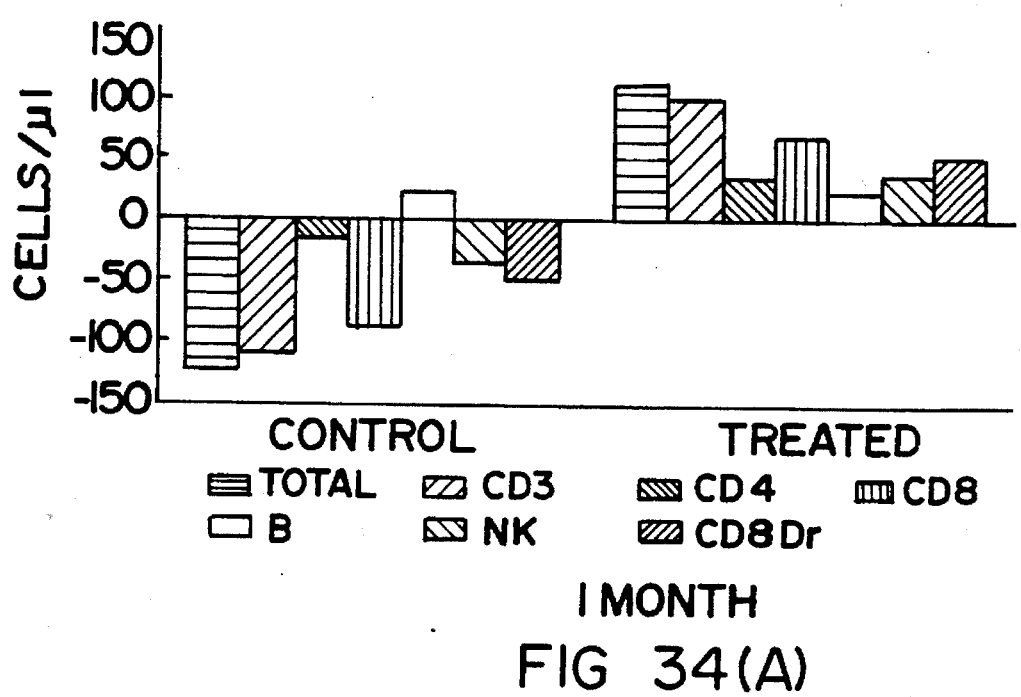
Figure 34B:
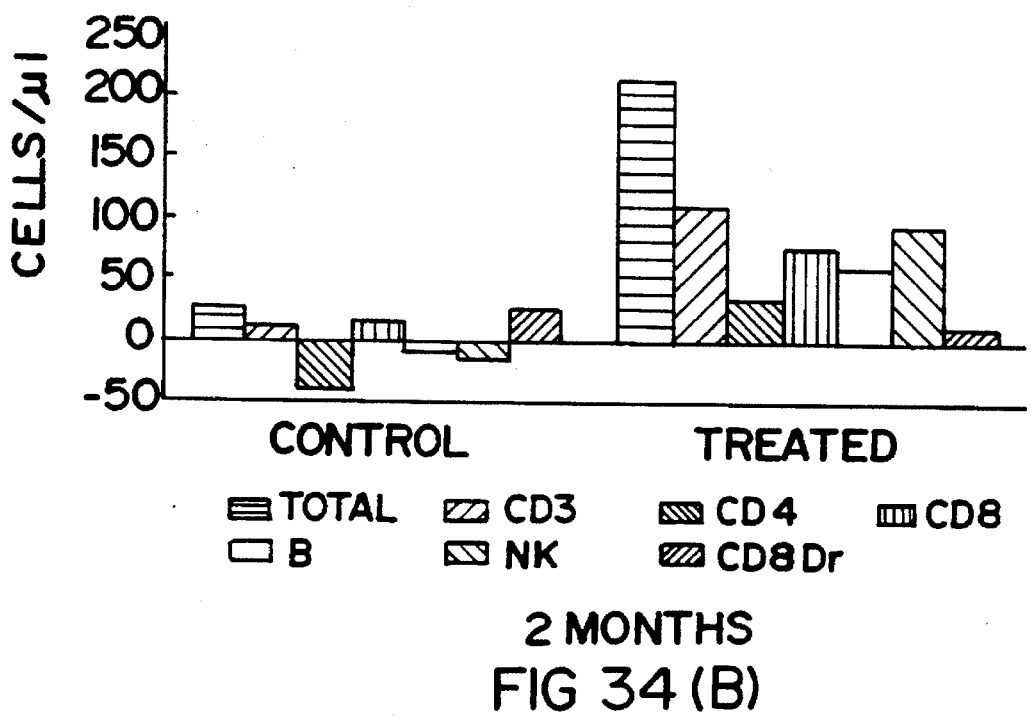
Figure 35A:
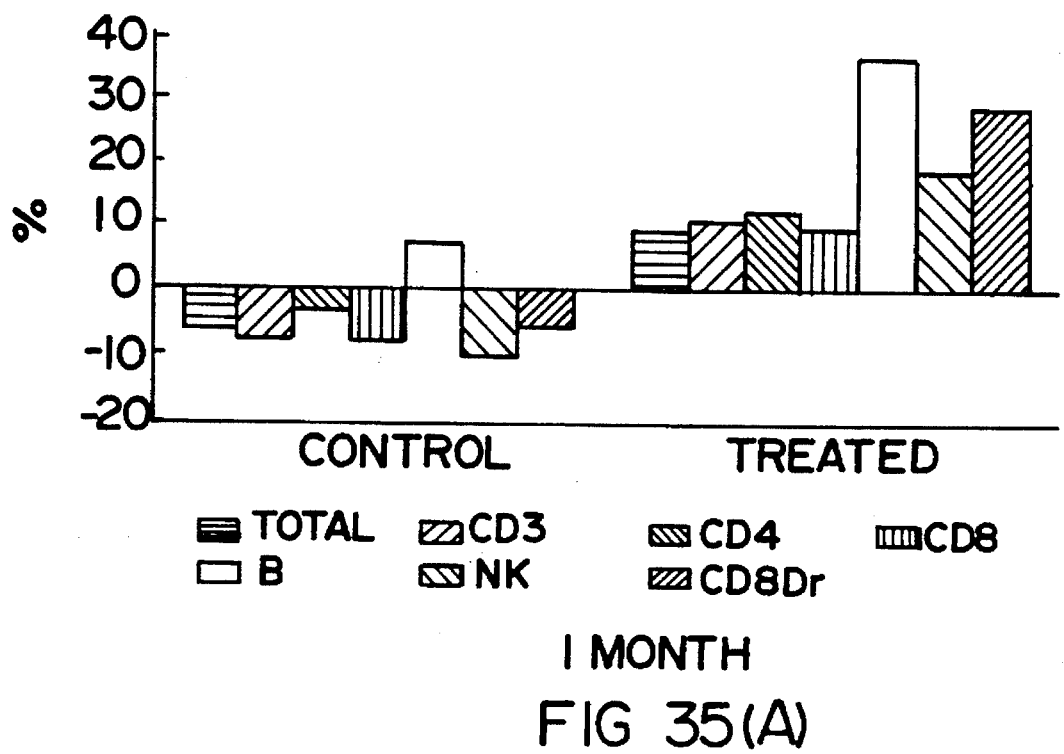
Figure 35B:
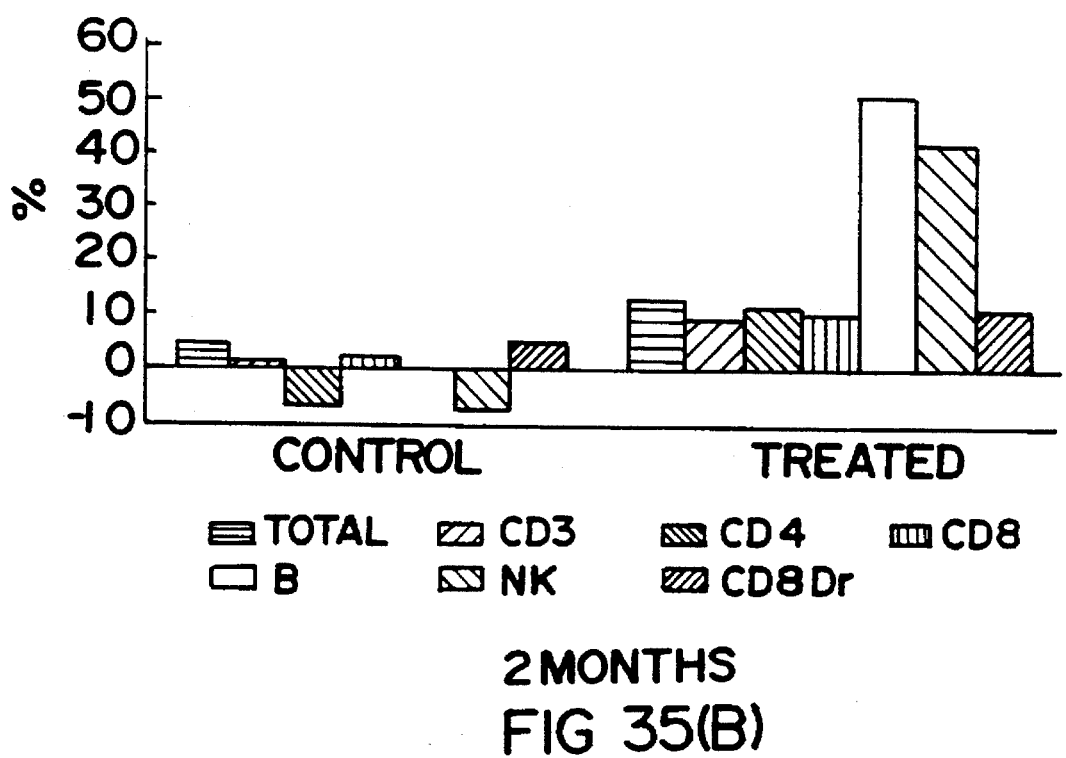

FIG. 33 shows bar charts of results of a HIV pilot study showing mean absolute changes of p24 core protein levels in pg/ml within groups of treated (invention) and non-treated (control) subjects;

FIG. 34 shows bar charts of the pilot study of FIG. 33, but for mean absolute changes in cells/µl within said treated and non-treated groups for selected lymphocyte subsets; and FIG. 35 shows bar charts of the pilot study of FIG. 33, but for mean percentage changes within said groups for said cell subsets.

Figure 36:
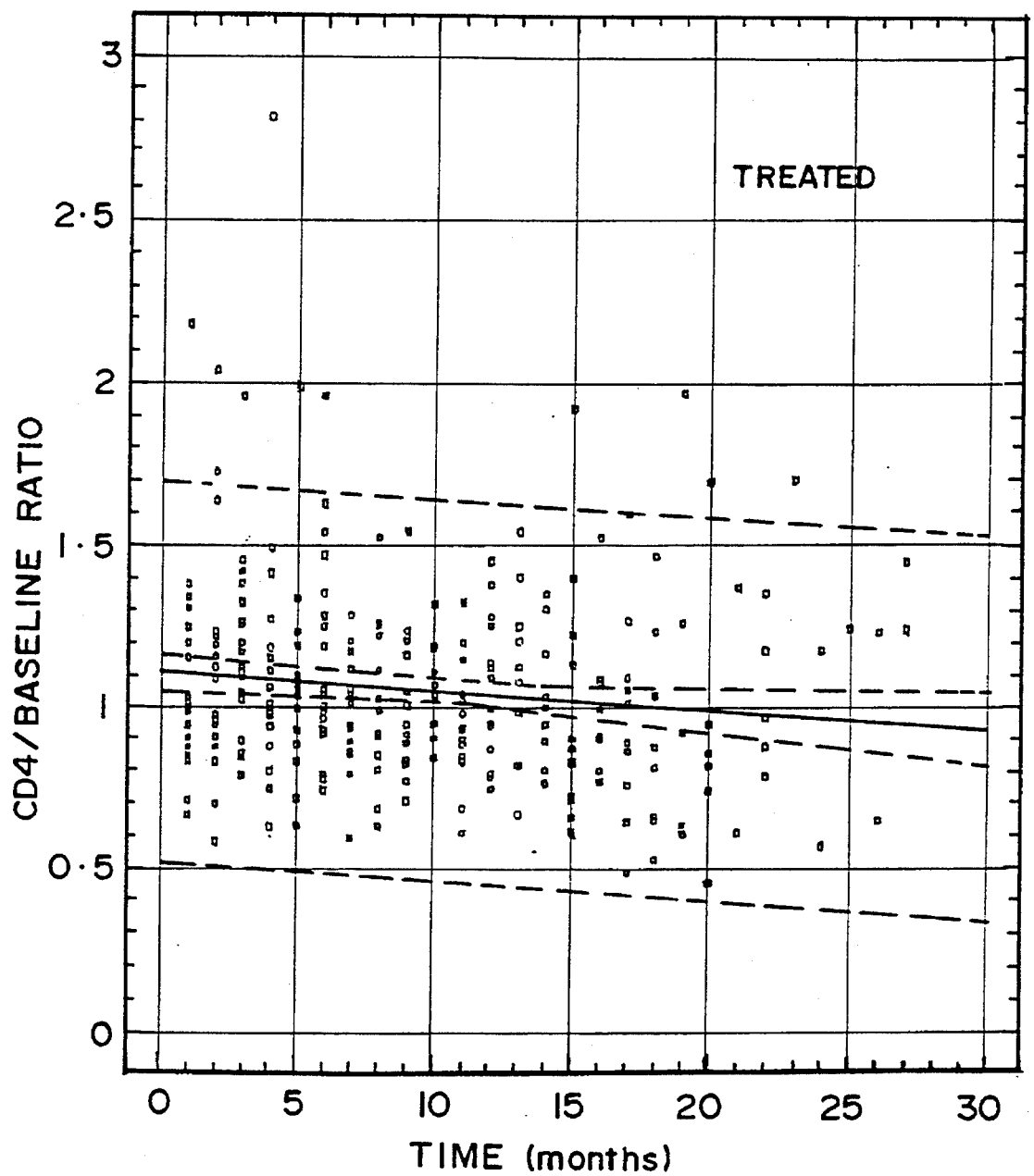

FIG. 36 depicts regression analysis of the data from treated patients, showing a plot of CD4/baseline ratio as a function of time in months, the confidence limits being shown as the dotted lines closest to the regression line and the prediction limits being shown as the dotted lines furthest from the regression line.

Figure 37:
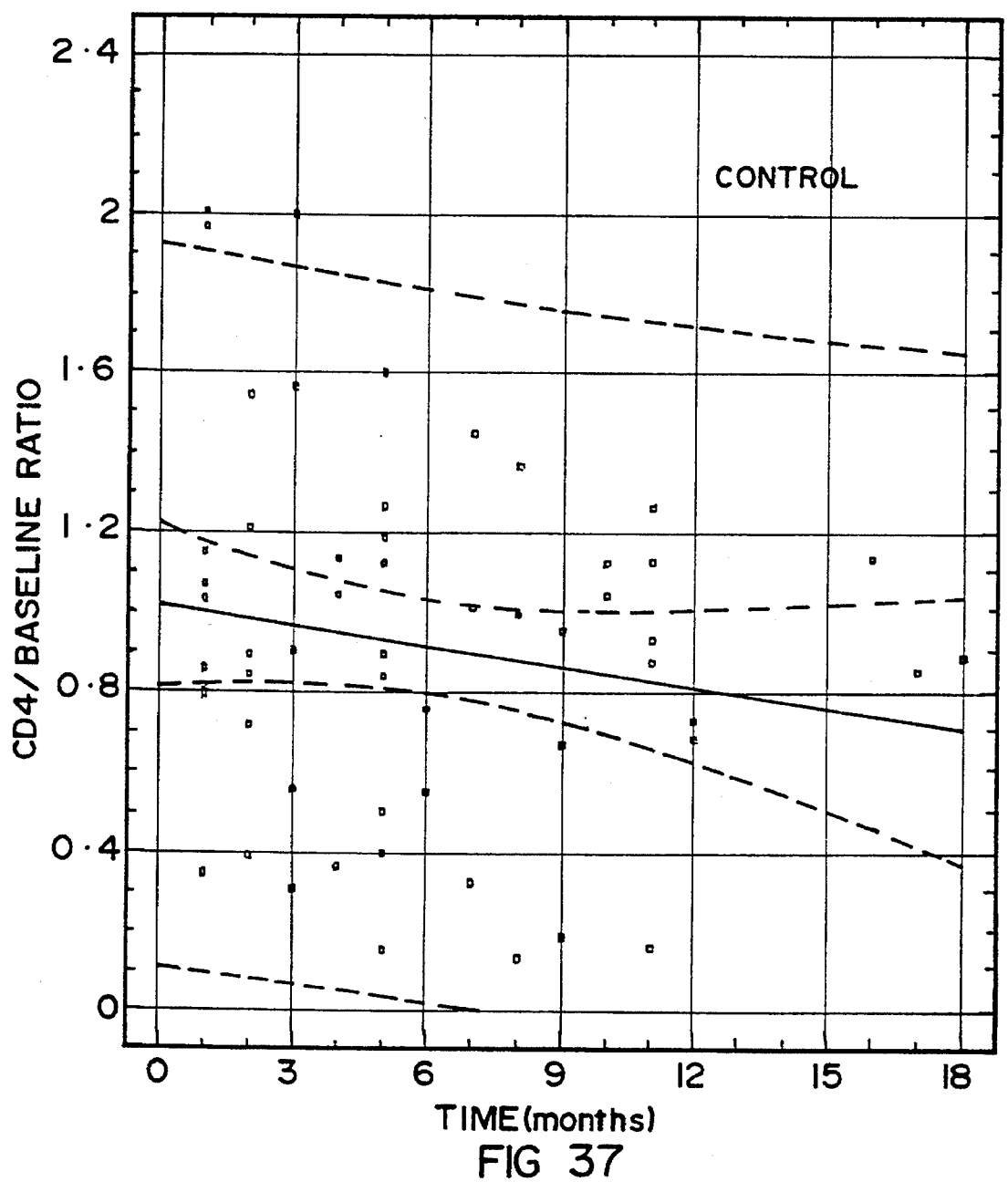

FIG. 37 depicts a regression analysis of the control data showing a plot, similar to that of FIG. 36, of CD4/baseline ratio as a function of time in months.

Figure 38:
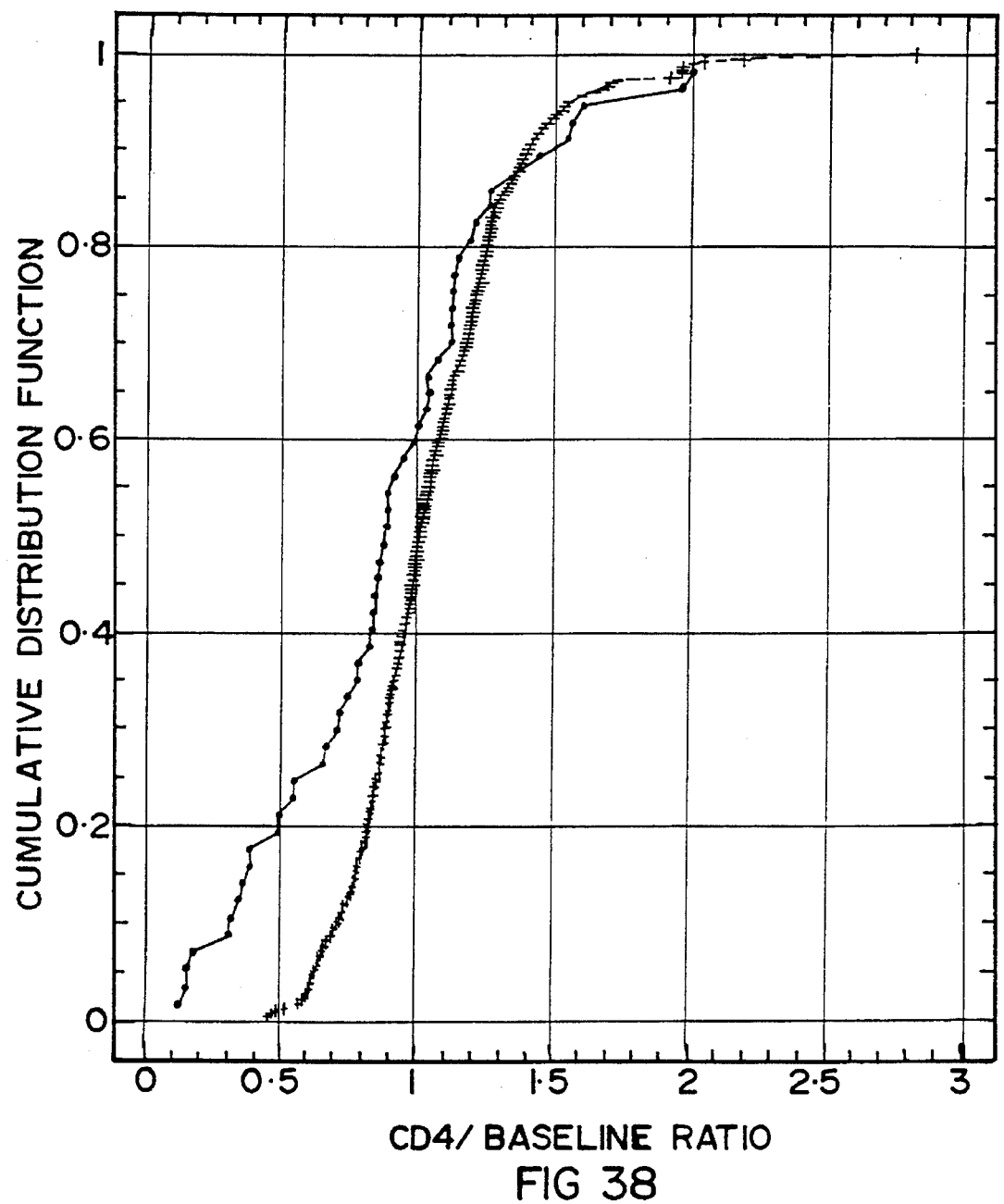

FIG. 38 shows a Kolmogorov-Smirnov plot of a cumulative distribution function as a function of CD4/baseline ratio.

Figure 39:
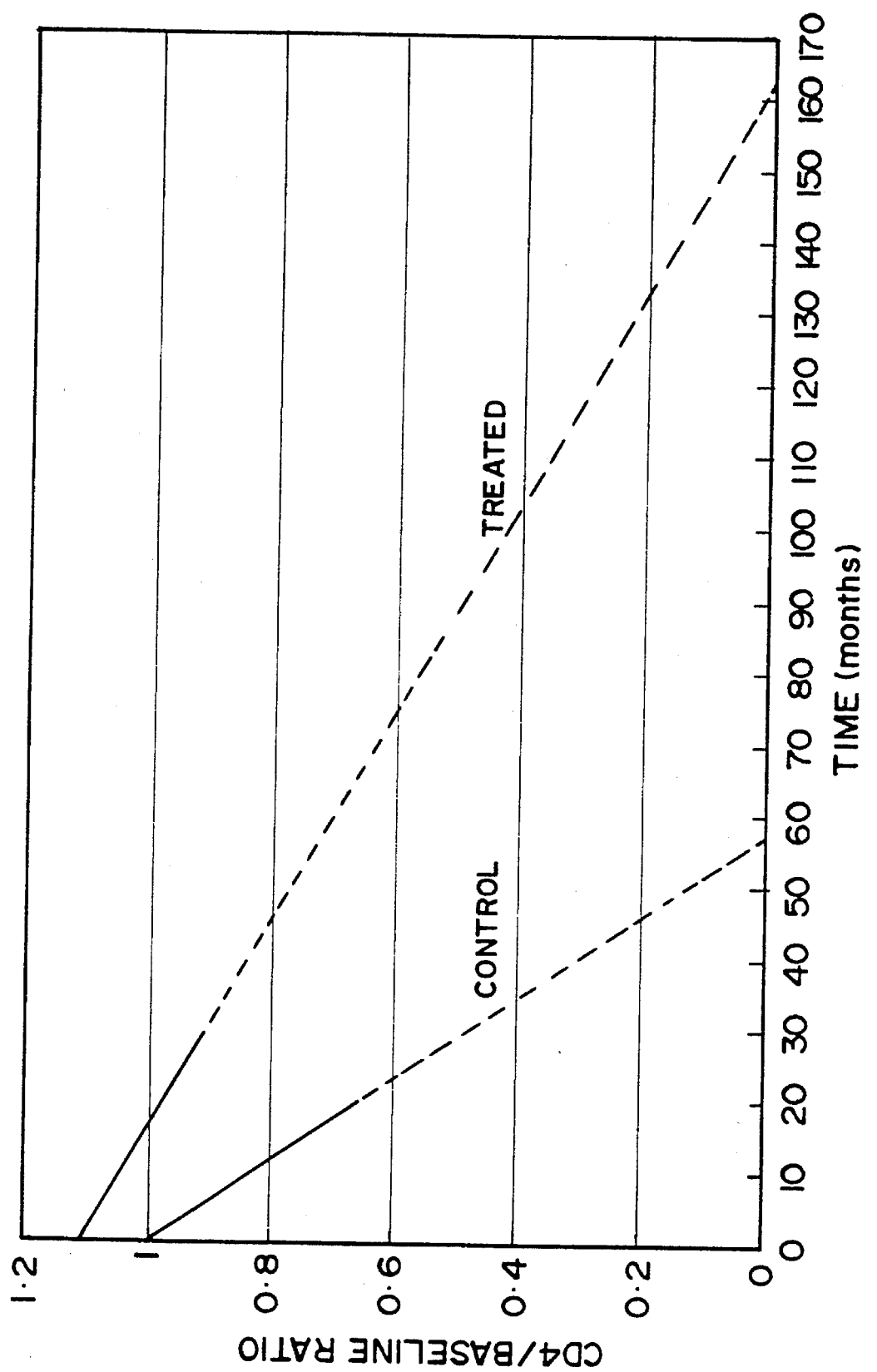

FIG. 39 shows extrapolated CD4/Baseline ratio as a function of time over a period of 162 months.

Figure 40A:
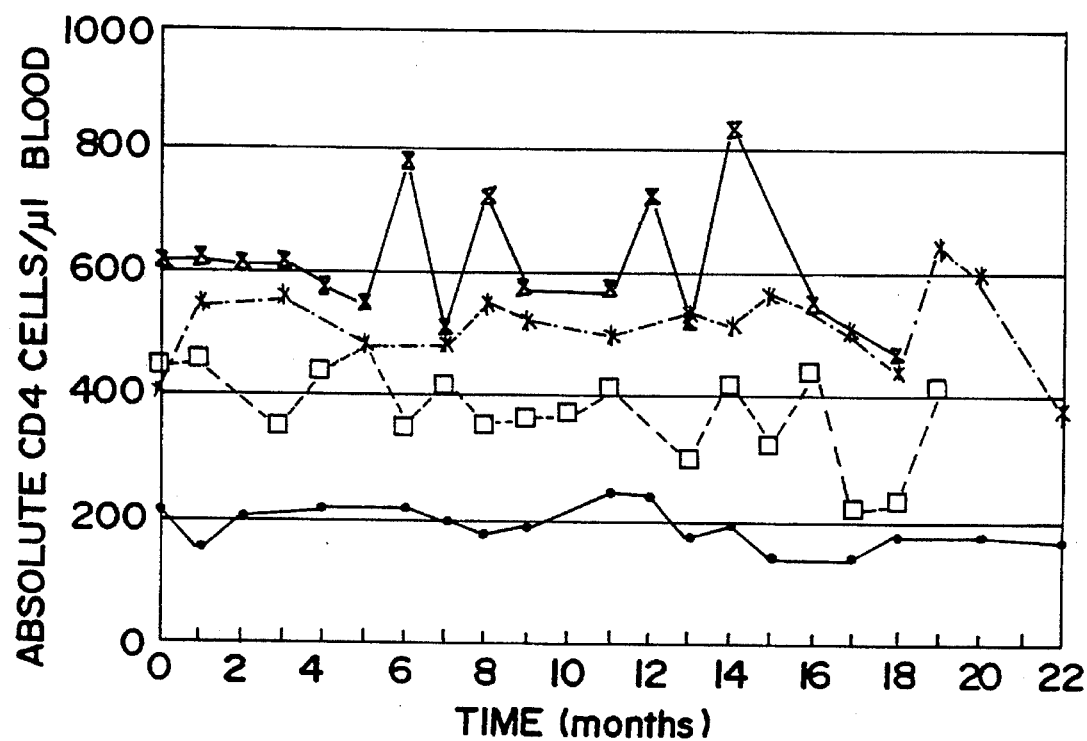
Figure 40B:
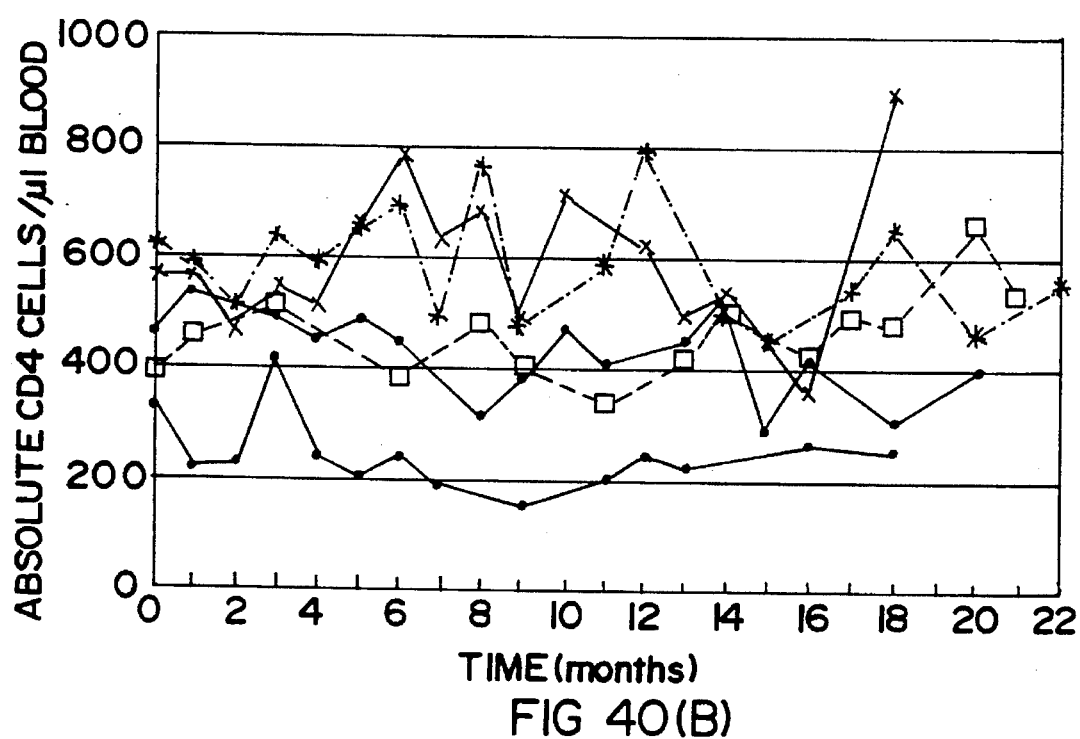

FIG. 40 shows two sets of plots of a longitudinal analysis of CD4 cell numbers in patients ingesting Hypoxoside containing plant extract and monitored for 18 months or longer.

Figure 41:
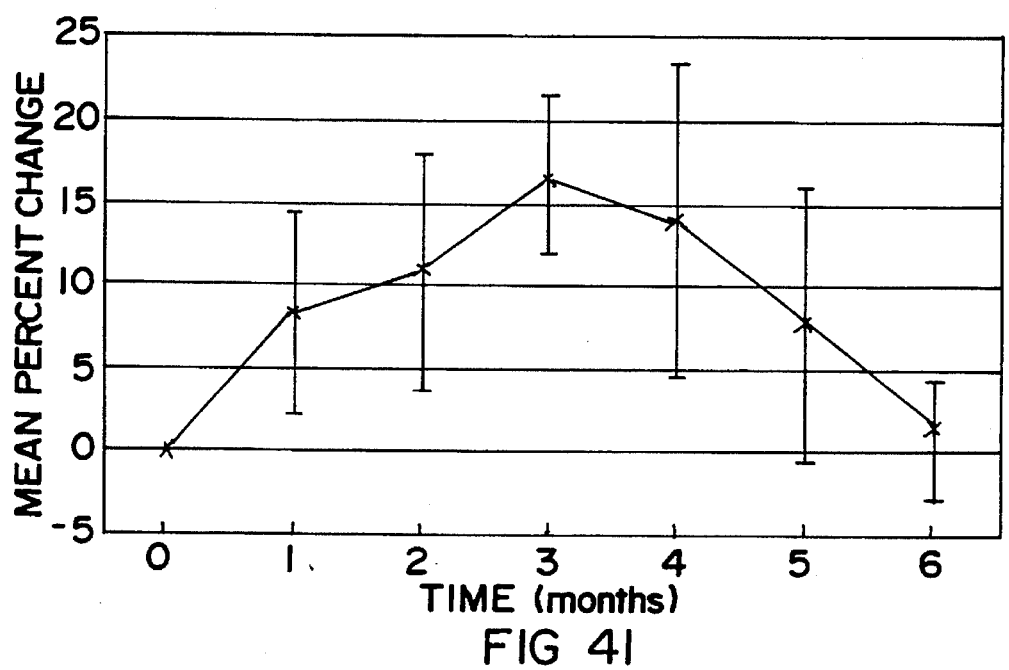

FIG. 41 shows the mean percent change in CD4 cell counts from baseline in the treated group, the percentages being calculated relative to the baseline value for all patients evaluable for a given internal and the vertical bars representing the SEM.

Figure 42:
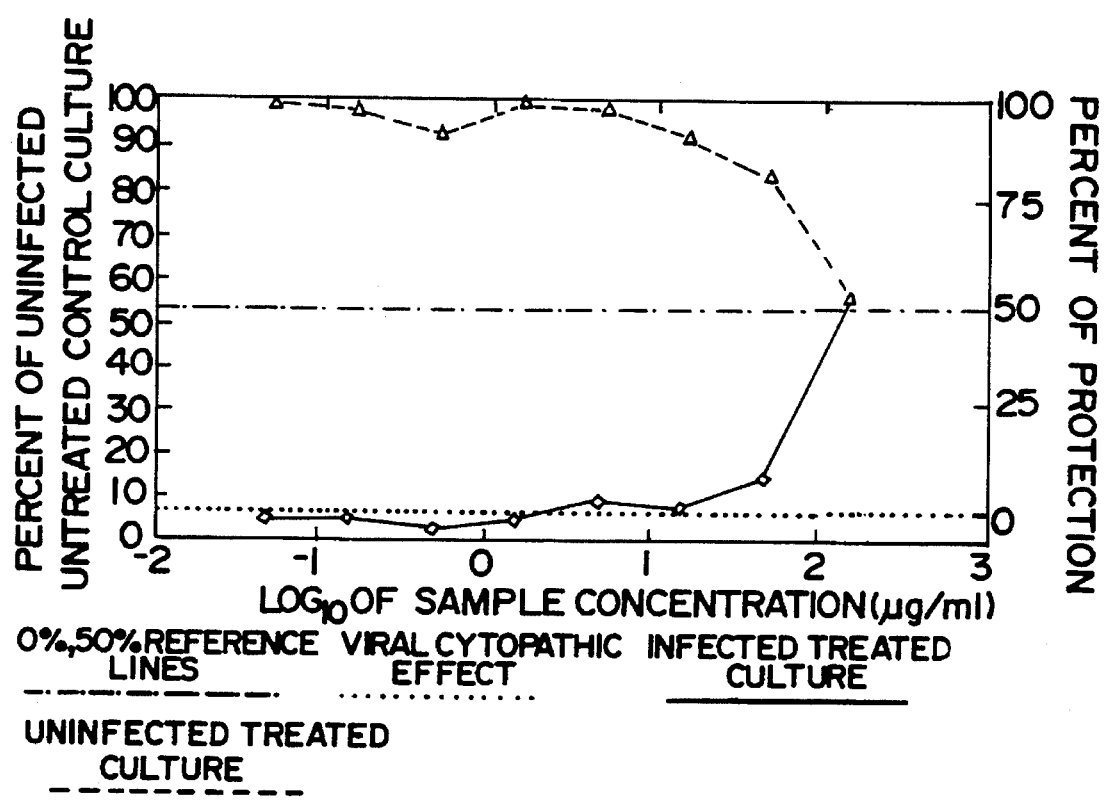

FIG. 42 shows a plot of percentage of uninfected untreated control culture and of percent of protection as a function of $\log_{10}$ of sample concentration for the in vitro anti HIV screening of compound XVII, cell line CEM-SS.

Figure 43:
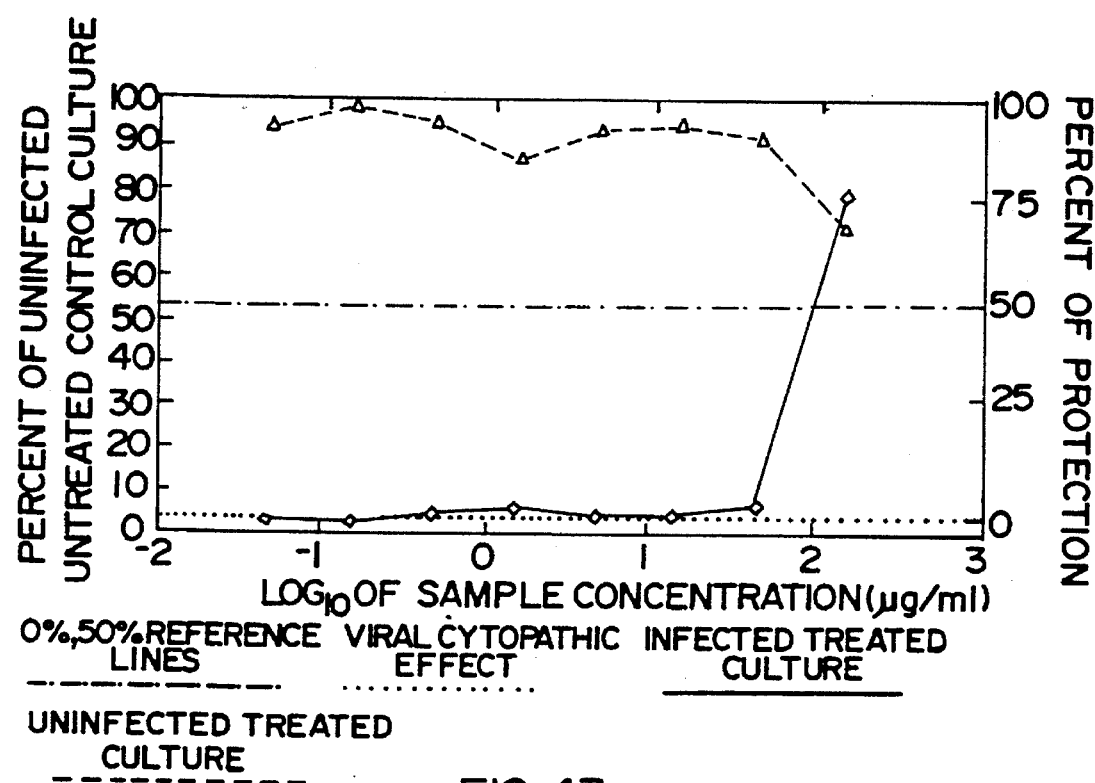
Figure 44A:
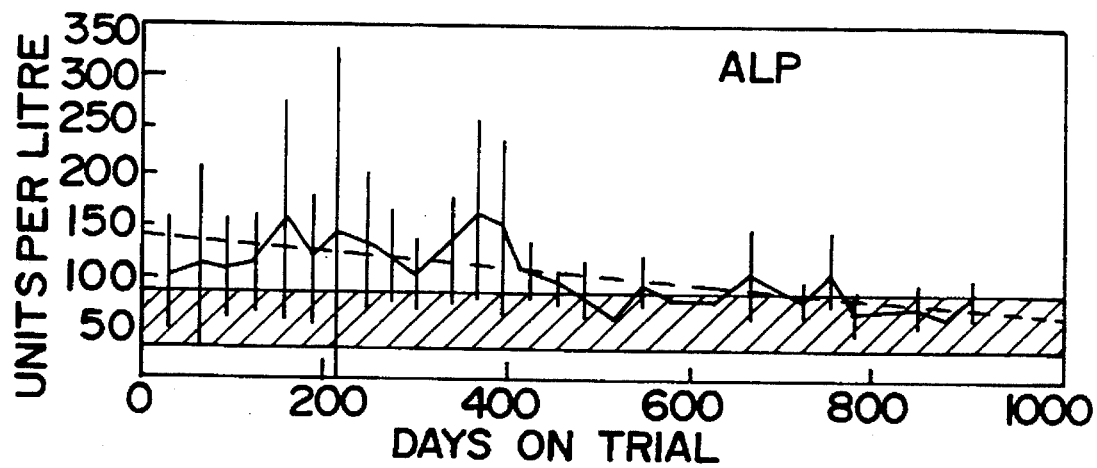
Figure 44B:
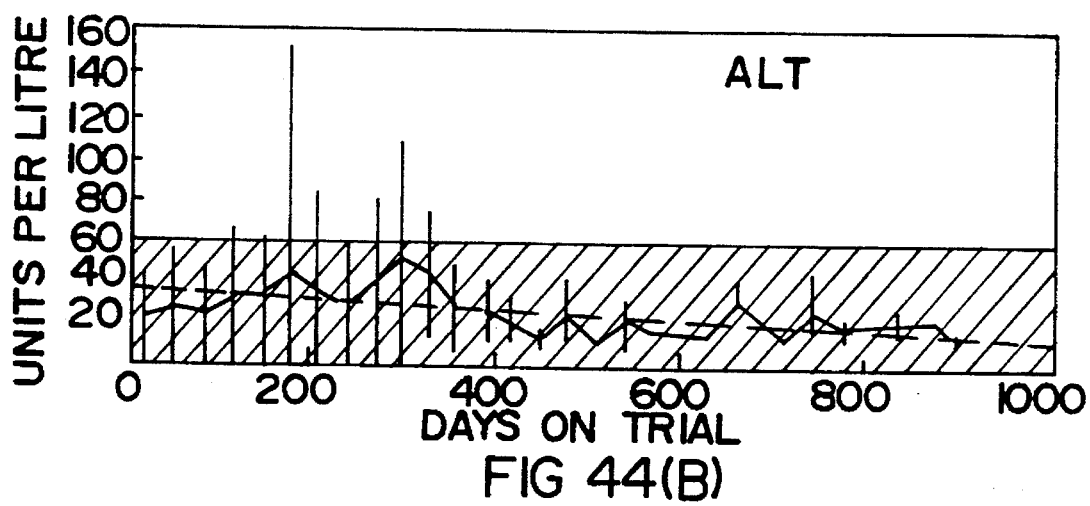
Figure 44C:
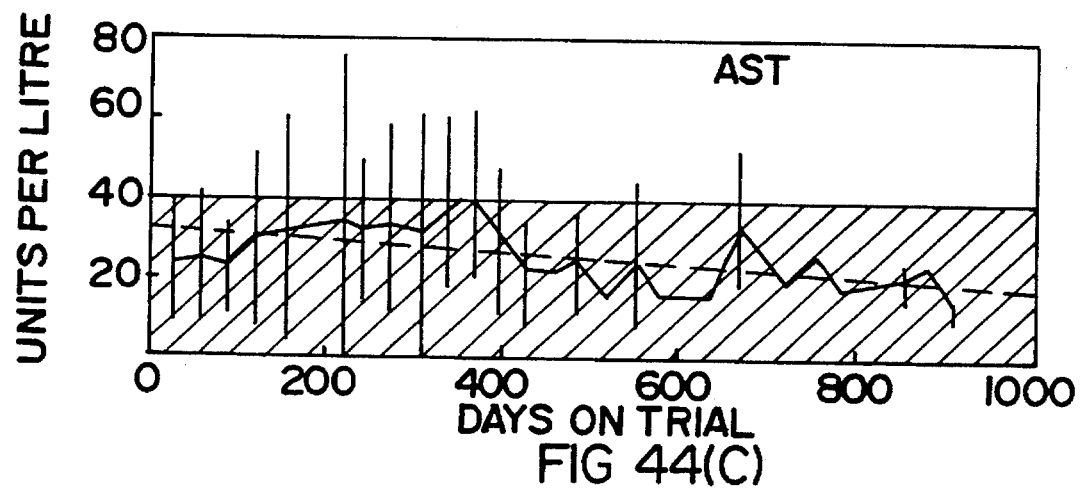
Figure 44D:
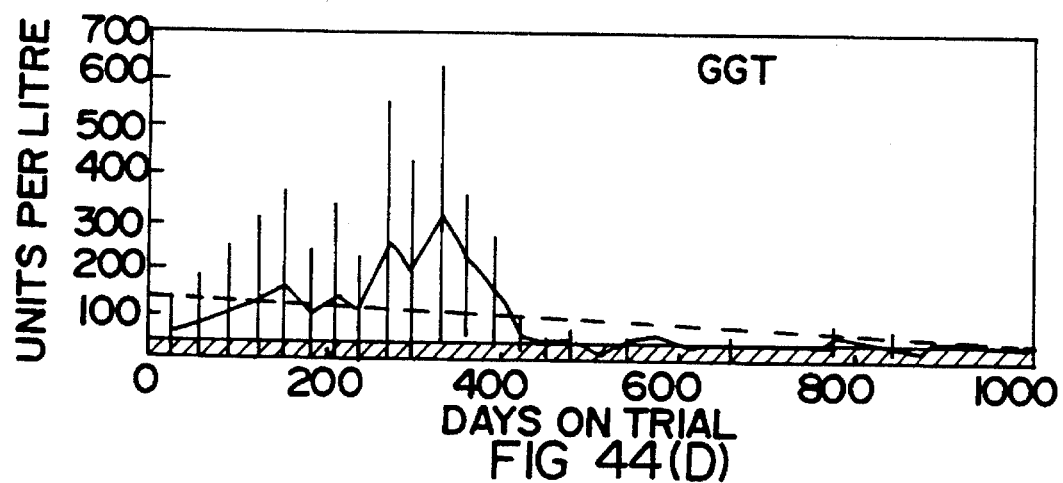
Figure 44E:
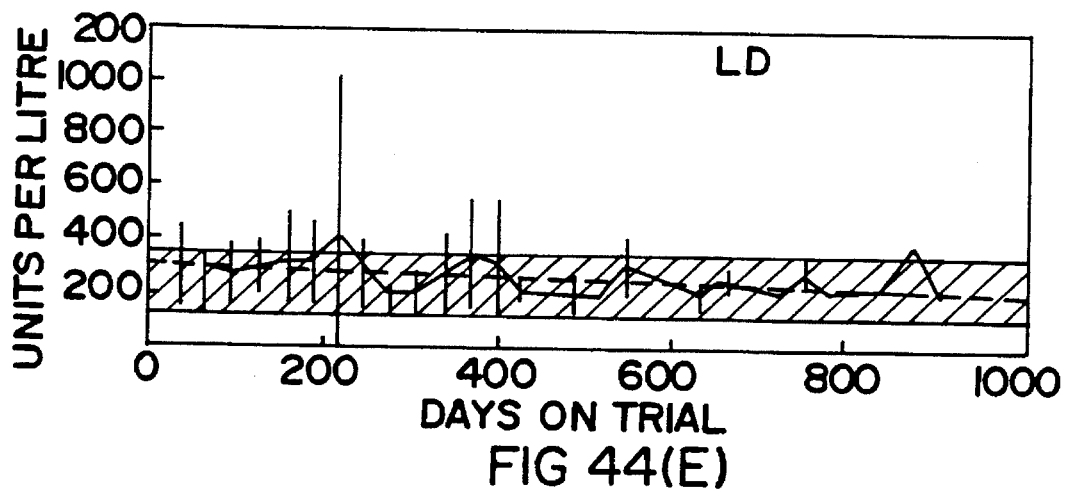
Figure 45A:
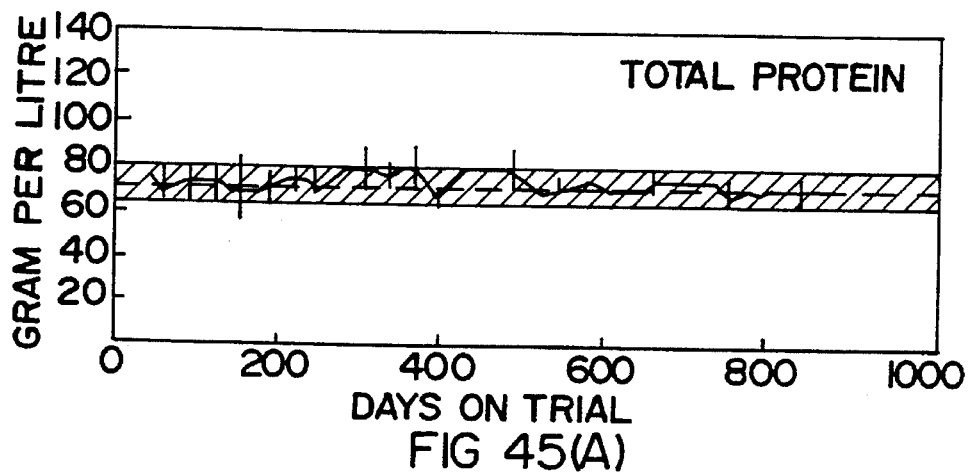
Figure 45B:
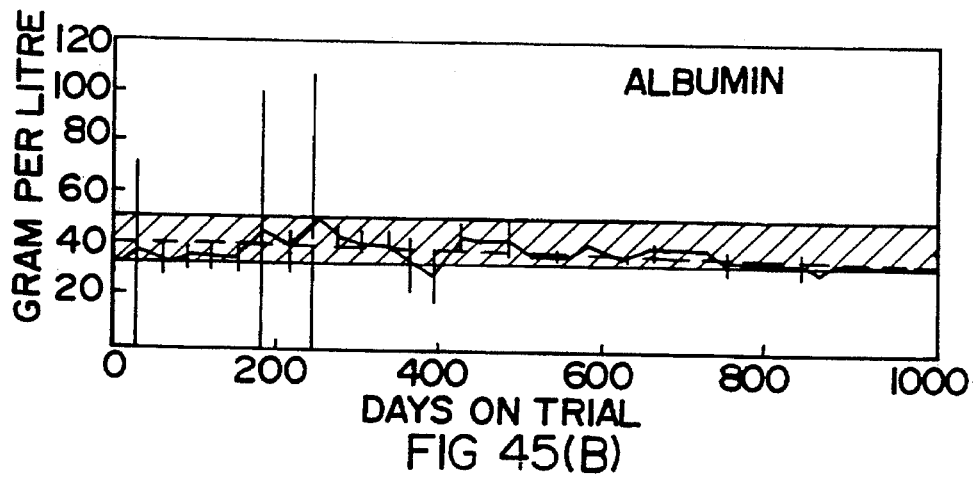
Figure 45C:
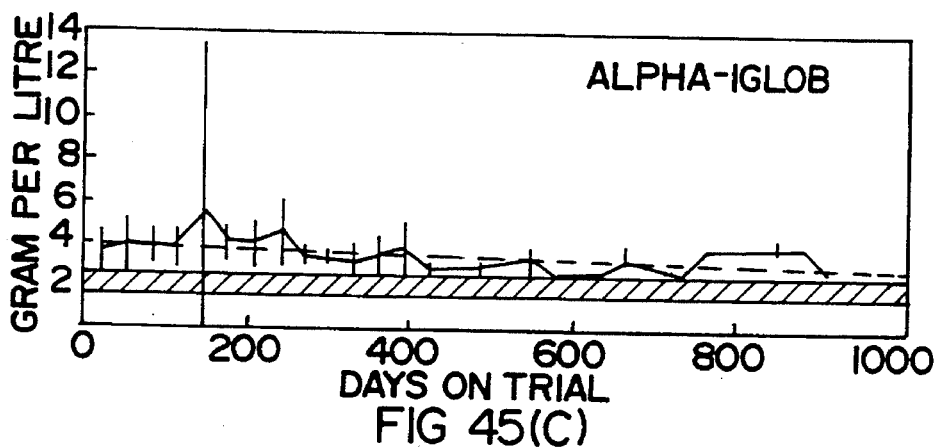
Figure 45D:
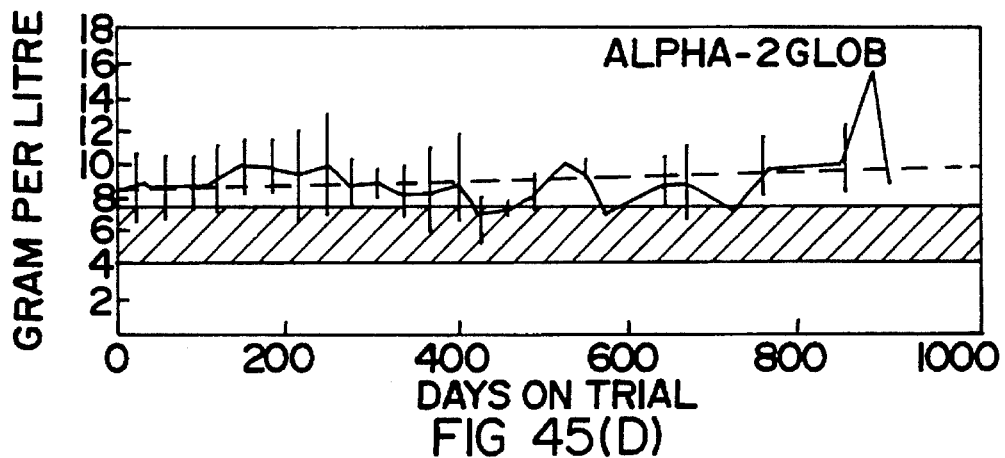
Figure 45E:
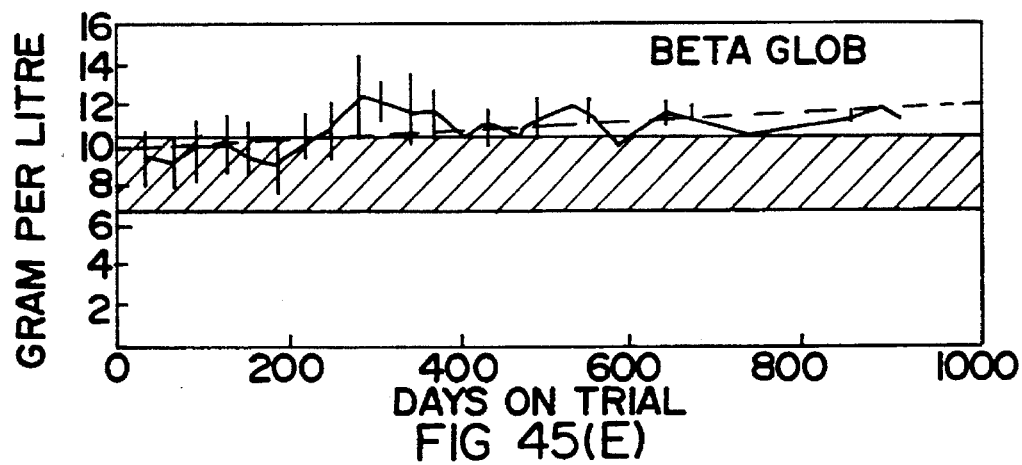
Figure 45F:
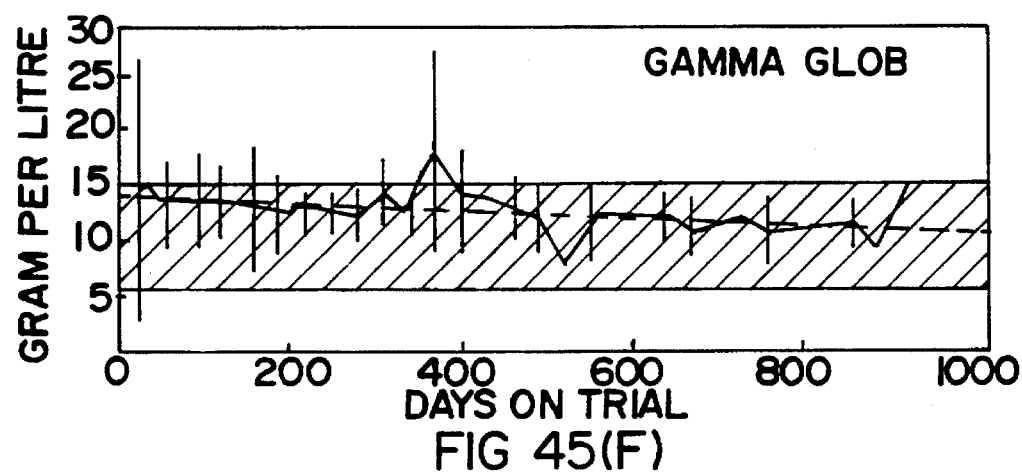
Figure 46A:
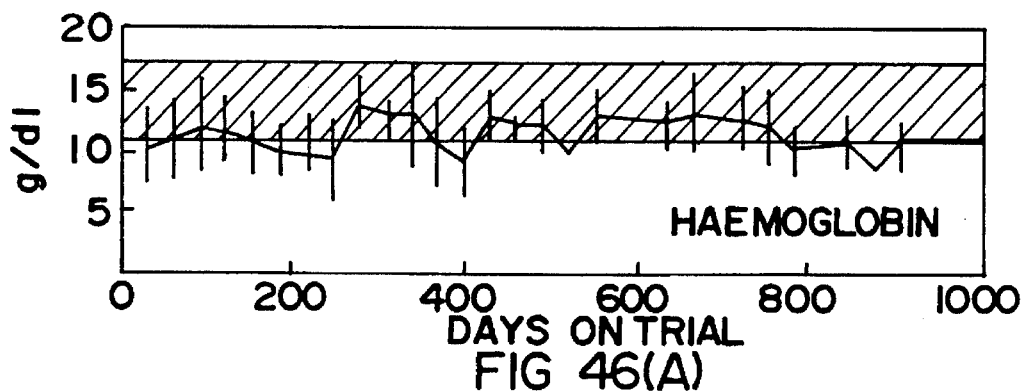
Figure 46B:
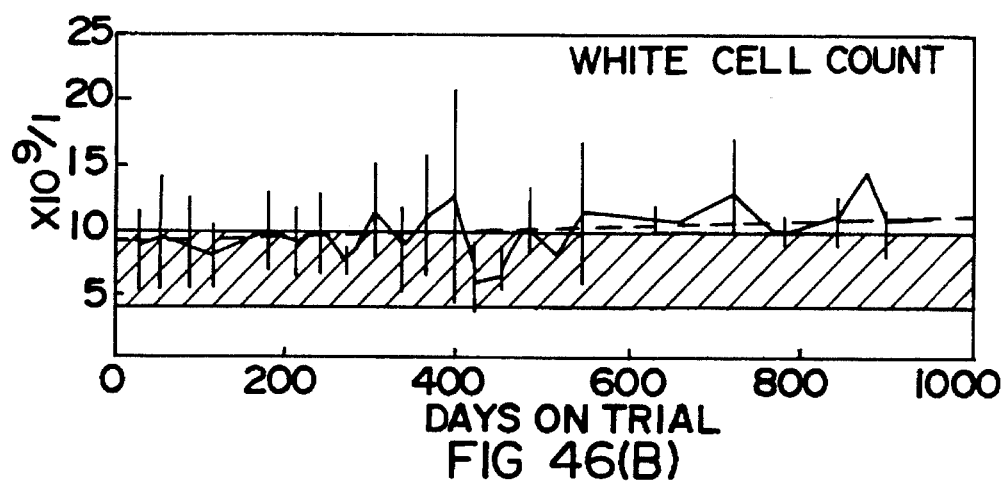
Figure 46C:
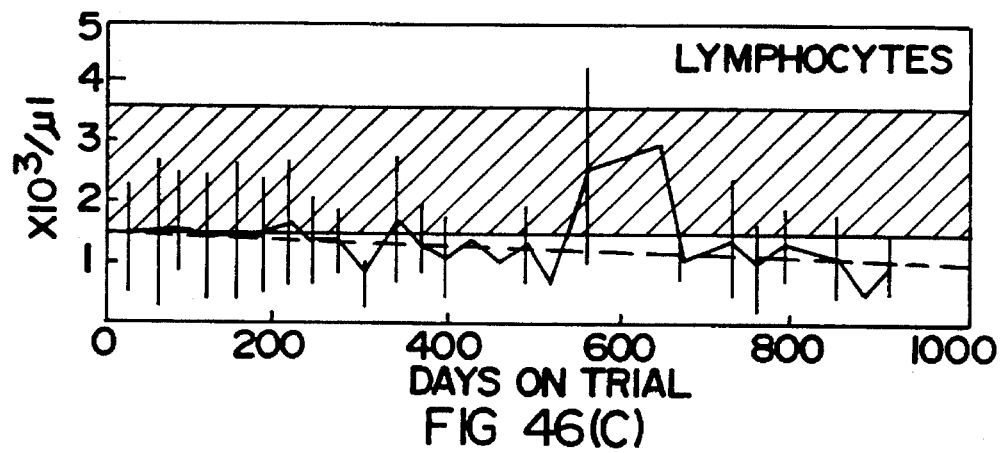
Figure 46D:
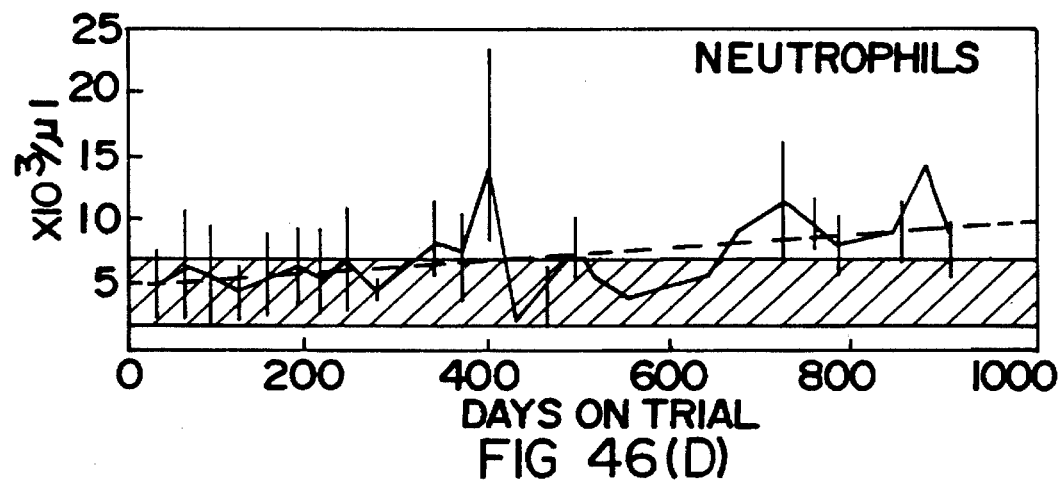
Figure 46E:
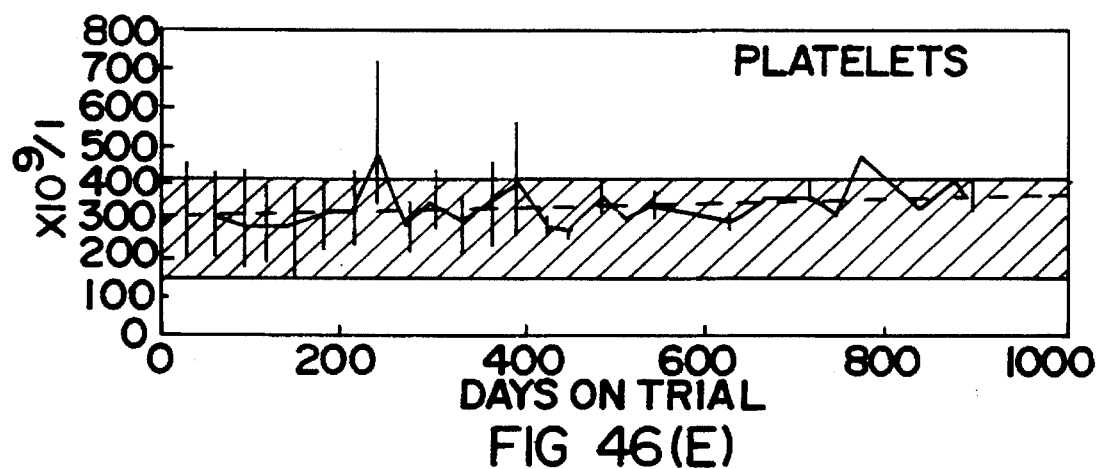

FIG. 43 shows a plot, similar to FIG. 42 for the cell line CEM-IW.

FIG. 44 shows plots of liver enzyme activity as a function of time, each point representing the average of all values obtained on a monthly basis with the standard deviation shown as a vertical bar, the dotted line representing a regression analysis of the trend and the shaded areas depicting the upper and lower normal limits for the population.

FIG. 45 shows serum protein concentrations in g/l as a function of time.

FIG. 46 shows plots, similar to those of FIG. 44, of haematological profile as a function of time.

Figure 47:
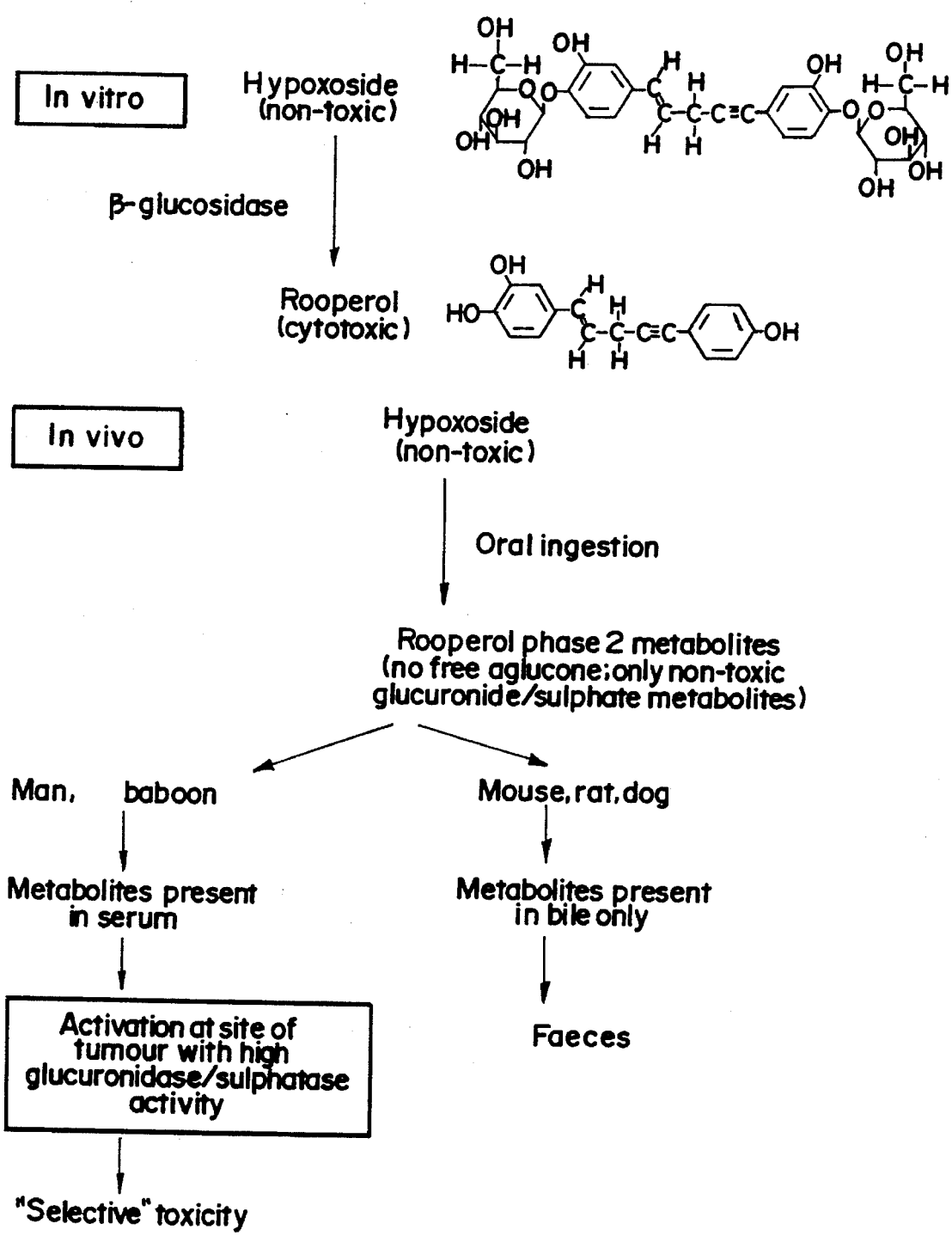

FIG. 47 shows, schematically, the functioning of hypoxoside as a non-toxic prodrug in cancer therapy.

DESCRIPTION OF THE PREFERRED EMBODIMENTS

EXAMPLE 1

Summary of the Method for the Analysis, Characterisation and Preparative Isolation of Compounds I–XXVIII Preparative Isolation of Compounds Preparative isolation of compounds was conducted by preparative High Performance Liquid Chromatography.

Equipment

A Shimadzu (Kyoto, Japan) instrument was used. It consisted of the following components: SCL-8A system controler, 2 x LC-8A mobile phase delivery pumps, SPD-6AV UV-Vis Spectrophotometric detector, FCV-130 AL reservoir inlet controler and FCV-100B traction collector.

The preparative column (50×300 mm) was packed with C8 bonded silica (Partisil Bioprep 20 µm C8 75A) obtained from Whatman (Fairfield, N.J., U.S.A.).

Operating conditions involved isocratic delivery of mobile phase (15% acetonitrile in water v/v) at a flow rate of 100 ml/minute. The detector was set to at 260 nm wavelength, and the fraction collector was set to collect 250 ml aliquots. Sample loading was conducted by dissolution of sample (5 g) in water (50 ml) which was pumped directly on-column, the column having been pre-loaded with water. Hypoxoside (compound V) and hypoxoside congeners [compounds (VII+VIII) and VI] were eluted in sequence starting at a retention volume of 8.5 l, providing fractions enriched with the respective compounds to a purity of 80–100% by mass.

Semi-preparative Isolation and Qualitative Analysis

A standardised High Performance Liquid Chromatography (HPLC) technique (Kruger et al: J. Chromatography, 1993, 612, 191–198) was applied to the analysis, characterisation and semi-preparative isolation of all the compounds I–XXVIII.

Equipment

A Hewlett Packard (Waldbron, Germany) instrument was used. It consisted of the following components:

HP1090M liquid chromatograph with a binary DR5 solvent delivery system and manual valve injector, HP1040 diode array detector, HP79994A work station, HP310SPU processor with colour monitor, HP9153C 20MB winchester disc drive, AP2225A thinkjet printer and HP7440A X-Y plotter.

The analytical column (4.6×250 mm) was packed with end-capped C8 bonded silica of 5 µm regular particle size (Whatman, Maidstone, England) while the guard column (2.1×75 mm) was packed with pellicular C18 bonded silica (Whatman). An in-line extraction pre-column (2.1×30 mm) as utilised was packed with preparative grade C18 bonded silica of 40 µm particle size (Analytichem International, Harbor City, Calif.).

Operating conditions involved a linear solvent gradient programmed at a flow rate of 1.5 ml/min starting with mobile phase A (0.05M $KH_2PO_4$) to which 10% v/v mobile phase B (acetonitrile-isopropanol 80:20 v/v) was added. This mixture was maintained for 1 minute after which a linear gradient of mobile phases A and B was formed which ended in 70% v/v of B after 16 minutes. Column temperature was maintained at 50° C.

The in-line extraction pre-column was loaded with a mixture of sample (dissolved in 50 μl of alcohol or in up to 200 μl of aqueous phase) and made up to 500 μl with an aqueous solution containing guanidinium (8.05M) and ammonium sulphate (1.02M). The extraction column was flushed before and after sample introduction by 500 μl of aqueous ammonium sulphate (0.5M). The solutes trapped on the in-line extraction column were then eluted onto the analytical column by the mobile phase upon initiation of the analysis.

Diode array detector parameters were programmed to monitor a signal at 260 nm and also to give an absorption spectrum from 200–400 nm.

EXAMPLE 2

Preparation of Dried Methanolic Extract of Hypoxis species

Washed Hypoxis species corms of H. rooperi, as described in Example 8, or of H. accuminata are shredded, the shreds placed on drying trays and dehydrated in a convection oven at 70° C. over 3.5 hours. The shreds are milled to 200 mesh fineness to provide a fine brown powder (12.5 kg of corms will provide approximately 5.0 kg of dried powder). The dried milled powder (5.0 kg) is extracted with methanol (25 l) at room temperature and with stirring over 30 minutes. Filtration of the slurry and vacuum evaporation of the clear brown solution provides 1.25 kg of the light brown Hypoxis species corm extracts which consistently contain between 45–50% m/m of hypoxoside and its congeners [compounds V–VIII) of which hypoxoside (compound V) is the major (90–95% m/m] component.

EXAMPLE 3

Figure 2:
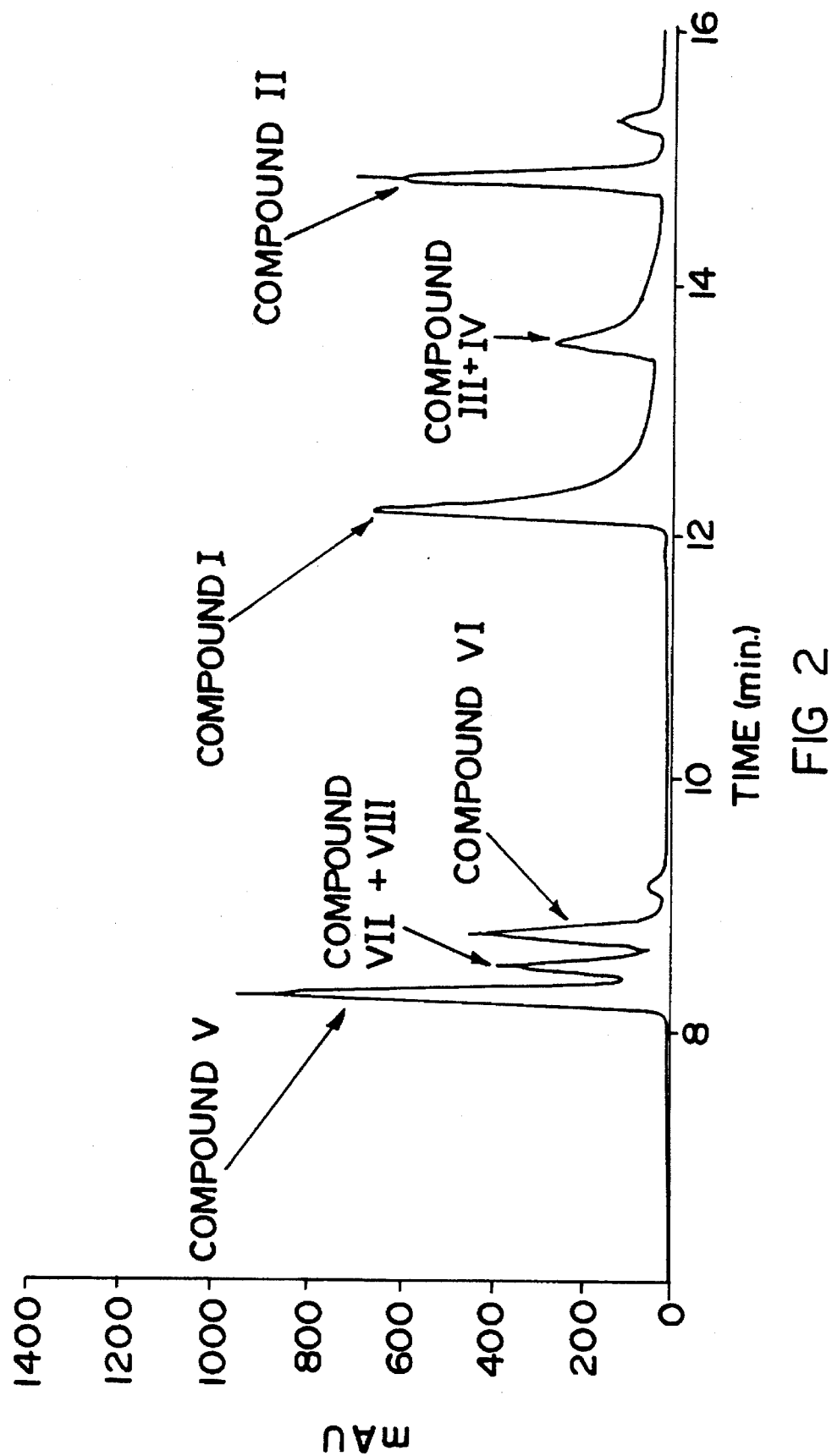
FIG. 2 shows a chromatogram, similar to FIG. 1, of an ethanolic extract of compounds V–VIII from corms of *H. latifolia*, to illustrate the relative amounts of compound V, compound VI and compounds (VII+VIII) in the extract, the respective aglucones, obtained by enzymic deglucosidation of compounds V–VIII, namely compounds I–IV respectively, being cochromatographed for comparative purposes, retention times being.

Preparation Isolation of Compounds V–VIII (see FIGS. 1–2)

Compound V was isolated from a methanolic extract of Hypoxis rooperi, which was then purified by preparative HPLC as described in Example 1 (see FIG. 1).

Compounds VI and (VII+VIII) were isolated from an ethanolic extract of Hypoxis latifolia, which was then purified by preparative HPLC as described in Example 1. Further purification of these compounds was conducted where necessary by semi-preparative HPLC using the standardised analytical HPLC system described in Example 1 (see FIG. 2).

EXAMPLE 4

Isolation of Compounds I–IV (see FIG. 2)

Compounds I, II and (III+IV) were isolated as the enzymatic hydrolysis products of compounds V, VI and (VII+VIII) respectively as follows:

Compounds V, VI and (VII+VIII) (100 mg of each) were separately dissolved in aqueous acetate buffer (10 ml, 0.1M, pH 5.5) and to each was added β-glucosidase (100 mg). The mixtures were incubated for 4 hours at 37° C., after which the hydrolysis products were extracted with diethyl ether (5 ml). The diethyl ether was washed with aqueous sodium bicarbonate (5 ml, 0.5M) and then dried with anhydrous sodium sulphate. The ether phase was evaporated under a stream of nitrogen gas to yield 5–10 mg of compounds I, II and (III+IV) respectively. Each product was purified by semi-preparative HPLC using the standardised analytical HPLC system described in Example 2. Removal of the HPLC solvent buffer salts from the HPLC fractions was achieved by the standard reverse phase sorption technique and the final powdered products of each obtained by lyophylisation.

EXAMPLE 5

Isolation of Compounds XIII–XXVIII (see FIGS. 3–12)

A methanolic extract of the corms of Hypoxis rooperi was purified by preparative HPLC (see Example 1) to yield a mixture containing mainly compound V (90–95% m/m), and to a lesser extent compounds VI and (VII+VIII) (see FIG. 3). This product (1 g) was dissolved in water (200 ml) and ingested orally as a single dose by an adult male subject. Urine was subsequently collected and treated as follows:

C18 bonded silica sorbent material (200 g, 40 μm) was pre-treated with methanol and water via a column bed. Filtered urine (5 l) was passed through the sorbent bed followed by elution in sequence with water (400 ml), aqueous methanol (10% v/v, 400 ml), aqueous methanol (30% v/v, 800 ml) and finally with methanol (400 ml) and followed by water (400 ml).

The aqueous methanol fraction (30% v/v, 800 ml) was diluted with water (1600 ml) and again passed through the sorbent bed which was then eluted with water (400 ml) and finally with methanol (400 ml).

The final methanol solution was evaporated under vacuum at 50° C. to an aqueous residue which was lyophylised to yield a mixture of metabolites XIII–XXVIII and endogenous urine components (1 g). A suitable volume of filtered aqueous solution of this residue (10 mg/ml) was injected on to the in-line pre-column of the standardised HPLC system (see Example 1) such that fractions A,B and C (see FIGS. 5–6) were collected at the column outlet. These tractions were rendered tree of mobile phase buffer salts by the standard reverse phase sorption technique and lyophylised to dry products, representative of mixtures of compounds XIII–XXVIII.

EXAMPLE 6

Chemical Synthesis of Sulphate Conjugates

Pyridinium sulphate was used as a sulphating agent in the partial synthesis of compounds IX–XII and compounds XVII–XX.

Preparation of Pyridinium Sulphate Reagent

To a mixture of dry ethyl acetate (1 l) and concentrated sulphuric acid (25 l, 0.469 mol) was added slowly, with stirring, dry pyridine (50 ml, 0.620 mol). The mixture was cooled and the precipitate of pyridinium sulphate produced was separated from the ethyl acetate by decanting, rinsed with a portion of dry ethyl acetate and vacuum dried at 60° C. to yield 85 g (100% yield) of product. The product (85 g, 0.480 mol) was dissolved in dry dimethylformamide (250 ml) to provide a 1.921M pyridinium sulphate solution, herein designated as pyridinium sulphate reagent. The reagent was stored in a hermetically sealed amber bottle over anhydrous calcium sulphate (25 g).

Per-Sulphation of Hypoxoside (Compound V) and Hypoxoside Congeners, [Compounds VI and (VII+VIII)] to Produce Compounds IX, X and (XI+XII) Respectively.

To a solution of hypoxoside (2 g, 0.0033 mol) (see Example 3 and FIG. 1) in dry dimethylformamide (130 ml) was added pyridinium sulphate reagent (70 ml, 0.135 mol), anhydrous calcium sulphate (4 g) and acetic anhydride (13.2 ml, 0.14 mol), and the mixture stirred under nitrogen atmosphere at 25° C. for 24 hours. The reaction mixture was filtered to a clear solution to which was added, with stirring, a mixture of methanol and 2-propanol (600 ml, 1:2 v/v ratio), followed by 2-propanol (250 ml). The precipitate so formed was congealed by continued stirring and the solvent mixture removed by decanting. The congealed precipitate was rinsed with 2-propanol and then dissolved in water (40 ml). To this solution was added with stirring methanol (100 ml) followed by a solution of sodium hydroxide in methanol (50 ml, 1M) to obtain a pH of 7–11. The precipitate so formed was isolated by filtration, washed with methanol, and dissolved in water (200 ml). This solution was passed through a C18-bonded silica sorbent particle bed (40 μm particle size, bed size: internal diameter 50 mm, length 50 mm) which had been preconditioned with methanol and water. A further 200 ml of water was passed through the sorbent bed and combined with the previous eluate, to provide 400 ml of clear sodium salt of hypoxoside sulphate solution. This solution was found to be capable of being lyophylised to a dry white product (2 g). It was also found that the sodium salt of hypoxoside sulphate could be precipitated from the eluate by the addition of ethanol (400 ml) together with ethyl acetate (1,200 ml). The precipitate could be collected by filtration and dried under vacuum to provide a dry white product. The sodium salt of hypoxoside sulphate was readily soluble in water, and, unlike hypoxoside (i.e. compound V), had little or no affinity for a reverse phase chromatography medium such as C18-bonded silica particles, even in the presense of water. Compounds VI and (VII+VIII) were per-sulphated in a similar manner.

Sulphation of Compounds I, II and (III+IV) to Produce Compounds XVII, XVIII, and (XIX+XX) Respectively.

To a solution of compound I (100 mg, 0.00355 mol) (see Example 4 and FIG. 2) in dry dimethyl formamide (2.2 ml), was added pyridinium sulphate reagent (1.5 ml, 0.00288 mol), and acetic anhydride (0.3 ml, 0.00318 mol). The mixture was allowed to stand under anhydrous conditions at 90°–100° C. for 30 minutes, cooled and then poured into cold water (40 ml) while stirring. The solution was then passed through a C18-bonded silica sorbent bed (4 g, 40 μm particle size) which had been pre-treated with methanol and then with water.

The following were then passed through the sorbent bed in sequence, water (40 ml), aqueous sodium bicarbonate (40 ml, 0.1M), water (40 ml) and methanol (10 ml) which methanol was separately collected. The methanol eluate was evaporated under vacuum at 50° C. to an aqueous residue which was lyophilised to yield 0,07 g of compound XVII. Compounds XVIII and (XIX+XX) were prepared by the same procedure from compounds II and (III+IV) respectively.

EXAMPLE 7

Chemical Synthesis of Compound XIII (see FIG. 13)

Compound XIII was derived by the glucuronidation of compound I. The di-β-D-glucuronide of compound I was derived by the classical Koenigs-Knorr reaction, involving the coupling of a protected bromo-glucuronide to the aglycone in the presence of silver carbonate.

The protected bromo-glucuronide, namely methyl (2,3,4-tri-O-acetyl-α-D-glucopyranosyl 1-bromide) uronate, was prepared according to the method described by Bollenback et al: J. Amer. Chem. Soc., 1955, 77, 3310–3315.

The product was not preparatively isolated in view of the trace yield, but was characterised as described in Example 8 hereunder.

EXAMPLE 8

General Procedure for Characterisation of Compounds by the Standardised HPLC Procedure and Enzyme Hydrolysis (see Example 1)

The characterisation of the compounds is based on their absolute chromatographic retention times, their retention times relative to one another, and on their diode array detector absorption spectra as obtained under the standard analytical parameters. Retention times have been found to be reproducible to within limits of about 30 seconds on a range of analytical columns from the same manufacturer. Diode array detector absorption spectra are presented within the limits of resolution of the detector, and the absorption maxima and minima are stated as a wavelength range, ranging from 4–6 nm.

Benzene is used as a reference compound. The analysis of benzene in methanol is characterised as follows with respect to the standardised HPLC method.

| Retention time = | 13.84 minutes |
|---|---|
| Absorption maxima = | 198.5–202.5 nm |
|  | 252.5–256.5 nm |
| Absorption minima = | 220.5–224.5 nm |

Further characterisation of compounds XIII–XXVIII is deduced on the basis of selective enzyme hydrolysis with β-glucuronidase and aryl sulphatase. D-saccharic acid 1,4-lactone (Sigma 50375)(1 mg/ml) and sodium sulphate (0.01M) were used for the selective inhibition of β-glucuronidase and aryl sulphatase activity respectively where cross reactivity was found in commercial enzyme preparations. Hydrolysis was conducted in acetate buffer (0.1M pH 5.5).

Characterisation of Compounds I–VIII (see FIGS. 1–2 and FIGS. 14–22)

An aqueous solution of compound V (see Example 3) prepared from the methanol extract of *Hypoxis rooperi* (see Example 2) was analysed by the standard HPLC method (see Example 1). Compound V (see FIG. 1) was isolated as a major component at a retention time of 8.25 minutes, with UV maxima respectively at 210.5–212.5; 254.5–258.5 and 288.5–292.5 nm (see FIG. 17). Values quoted by Marini-Bettolo et al: Tetrahedron, 1982,38, 1683–1687, are UV maxima respectively at 258, 291, 298 and 310 nm as measured in methanol. Compound V underwent irreversible reaction with alkali and gave a positive reaction for phenolic groups with ferric ferricyanide. Compounds VI and (VII+VIII) are more prevalent in the ethanolic extract of *Hypoxis latifolia* and are therefore better characterised in the isolate obtained from *Hypoxis latifolia* (see FIG. 2).

Similarity of the UV spectra of compounds VI and (VII+VIII) to the spectrum of compound V (see FIGS. 17–19) suggests that they are structuraly related to compound V.

Hydrolysis of compounds V, VI and (VII+VIII) by β-D-glucosidase at pH 5.5 yields compounds I, II and (III+IV) respectively, as illustrated in FIG. 2.

The order of elution of compounds V, VI and (VII+VIII) and their aglucones, compounds I, II and (III+IV) respectively remains the same (see FIG. 2). From this it is deduced that compounds V, VI and (VII+VIII) differ from each other with respect to substituents on their aglucones. Therefore an increase in the retention time from compound V to compounds (VII+VIII), and then to compound VI and increase in retention time from compound I, and to compounds (III+IV), and then to compound II respectively, will be consistent with a decrease of the number of hydroxyl groups on the aglucones.

Compound II as derived from *Hypoxis latifolia* was compared with E-1,5-bis(4'-hydroxyphenyl)pent-4-en-1-yne as synthesised by Drewes et al: Phytochemistry, 1989, 28, 153–156 with regard to retention time and spectral characteristics coincidence (see FIGS. 23–24) confirming the existence of the di-para-hydroxyl groups of compound II.

Compounds (III+IV) with a retention time intermediate to those of compounds I and II are inferred as having three hydroxyl groups, possible structures being represented by compound III and compound IV, but not yet chromatographically resolved (see FIG. 2). The most likely configuration of the tri-hydroxy compound as derived from *Hypoxis rooperi* will be that of compound III since Drewes et al: Phytochemistry, 1989, 28, 153–156 provide good evidence that the phenolic ring on the alkene side is a catechol when the compound is derived from *Hypoxis rooperi*.

Spectral characteristics of compounds I–VIII as illustrated in FIGS. 14–22 respectively are consistent with a common central pent-4-en-1-yne structure.

The comparative spectra (see FIGS. 20–22) show that deglucosidation results in a shift to shorter wavelength, under prevailing analytical conditions.

Retention shifts brought about by hydrolysis and degree of hydroxylation of these chemical derivatives are predictable in terms of reverse phase chromatography retention mechanism.

Characterisation of Compounds IX, X and (XI+XII) (see FIGS. 25–26)

Partial sulphation of compounds V–VIII would result in a large number of hydroxy sulphates, giving a complex elution pattern. However, in the case of total sulphation, three well-defined elution peaks can be expected for each compound. A distinct three-peak pattern is indeed perceptible in FIG. 25 and compounds IX, X and (XI+XII) are therefore regarded as the deca-, octa- and nano-sulphates of compounds V, VI and (VII+VIII) respectively. Partial sulphation products have however been prepared by reducing the molar proportion of the sulphating reagent relative to the compound which is sulphated, and complex elution patterns, as expected, were observed.

Compounds IX, X and (XI+XII) are not readily distinguishable in terms of their chromatographic or spectral properties, and a mixture of these compounds is characterised in FIGS. 25 and 26. Early elution of these compounds (see FIG. 25) is consistent with their enhanced water solubility, while they retain the spectral characteristics of compounds V–VIII. It is expected that compounds X and (XI+XII) as prepared by the method in Example 6 will have a similar degree of sulphation to compound IX.

Characterisation of Compounds XII–XXVIII (see FIGS. 3–12 and 27–32)

Compounds XIII–XXVIII represent the products of biotransformation of compounds V–VIII. They are found in the serum and urine of human subjects after the ingestion of compounds V–VIII (see FIGS. 4–6). It will be noted from the following observations that certain qualitative and quantitative biochemical events are relevant to the in vivo formation of conjugate compounds XIII–XXVIII. This together with confirmation of conjugate type by synthesis and specific enzyme hydrolysis will serve to identify and characterise these compounds.

Compounds V–VIII have been shown to be hydrolysed in the intestinal tract of human subjects to compounds I–IV, since these aglycones have been detected in human faeces. Compounds I–IV therefore, after absorption from the intestinal tract, are the likely metabolic precursors of compounds XIII–XXVIII.

From FIGS. 3 and 27 it will be noted that the relative amounts of compounds V–VIII are representative of the relative amounts of their hydrolysis products, namely compounds I–IV. The relative amounts of compounds I–IV shown in FIG. 27 therefore are representative of the relative amounts of these aglucones that are available for intestinal absorption.

Isolation of urine metabolites by HPLC into fractions A,B and C is illustrated in FIG. 6, and the absorption spectra characteristic of compounds I–VIII are retained in the metabolite fractions (FIGS. 7–9). This verifies that the urine metabolite fractions A,B and C have a common origin, namely compounds I, II and (III+IV).

Complete hydrolysis of metabolite fractions A,B and C by β-D-glucuronidase and aryl-sulphatase at pH 5.5 result in their aconjugate profiles (see FIGS. 10–12). The retention times and absorption spectra of compounds I, II and (III+IV) remain the same, whether they are the products of hydrolysis of plant extracts or of urine metabolite extracts. This re-affirms the type of the conjugate groups: β-D-glucuronates and sulphates of the plant aglucones, namely compounds I, II and (III+IV).

Selective enzymatic hydrolysis of fractions A,B and C (see FIG. 6) suggests that:

i) Fraction A consists primarily of the di-β-D-glucuronides of compounds I–IV, namely compounds XII-I–XVI respectively.

ii) Fraction B consists primarily of the mono-sulphate-mono-β-D-glucuronide of compounds I–IV, namely compounds XXI–XXIV respectively.

iii) Fraction C consists primarily of the di-sulphates of compounds I–IV, namely compounds XVII–XX respectively.

Thus the type of the conjugate group seems to be the principal determinant of the retention time of the metabolites in reverse phase chromatography. It is appropriate therefore that Fraction B, the mixed conjugate (that is the mono-β-D-glucuronate mono-sulphate) of compounds I, II and (III+IV), should be intermediate in retention time between their di-β-D-glucuronates (Fraction A) and their di-sulphates (Fraction C).

The aconjugate profiles of urine fractions A,B and C (see FIGS. 10–12) do not contain the same relative amounts of compounds I–V as the material ingested, (see FIGS. 3 and 27) suggesting selective absorption of compounds II and (III+IV) over compound I, and/or suggesting the biotransformation of compound I to compounds (III+IV) and then to compound II, with subsequent conjugation.

The chemical sulphation of compound I (see FIGS. 28–29), compound II (see FIGS. 30–31) and a mixture of di-sulphated compounds I–IV (see FIG. 32) result in products with retention times in the region of the retention time of urine metabolite Fraction C (see FIG. 6) shown by the action of aryl-sulphatase to comprise primarily the di-sulphates of compounds I–IV.

The hydrolysis of the chemically synthesised di-sulphates by aryl-sulphatase results in their respective aconjugates, compounds I, II and (III+IV).

The chemical glucuronidation of compound I (see FIG. 13) results in two products with retention times and absorption spectra that correspond with the two urine metabolite peaks of Fraction A (see FIGS. 5–6). The semi-synthetic glucuronides of compound I are hydrolysed by β-D-glucuronidase. The two glucuronate products of compound I may represent glucuronidation at either the meta- or para position—this is untested.

All conjugates of compounds I, II and (III+IV) show a shift in their absorbance spectra to a lower wavelength as compared to their aconjugates under the prevailing analytical parameters. This is independent of whether they are glucosides, glucuronides or sulphates, whether semi-synthetic or biologically derived. These comparative spectra may be seen in FIGS. 20–22, 29 and 31.

Metabolic and/or synthetic conjugation of aconjugtes I and (III+IV) may take place at hydroxyl groups at the meta-position of the phenyl rings, resulting in many more combinations of conjugated products. It is believed however that para-substitution is preferred due to chemical considerations.

EXAMPLE 9

Compounds I–XXVIII were subjected to in vitro testing for inhibition of human immunodeficiency virus type I (HIV-1) proliferation as follows:

Human peripheral blood lymphocytes (PBL's) obtained by density gradient centrifugation of blood from healthy volunteers at a blood bank were pooled and used for the propagation of HIV-1 in vitro.

The PBL's were polyclonally activated with phytohaemagglutinin (PHA) and subjected to quality controls whereby their viability was tested with Trypan blue exclusion and the expression of activation antigens, CD4$^+$ and CD25$^+$ was measured by immunofluorescence. Prior to adding the test substance, the activated PBL's were exposed to a standardized titre of HIV-1 virus and after incubation for 60 minutes the cells were washed twice and plated into microtitre plates at a concentration of 2×10$^6$ cells/well. The medium contained interleukin-2 and in control wells the virus produced between 50 and 100 ng/ml of p24 core protein on day 4. The test substance was added to these cultures either in water or dimethyl sulphoxide (DMSO) depending on solubility characteristics. The final DMSO concentration, when used, was always 1% v/v.

HIV replication was measured as the production of p24 core protein and the production of HIV RNA on days 2, 3 and 4, or on days 3, 4, 5 and 6. Core protein p24 was measured using 'Sandwich ELISA' technology using inter alia a monoclonal antibody against p24 core protein. The HIV RNA was measured using a specific labelled DNA probe against HIV RNA and the process of hybridization.

Results were expressed as percent inhibition of HIV-1 p24 core protein production or RNA production on days 3, 4 or 6.

Possible toxic effects of the test substances were measured by viability testing using Trypan blue or a proliferation assay using 3-(4,5-dimethylthiazol-2-yl)-2,5-diphenyl-2H-tetrazolium bromide (MTT) on day 4 or day 6 after initiation of the experiment (Borenfreund et al: Toxicol. In Vitro, 1988, 2, 1–6).

It is to be noted that DMSO at 1% by v/v does not inhibit HIV-I replication.

The toxicity of the drug was expressed as a percentage inhibition of lymphocyte proliferation as measured with MTT and compared with controls receiving the virus but no drug.

In each test, cells were also exposed to HIV-1 and 3'-azido-3'-deoxythymidine (also known as Zidovudine or AZT) at 100, 10, 1 and 0.1 ng/ml. This was a positive control and compounds tested were compared to the inhibitory effect of 10 ng/ml AZT.

In all of the following Tables, percentage inhibition refers to inhibition of p24 core protein production and HIV RNA production relative to infected controls. Percentage AZT inhibition refers to inhibition caused by 10 ng/ml AZT at the end of the experiment, i.e. after 4 or 6 days.

CRUDE EXTRACTS

A dried methanolic extract of *Hypoxis rooperi*, (see FIG. 1), was dissolved in DMSO and added to test cells at a final concentration of 70 μg/ml (DMSO final concentration was 1% v/v). After 4 days of incubation p24 core protein production was inhibited by 100% and HIV RNA production by 85%. Cell proliferation was 76% of that of the control. AZT at 10 ng/ml caused 100% inhibition of p24 core protein production and 96% of HIV RNA production.

PURIFIED COMPOUND V

In order to ascertain which component of the crude methanolic extract was involved in HIV-1 proliferation inhibition, HPLC-purified hypoxoside, (see FIG. 3), was tested per se dissolved in water. The following results were obtained after 6 days using a standard titre of HIV-1:

TABLE 2

| Compound | μg/ml | % inhibition:p24 core protein | % inhibition: HIV-RNA | Proliferation as a percentage of control value |
|---|---|---|---|---|
| V | 50 | 99 | 100 | 82 |
| V | 25 | 9 | 83 | 93 |
| V | 12.5 | 5 | 65 | 94 |
| V | 6.25 | 5 | 42 | 94 |

At 10 ng/ml AZT inhibited p24 core protein production by 20% and HIV-RNA production by 68%.

Using the same sample of compound V but lowering the viral titre ten-fold, the following results were obtained:

TABLE 3

| Compound | μg/l | % inhibition:p24 core protein | % inhibition: HIV-RNA | Proliferation as a percentage of control value |
|---|---|---|---|---|
| V | 50 | 100 | 99 | 82 |
| V | 25 | 90 | 97 | 93 |
| V | 12.5 | 0 | 11 | 94 |
| V | 6.25 | 0 | 0 | 94 |

At 10 ng/ml AZT inhibited p24 core protein production and HIV-RNA by 99%.

COMPOUNDS V–VIII

In a further test, compounds V–VIII, as isolated from *Hypoxis latifolia*, (see FIG. 2), were tested, as dissolved in water, and results obtained after 3 and 6 days of incubation were the following:

TABLE 4

(After 3 days)

| Compounds | μg/ml | % inhibition:p24 core protein | % inhibition: HIV-RNA | Proliferation as a percentage of control value |
|---|---|---|---|---|
| V–VIII | 100 | 100 | 100 | 50 |
| V–VIII | 50 | 100 | 100 | 52 |

At 10 ng/ml AZT caused 50% inhibition of p24 core protein production and 46% inhibition of HIV-RNA production.

TABLE 5

(After 6 days)

| Compounds | μg/ml | % inhibition:p24 core protein | % inhibition: HIV-RNA | Proliferation as a percentage of control value |
|---|---|---|---|---|
| V–VIII | 100 | 100 | 99 | 50 |
| V–VIII | 50 | 100 | 100 | 52 |

At 10 ng/ml AZT caused 50% inhibition of p24 core protein production and 46% inhibition of HIV-RNA production.

COMPOUNDS IX–XII

Hypoxoside (compound V) and its structurally related compounds were sulphated to yield compounds IX–XII, see FIG. 25) and tested for inhibition of HIV-1 proliferation after 6 days, yielding the following results:

TABLE 6

(Standard viral titre)

| Compound | μg/ml | % inhibition:p24 core protein | % inhibition: HIV-RNA | Proliferation as a percentage of control value |
|---|---|---|---|---|
| IX–XII | 50 | 100 | 100 | 93 |
| IX–XII | 25 | 100 | 100 | 88 |
| IX–XII | 12.5 | 29 | 87 | 90 |
| IX–XII | 6.5 | 8 | 54 | 98 |

At 10 ng/ml AZT caused 20% inhibition of p24 core protein production and 68% inhibition of HIV-RNA production.

TABLE 7

(Ten-fold dilution of standard viral titre)

| Compound | μg/ml | % inhibition:p24 core protein | % inhibition: HIV-RNA | Proliferation as a percentage of control value |
|---|---|---|---|---|
| IX–XII | 50 | 100 | 100 | 93 |
| IX–XII | 25 | 100 | 100 | 88 |
| IX–XII | 12.5 | 97 | 98 | 90 |
| IX–XII | 6.25 | 28 | 23 | 98 |

At 10 ng/ml AZT caused 99% inhibition of p24 core protein and HIV-RNA production.

COMPOUND XVII

Compound I was sulphated to yield compound XVII (see FIGS. 28–29) which was tested for inhibition of HIV-1 proliferation in vitro, yielding the following results:

TABLE 8

(3 days incubation)

| Compounds | μg/ml | % inhibition:p24 core protein | % inhibition: HIV-RNA | Proliferation as a percentage of control value |
|---|---|---|---|---|
| XVII | 100 | 88 | 93 | 80 |
| XVII | 50 | 47 | 68 | 84 |
| XVII | 100 | 100 | 100 | 94 |
| XVII | 50 | 87 | 91 | 96 |

At 10 ng/ml AZT caused 50% inhibition of p24 core protein production and 46% inhibition of HIV-RNA production.

At 10 ng/ml AZT caused 96% inhibition of p24 core protein production and 92% inhibition of HIV-RNA production.

A mixture of compounds I–IV was sulphated to give compounds XVII–XX respectively (see FIG. 32) and incubated for 6 days yielded the following results.

TABLE 9

| Compounds | μg/ml | % inhibition:p24 core protein | % inhibition: HIV-RNA | Proliferation as a percentage of control value |
|---|---|---|---|---|
| XVII–XX | 100 | 100 | 100 | 80 |
| XVII–XX | 50 | 100 | 100 | 86 |

At 10 ng/ml AZT caused 96% inhibition of p24 core protein production and 92% inhibition of HIV-RNA production.

COMPOUND XVIII

Compound II was sulphated to give compound XVIII (see FIGS. 30–31) and yielded the following results after 6 days.

TABLE 10

| Compounds | μg/ml | % inhibition:p24 core protein | % inhibition: HIV-RNA | Proliferation as a percentage of control value |
|---|---|---|---|---|
| XVIII | 100 | 100 | 100 | 50 |
| XVIII | 50 | 79 | 87 | 63 |

At 10 ng/ml AZT caused 96% inhibition of p24 core protein production and 92% inhibition of HIV-RNA production.

IN VIVO-PRODUCED METABOLITES OF COMPOUNDS V–VIII

Orally ingested hypoxoside (compound V) is converted to compound I in the large intestine by bacterial β-glucosidase. Compound I is excreted in the faeces but is also absorbed and converted by phase II biotransformation to sulphate and glucuronic acid conjugates (fractions A, B and C in FIG. 6). Fraction A, containing primarily the diglucuronides of compounds I–IV, i.e. compounds XIII–XVI, yielded the following results:

TABLE 11

| Compounds | μg/ml | % inhibition:p24 core protein | % inhibition: HIV-RNA | Proliferation as a percentage of control value |
|---|---|---|---|---|
| 4 days incubation | | | | |
| XIII–XVI | 100 | 45 | 20 | 97 |
| XIII–XVI | 100 | 57 | 31 | 97 |

At 10 ng/ml AZT caused 100% inhibition of p24 core protein production and 97% inhibition of HIV-RNA production.

FRACTIONS A–C

Fractions A, B and C of urinary metabolites of compounds V–VIII (i.e. compounds XIII–XVI (fraction A); compounds XXI–XXVIII (fraction B) and compounds XVII–XX (fraction C) (see FIGS. 5–6)) were tested and yielded the following results alter 3 days of incubation.

TABLE 12

| Compounds | μg/ml | % inhibition:p24 core protein | % inhibition: HIV-RNA | Proliferation as a percentage of control value |
|---|---|---|---|---|
| 3 days incubation Fraction A (FIG. 6) | | | | |
| XIII–XVI | 100 | 80 | 97 | 80 |
| XIII–XVI | 50 | 25 | 73 | 86 |
| Fraction B (FIG. 6) | | | | |
| XXI–XXVIII | 100 | 68 | 81 | 78 |
| XXI–XXVIII | 50 | 36 | 71 | 73 |
| Fraction C (FIG. 6) | | | | |
| XVII–XX | 100 | 86 | 100 | 81 |
| XVIII–XX | 50 | 67 | 81 | 79 |

At 10 ng/ml AZT caused 50% inhibition of p24 core protein production and 46% inhibition of HIV-RNA production.

Fraction B of the urinary metabolites of compounds V–VIII (see FIG. 6) was sub-fractionated into two fractions. Fraction V1 is the ascending half of fraction B and fraction V2 is the descending half of fraction B. These tractions were tested individually for inhibition of HIV replication and yielded the following results over 4 and 6 days of incubation.

TABLE 13

| Compounds | | μg/ml | % inhibition:p24 core protein | % inhibition: HIV-RNA | Proliferation as a percentage of control value |
|---|---|---|---|---|---|
| 4 days incubation | | | | | |
| XXI–XXVIII | V1 | 100 | 100 | 33 | ND |
| XXI–XXVIII | V2 | 100 | 100 | 100 | ND |
| 6 days incubation | | | | | |
| XXI–XXVIII | V1 | 200 | 84 | 70 | ND |
| XXI–XXVIII | V2 | 200 | 100 | 100 | ND |

(ND = not determined)

At 10 ng/ml AZT inhibited p24 core protein production and
HIV-RNA production on days 4 and 6 by 100%.

EXAMPLE 10

Material and Methods

Subjects:

All patients entered into the study were HIV-positive as determined by a commercial enzyme-linked immunosorbent assay (ELISA) and alter a positive ELISA result had been confirmed by the Western blotting technique.

The cohort studied consisted of 18 subjects of both sexes of whom 7 volunteered to act as a treated group (*H. accuminata* extract, see Example 2 was used in the study), while the remaining 11 subjects served as a control, non-treated group. No other anti-retroviral agents were used by any subject in the study.

Venous blood samples (clotted and whole EDTA) were drawn at the first visit (baseline) and again at monthly intervals.

Capsules:

Each capsule contained 200 mg Hypoxis species extract (about 100 mg of compounds V–VIII) and the patients were advised to ingest 2 such capsules 3 times daily, i.e. a total of 1200 mg/day of extract was ingested.

Blood Analysis

Clotted Blood:

This specimen of blood was used to quantitate serum HIV antigenemia by means of a commercial capture ELISA kit. The incubation conditions used included the pretreatment of each serum sample with glycine-HCl buffer in order to dissociate immune complexes. This ensured that so-called total p24 core protein was measured and not only that which remains in circulation, uncomplexed by anti-p24 core protein antibodies.

The results were expressed as absolute pg/ml serum as determined from a calibration curve.

EDTA whole blood:

Whole blood was used to identify and quantify lymphocyte subsets by monoclonal antibodies. Briefly, 100 μl of blood was incubated with mixtures of monoclonal antibodies labelled with different fluorochromes as follows:

CD3-FITC/CD4-PE

CD3-FITC/CD8-PE

CD3-FITC/CD19-PE

CD3-FITC/CD16+CD56-PE
CD8-FITC/HLA-Dr-PE

These mixtures detect the following cellular subsets: T-helpers; T-suppressors; B-cells; NK-cells and activated suppressor cells respectively.

After a 20 minute incubation, red blood cells were lysed with a lysing solution (FACS lysing buffer) and the cells were pelleted and washed once with phosphate buffered saline solution (PBS). The cells were fixed in 500 μl PBS containing 0.5% v/v formaldehyde.

Cell fluorescence was assessed using a FACScan cytometer. FL1 (fluoroscein) was measured using a 530/30 nm band pass filter and the FL2 (phycoerythrin) with a 585/42 nm band pass filter. The analysis was conducted using the Simulset software programme which automatically sets up a lymphocyte gate by the exclusion of granulocytes and monocytes from the analytical gate.

All the results were expressed as percentage positive lymphocytes i.e. cells which co-expressed CD3 and CD4 or CD3 and CD8, etc. In this way, CD4-positive monocytes were excluded from the calculation of $CD4^+$ T-cells. Similarly, $CD8^+$ natural killer (NK) cells were excluded from the $CD3^+$ $CD8^+$T-suppressor subset.

Absolute cell numbers were calculated from basic haematology conducted on an aliquot of the whole blood. From the percentage lymphocyte differential counts, absolute values for positive cells could be calculated. This was conducted for all subsets analysed.

Changes observed between the baseline and follow-up values within subsets were analysed in the following manner:

The absolute value for a particular subset for a patient at baseline=X

The same parameter measured at the first follow-up=X'

Hence the change in this parameter=X'–X

A positive value for X'–X indicates an increase in the parameter measured. Conversely, a negative value indicates a decrease in the parameter between the follow-up value and that of baseline.

The mean change in this parameter for each group was calculated for all the subjects in the group and the results expressed as either the mean absolute change or as the mean percentage change relative to the baseline value.

RESULTS:

Serum Viral Antigenemia (p24 core protein Levels)

Serum p24 core protein determinations revealed that the treated group (n=7) showed a mean decrease of –13.8 pg/ml when compared to the control, non-treated cohort (n=11) whose mean p24 core protein levels rose by 17.9 pg/ml over the same period of 1 month. Similarly, when the p24 core protein levels of the 2-month follow-up were analysed, the treated group (n=6) exhibited a mean increase of 2.5 pg/ml which compared favourably with the mean increase of 31.4 pg/ml in the non-treated group (n=4). These results are represented graphically in FIG. 33.

It should be noted that, in four of the treated patients whose follow-up periods were longer, the p24 core protein levels are non-detected by the method employed while no such decreases or reversion to negativity was highlighted in any of the non-treated subjects. On the contrary, the non-treated subjects exhibited ever-increasing p24 core protein levels with time.

Lymphocyte Subsets:

As shown in Table 4. the patients in the treated group (n=7) showed very favourable increases in all the lymphocyte subsets analysed. Indeed, the mean increase in total lymphocyte counts after a month was accompanied by general increases in $CD3^+$ cells (T cells), T-helper cells ($CD4^+$), T-suppressor cells ($CD8^+$), B cells and NK cells, as well as the fraction of $CD8^+$ cells expressing markers of cellular activation ($CD8^+$ Dr cells). These mean increases in the cellular subsets measured compare favourably with published results of clinical trials conducted with other anti-retroviral agents such as AZT (as mentioned in Example 9) and Didanosine. Indeed, Fisch et al (New Eng. J. Med., 1990, 323, 1009–1014) reported a transient mean increase of 25 $CD4^+$ cells/mm$^3$ of blood in their groups treated with standard doses (250 mg/4-hours) and reduced doses (100 mg/4 hours) of AZT for 30 months.

On the other hand, the non-treated group (n=11) showed deteriorating immune parameters over the same period of time (Table 14). As can be seen, most cellular subsets exhibited decreases after a month of follow-up which appears to confirm the decline in immune status in these subjects as highlighted by the p24 core protein levels reported above.

TABLE 14

Mean Absolute Changes in the Cellular Subsets after 1 Month Follow-Up. Comparison of the Groups Values are expressed as absolute cells/μl blood.

|  | NON-TREATED SUBJECTS (n = 11) | TREATED SUBJECTS (n = 7) |
| --- | --- | --- |
| Total Lymphocytes | –122 | +144 |
| $CD3^+$ Cells | –109 | +100 |
| $CD4^+$ Cells | –17 | +36 |
| $CD8^+$ Cells | –89 | +69 |
| B Cells | +23 | +21 |
| NK Cells | –34 | +36 |
| Activated $CD8^+$ Cells | –51 | +52 |

Positive results indicate an increase relative to the baseline value while a negative value indicates a decrease relative to the baseline value.

These differences between the groups are not only evident when one compares the mean absolute changes, but are also reflected in the mean percentage changes relative to the baseline values. For ease of comparison, these data are represented in FIG. 34.

Similar results were obtained with the 2 month follow-up parameters. As can be seen from Table 15. the non-treated group (n=4) exhibited ever decreasing numbers of $CD4^+$, B cells and NK cell numbers. Other cellular subsets showed a slight increase. However, in the treated group, all the parameters measured showed constant, significant increases for both the mean absolute changes as well as in the mean percentage changes (Table 15). Once again, the mean absolute changes observed in our treated group compare favourably with published data from other clinical trials conducted with AZT. These results are shown in FIG. 35.

TABLE 15

Mean Absolute Changes in the Cellular Subsets after a 2 Month Follow-Up Comparison of the Groups
Values are expressed as absolute cells/l blood

|  | NON-TREATED SUBJECTS (n = 4) | TREATED SUBJECTS (n = 5) |
|---|---|---|
| Total Lymphocytes | +28 | +218 |
| $CD3^+$ Cells | +12 | +114 |
| $CD4^+$ Cells | -42 | +38 |
| $CD8^+$ Cells | +17 | +80 |
| B cells | -10 | +62 |
| NK Cells | -13 | +97 |
| Activated $CD8^+$ Cells | +28 | +14 |

Positive values indicate an increase relative to the baseline value while a negative value indicates a decrease relative to the starting value.

From Example 10 an extract from Hypoxis species has been shown to have anti-HIV activity in vitro in that it inhibits both HIV replication (p24 core protein production) and HIV RNA production.

The results are promising in that they show that subjects ingesting 1,200 mg of Hypoxis species extract/day exhibit improved immune status after 1 month and also after 2 month on the treatment. The immune parameters measured include: increased numbers of T-cells (both T-helper and T-suppressor cells); B-cells and NK cells. In parallel, there was a substantial decrease and retardation of p24 core protein production as measured in the sera of the subjects.

On the other hand, control, non-treated subjects exhibited ever-deteriorating immune parameters and increasing p24 core protein serum levels over the same period. These subjects showed continuous loss of their $CD4^+$ cells as well as other cellular subsets as shown in other anti-HIV clinical trials (Foulds et al: Drugs, 1992, 44, 94–116 and Prince et al: J. Acq. Immuno. Def., 1991, 4, 1227–1232).

EXAMPLE 11

Inhibition of Respiratory Syncytial Virus (RSV) by Compound XVIII

Compound XVIII was added to Hep-2 cells growing as slope cultures in plastics tubes to give final concentrations respectively of 50, 100 and 200 µg/ml. The cultures were then respectively inoculated with a high standard viral dose, one tenth ($\frac{1}{10}$) of said standard dose, and one hundredth ($\frac{1}{100}$) of said standard dose of respiratory syncytial virus (RSV). After four days of incubation at 33° C. the cells were visually inspected using an inverted phase contrast microscope and scored for the extent of syncytium formation, i.e. single cells containing three or more nuclei, as follows: a=0–25%, b=25–50%, c=50–75% and d=75–100% of cells having three or more nuclei.

The results obtained are shown in Table 16 hereunder:

TABLE 16

Extent of Syncytium Formation in the Presence and Absence of Compound XVII after 4 days of Incubation

|  | Viral Dose | | |
|---|---|---|---|
| Conditions of Incubation | Full | 1/10 | 1/100 |
| Virus control | d | c | b |
| Virus plus 50 µg/ml | d | c | a |
| Virus plus 100 µg/ml | c | a | Nil |
| Virus plus 200 µg/ml | Nil | Nil | Nil |

EXAMPLE 12

Effect of Compound XVII on Cytomegalo-virus (CMV)

Compound XVII was added to primary foetal human fibroblasts in tissue culture, to yield final concentrations respectively of 50, 100 and 200 µg/ml. The cultures were then respectively inoculated with a high standard viral dose, with one tenth ($\frac{1}{10}$) of said standard dose and with one fiftieth ($\frac{1}{50}$) of said standard dose of cytomegalo-virus (CMV) and incubated for four days.

The cytopathic effect of CMV was determined by microscopic visual inspection of the cell cultures, in terms of the extent of gross swelling of the cells, where: a=0–25%, b=25–50%, c=50–75% and d=75–100% of the cells affected by gross swelling.

The results obtained are shown in Table 17 hereunder.

TABLE 17

Effect of Compound XVII on the Extent of the Cytopathic Effect of Cytomegalo-Virus after 4 days of Incubation

|  | Viral Dose | | |
|---|---|---|---|
| Conditions of Incubation | Full | 1/10 | 1/50 |
| Virus control | c | b+ | a |
| Virus plus 50 µg/ml | bc | b | a |
| Virus plus 100 µg/ml | bc | ab | a– |
| Virus plus 200 µg/ml | Nil | Nil | Nil |

At 200 µg/ml 5 out of 8 cultures showed signs of toxicity due to the compound.

EXAMPLE 13

Tests on compound XVII were conducted by the Department of Health and Human Services at the National Institutes of Health in Bethesda, Md., U.S.A. (NSC No. 658946, dated 20 Apr.1993 and 2 Mar. 1993). The results of the test are given in FIGS. 42 and 43 and in Tables 18 and 19. The tests showed that compound XVII is "confirmed moderate" in in vitro anti-HIV drug screening.

In FIGS. 42 and 43

- • - • - represents 0% and 50% reference lines

..... represents viral cytopathic effect

———— represents infected treated culture

- - - - - represents uninfected treated culture

TABLE 18

In Vitro anti-HIV drug screening results for compound XVII; primary screen (cell line CEM-SS)

| INDEX | SUMMARY CONCENTRATION | DOSE µg/ml | INFECTED RESPONSE Percent of Control | UNINFECTED RESPONSE Percent of Control |
|---|---|---|---|---|
| IC50 (µg/ml) | $>1.50 \times 10^{+2}$ | $4.80 \times 10^{-2}$ | 5.15 | 99.95 |
| EC50 (µg/ml) | $1.40 \times 10^{+2}$ | $1.50 \times 10^{-1}$ | 5.56 | 98.85 |
| T150 (IC/EC) | $>1.10 \times 10^{0}$ | $4.80 \times 10^{-1}$ | 3.04 | 93.25 |
| | Conclusion | $1.50 \times 10^{0}$ | 5.22 | 99.75 |
| | CONFIRMED MODERATE | $4.80 \times 10^{0}$ | 8.88 | 98.57 |
| | | $1.50 \times 10^{+1}$ | 7.53 | 92.22 |
| | | $4.70 \times 10^{+1}$ | 14.16 | 83.31 |
| | | $1.50 \times 10^{+2}$ | 55.88 | 55.40 |

TABLE 19

In Vitro anti-HIV drug screening results for compound XVII: primary screen (cell line CEM-IW)

| INDEX | SUMMARY CONCENTRATION | DOSE µg/ml | INFECTED RESPONSE Percent of Control | UNINFECTED RESPONSE Percent of Control |
|---|---|---|---|---|
| IC50 (µg/ml) | $>1.50 \times 10^{+2}$ | $4.80 \times 10^{-2}$ | 4.32 | 93.34 |
| EC50 (µg/ml) | $9.80 \times 10^{+1}$ | $1.50 \times 10^{-1}$ | 3.53 | 98.04 |
| T150 (IC/EC) | $>1.50 \times 10^{0}$ | $4.80 \times 10^{-1}$ | 5.50 | 94.68 |
| | Conclusion | $1.50 \times 10^{0}$ | 6.55 | 86.37 |
| | CONFIRMED MODERATE | $4.80 \times 10^{0}$ | 4.53 | 92.25 |
| | | $1.50 \times 10^{+1}$ | 4.87 | 93.42 |
| | | $4.70 \times 10^{+1}$ | 6.72 | 90.57 |
| | | $1.50 \times 10^{+2}$ | 78.11 | 70.68 |

EXAMPLE 14

Introduction

The human immunodeficiency virus (HIV), the etiologic agent of AIDS, selectively infects cells expressing the CD4 surface molecule, particularly T lymphocytes as well as cells of the monocyte/macrophage lineage. As a consequence of infection with HIV, CD4+T cells demonstrate substantial quantitative and qualitative detects and the depletion of CD4 cells in the blood has, to date, been shown to be the best marker to predict progression to AIDS (Fahey J. L., Taylor J. M., Detels R., et al (1990): The prognostic value of cellular and serologic markers in infection with immunodeficiency virus type 1. N Engl J Med, 333: 166–172; Eyster M. E., Ballard J. O., Gall M. H., et al (1989): Predictive markers for the acquired immunodeficiency syndrome (AIDS) in hemophiliacs: persistance of p24 antigen and low T4 cell count. Ann Intern Med, 110: 963–969; Phillips A., Lee C. A., Elford J., et al (1989): Prediction of progression to AIDS by analysis of CD4 lymphocyte counts in a hemophilic cohort. AIDS, 3: 737–741).

Materials and methods

Patients and blood analyses

Informed consent was obtained from 27 HIV positive individuals to take capsules containing a methanolic extract of H. accuminata. These 27 subjects included the 18 subjects of the study reported in Example 10 and this study is thus a continuation of the study reported in Example 10. They were not on concommitant anti-retrovirals, but received prophylactic medication for infections if the need arose. They took 6 capsules each containing 200 mg of the plant fraction per day. Blood samples were drawn at monthly intervals over a period of 27 months (n=304 determinations) for clinical chemistry, haematology and for the measurement of CD4 cells and other subsets by flow cytometry (FACScan, Becton Dickinson) using two-colour conjugated monoclonal antibodies. Clotted blood was also drawn for the measurement of viral antigenaemia (p24 levels) by the monoclonal antibody capture method with acid dissociation as suggested by the manufacturers (Coulter HIV p24 kit, Coulter Electronics). In parallel, a group of patients who elected not to take the capsules served as controls. They were also not on any anti-retrovirals and were monitored over a period of 18 months (n=57 determinations). The data of each patient were expressed as a ratio of CD4 counts/baseline counts and analysed with the aid of the STATGRAPHICS (v.6) computer programme of Statistical Graphics Corporation.

Data Analysis:

The data were analysed in several ways: changes in the CD4 cell numbers in both groups were calculated relative to those at entry (baseline), 3, 6 and 12 months and were expressed as either mean absolute CD4 cell changes or as mean percentage changes. These differences within the groups were analysed statistically by the non-parametric Wilcoxon Rank test. Comparison between the groups (p24 serum levels and activated CD8 cells) was conducted by the Chi-squared test by comparing the percentage of patients exhibiting positive or negative changes in these parameters.

Results:

Although the two groups studied were unequal in numbers, analysis of the median (SEM) CD4 cells numbers at entry indicated that the two groups did not differ statistically: median (SEM) of 396±37/µl blood in the treated group (range 27–717/µl) versus 437±90/µl blood in the non-treated group (range 72–545/µl); hence, changes occurring in any of the parameters measured within the treated group could not be accounted for by a biased selection of patients.

Analysis of the changes in the CD4 cell counts at 3 months showed a statistically significant increase in these cells in the treated group (n=27; p=0.02) whereas the non-treated group (n=5) did not show this trend in their cell numbers (Table 20).

TABLE 20

Comparison of Mean CD4 cell changes (absolute and percentage changes relative to baseline value) between treated and non-treated groups at different time points:

| CD4 cell changes (Time; months) | Groups | |
|---|---|---|
| | Treated | Non-Treated |
| 3: Absolute (/μl) | 37 ± 79$^{ac}$ (n = 27) | 51 ± 213$^b$ (n = 5) |
| Percentage | 16.6 ± 24.5 | 6.5 ± 70.4 |
| 6: Absolute (/μl) | 19 ± 85$^b$ (n = 24) | −33 ± 195$^b$ (n = 11) |
| Percentage | 5.9 ± 28.0 | −9.9 ± 42.5 |
| 12: Absolute (/μl) | 16 ± 100$^{bd}$ (n = 15) | −15 ± 79$^b$ (n = 7) |
| Percentage | 1.6 ± 22.7 | −18.1 ± 36.0 | p=0.02 (significant change in absolute CD4 cell numbers within group; Wilcoxon Rank test).

b: Not significant c: p<0.001 (significant difference between the groups; Chi squared test)

d: p=0.013 (significant difference between the groups; Chi squared test)

Comparison of the groups at this time revealed a statistically significant difference between the two groups (p<0.001) by the Chi-squared test. Similarly, analysis of the CD4 cells within the groups at 6 and 12 months exhibited a mean positive change for the treatment group (although this had returned to baseline values and was not statistically significant, (FIG. 41), whereas the non-treated group showed a steady decline in their cell numbers over the same period of time (Table 20). FIG. 36 depicts regression analysis of the data from treated patients. Confidence limits (95% level) are shown as the dotted lines closest to the regression line, while prediction limits (95% level) are shown as the dotted lines farthest from the regression line. The slope of the regression line (−0.006) had a probability level of 0.026, which is statistically significant. Comparison of the groups showed a significant difference between them at 12 months (p=0.01). The number of patients at each time point is not equivalent to those at baseline (n=24 and n=15 at 6 and 12 months respectively for the treated group) however the analysis was conducted on the same group of patients.

The analysis of the data from long term patients revealed the following trends: individuals taking the capsules for 18 months and longer showed stable CD4 cell numbers comparable to those at baseline (FIG. 40) indicating a slowing down of CD4 cell loss, contrary to what would be expected from the natural history of this disease. FIG. 37 shows regression analysis of the control data. The regression line also had a negative trend (slope=−0.018), but the probability level of 0.18 is statistically not significant. Indeed, regression analysis of the CD4 cell counts of each patient and that of the group as a whole at 12 months revealed that the mean correlation coefficient ("r" or the mean slope of the regression lines) was 0.008±0.349, indicating a stabilisation of the cell counts since a negative correlation coefficient would have implied decreases in the cell counts. Furthermore, over the study period, no drug related toxicities, according to clinical chemistry or haematological parameters, were observed in the patients taking the plant extract. No patient deaths occurred during the study period.

To determine whether the two sets of data came from the same distribution, the Kolmogorov-Smirnov Two-Sample test was performed. The significance level of 0.0087, which was computed, suggests a high probability that the two samples are different. A plot of the Cumulative Distribution Function against the CD4/Baseline ratio (FIG. 38) clearly demonstrates a difference. Of significance is that at the lower range of the CD4/Baseline ratios, differences between the control and treated groups were also greatest. Since there is a negative correlation between CD4/Baseline ratio and time, the lowest CD4/Baseline ratios should be encountered at the later stages of the trial. The results thus indicate that the plant extract has the capability of keeping CD4 cell counts at a higher level relative to that of the control. Truncating the data from treated patients at 18 months to bring it in line with the control data did not change this trend.

The extrapolation of the regression lines with time suggests that the control group should achieve a zero CD4/baseline ratio within 58 months at the indicated rate of CD4 cell loss (FIG. 39). The treated group, however, only reach this zero value at approximately 162 months which indicates that the plant extract delays cell loss and thus enhances the prognosis of patients ingesting the capsules.

The Mann-Whitney U test, yielded the following results:

Average rank of the control group=145.86 (57 values).

Average rank of the treated group=187.59 (304 values).

Large sample test statistic Z=2.76973.

Two-tailed probability of equaling or exceeding Z, −0.0056.

The difference in rank between the two samples and the low two-tailed probability again show that the samples are different.

Finally, estimates based on a t-test for hypotheses about the differences between the means (Two-Sample Analysis), yielded the following results:

Computed t statistic=3.11154 with a significance level of 0.00201. Thus the null hypothesis must be rejected, i.e. the samples are different.

Other markers to corroborate the positive changes taking place in the patients ingesting the plant extract included the serum p24 levels and the percentage of activated CD8 cells in the peripheral blood. Indeed, more individuals in the treated group showed decreases in their p24 levels at 3 and 12 months when compared to those not taking the capsules: 53% (n=17) versus 40% (n=5) at 3 months (p=0.04) and 100% (n=3) versus 67% (n=3) at 12 months (p<0.001) for treated versus non-treated groups respectively. Although it is generally accepted that this marker is not the most sensitive to indicate clinical benefit from any therapy since only a certain proportion of patients actually exhibit p24 positivity at any stage of the disease (Cunningham A. L., Dwyer D. E. and Dowton D. N. (1993): Viral markers in HIV infection and AIDS. *J. A.I.D.S.* 6, S32–S35), it has been reported that the p24 antigen capture assay could be used as a surrogate clinical marker and as a tool for evaluating the efficacy of new therapeutic agents (Spector S. A., Kennedy C., McCutchan J. A. et al (1989): The antiviral effect of Zidovudine and Ribavirin in clinical trials and the use of p24 antigen levels as a virologic marker. *J. Infect. Dis.* 159, 822–828.).

As far as the state of immune activation is concerned, it has been shown by Stites et al (Stites D. P., Moss A. R., Bacchetti P., et al (1989): Lymphocyte subset analysis to predict progression to AIDS in a cohort of homosexual men in San Francisco. *Clin. Immumol. Immunipathos.* 52, 96–103.) and Vanham et al (Vanham G., Kestens L., Penne G., et al (1991): Subset markers of CD8(+) cells and their relation to enhanced cytotoxic T-cell activity during Human Immunodefficiency Virus infection. *J. Clin. Immumol.* 11, 345–356.) that increases in CD8$^+$ HLA-Dr$^+$ subpopulations have a strong predictive value for the progression of patients to clinical AIDS and that the use of the absolute number of HLA-Dr$^+$ CD8$^+$ cells improved the predictive value of CD4$^+$ cell counts in a multivariate analysis (Stites et al, supra). In this study, 43% (10/23) of the individuals in the treated group showed a decrease in their CD8$^+$ HLA-Dr$^+$ subpopulations at 6 months as compared to only 27% (3/11) of their non-treated counterparts. Statistical analysis revealed this difference to be significant (p=0.005).

Discussion

The study indicates that the Hypoxis plant fraction stabilizes CD4 cell counts and decreases p24 antigen levels as well as the CD8$^+$ HLA-Dr$^+$ cell subpopulation. The extract contains hypoxoside which is deconjugated to form rooperol which in turn is biotransformed to yield products with significant anti-HIV activity.

The Hypoxis plant fraction is thus capable of maintaining the CD4 cell counts (hence the immune status quo) over an extended time, which is an added advantage over other anti-HIV drugs whose effects of CD4 cell counts seem to be transient in nature. Furthermore, the plant extract is capable of reducing plasma p24 antigenaemia and decreasing the levels of immune activation as indicated by the subpopulations of CD8 cells expressing the HLA-DRr marker of cellular activation.

The above results thus indicate that the capsules containing Hypoxis sp. plant extract are capable of providing an improved prognosis. Firstly, the contents of the capsules increase the CD4 cell numbers of patients over a period of 3 months but thereafter the cell numbers decrease back to baseline values over the following 3 to 6 months. However, the cells remain above the baseline CD4 level for at least a period of 17 months. Secondly, analysis of the long term CD4 data indicates that the treated group of patients react differently to the controls. The rate of CD4 cell loss within the non-treated, control group occurs at a significantly higher rate when compared to that of the treated group. Furthermore, this loss, when extrapolated, achieves a zero value at ±58 months for the non-treated patients whereas for the treated group, this zero value is only reached at ±162 months. This implies a 3-fold increase in life expectancy in patients ingesting the capsules in the absence of ally other anti-retrovirals. Thirdly, the lack of observable toxicity (according to chemical or haematological parameters) in all patients ingesting the Hypoxis sp plant extract has an added advantage over current anti-retrovirals. Indeed, it is known that the current available therapies for HIV infected individuals are not without side-effects (bone marrow suppression, pancreatitis, etc.). The Hypoxis extract has also been shown in prior studies not to exhibit such toxicities.

The Hypoxis plant extract is able to stabilize CD4 cell courts over a period of at least 17 months. Thereafter, the CD4 cell loss is retarded and in this way, the prognosis of patients is much improved. This is particularly useful in view of the costs of current anti-retrovirals and the availability of such therapies in developing countries. It has been found that in HIV infected individuals the loss of the immune cells (especially CD4 cells) is directly linked to increased frequency of opportunistic infections and to disease progression. The fact that the plant extract of the invention is capable of slowing down this process (and hence of maintaining the status quo of the patients' immunity), indicates a lower morbidity and an increased life expectancy.

EXAMPLE 15

Background

In order to assess the short and long term toxicity of oral ingestion of hypoxoside, twenty four patients were given 1200–3200 mg of standardized Hypoxis plant extract daily. These patients had histologically proven lung cancer. Nineteen patients survived an average of four months with progression of their primaries and metastases while five patients survived more than a year while on hypoxoside therapy. One patient survived for five years and histology of the primary lesion showed absence of cancer. No toxic effects, either in clinical examinations, clinical chemistry or haematological analyses were found that could be ascribed to the ingestion of hypoxoside. Only one occasion of possible drug intolerance with anxiety, nausea, vomiting and diarrhoea was noted.

Introduction

FIG. 47 summarizes some results of research conducted on hypoxoside [Albrecht, C., Theron, E. and Kruger, P.; Morphological characterization of the cell-growth inhibitory activity of rooperol and pharmacokinetic aspects of hypoxoside as an oral prodrug for cancer therapy (Submitted for publication, 1994); Theron, E., Albrecht, C., Kurger, P., Jenkins, K. and Van der Merwe, M. J.; Beta-glucosidase acitivity in fetal calf serum renders the plant glucoside, hypoxoside, cytotoxic towards BL-6 mouse melanoma cells; *In-Vitro Cell. Dev. Biol.*, 1994; 30A: 155–119; Kruger, P. B., Albrecht, C., Liebenberg, R. W. and Van Jaarsveld, P. P.; Studies on hypoxoside and rooperol analogues from *Hypoxis rooperi* and *H. latifolia* and their biotransformation in man by using high-performance liquid chromatography with in-line sorption enrichment and diode array detection; *J. Chromat.* (Accepted for publication, 1994)].

Hypoxoside is non-toxic to cancer cells in tissue culture, but when deconjugated to rooperol significant cytotoxicity is found at relatively low concentrations. After oral ingestion no hypoxoside or rooperol are found in the circulation [Kruger, P. B., Albrecht, C., Liebenberg, R. W. and Van Jaarsveld, P. P.; (supra). Only phase II metabolites (glucuronides and sulphates) of rooperol are present. Like the glucoside, the conjugated metabolites are also non-toxic to cells in tissue culture, but they can be activated by treatment with glucuronidase [Albrecht, C., Theron, E. and Kruger, P.; (supra)]. Since it is known that certain tumours contain relatively high levels of glucuronidase [Connors, T. A. and Whisson, M. E.; Cure of mice bearing advanced plasma cell tumours with analine mustard: the relationship between glucuronidase activity and tumour sensitivity; *Nature* 1966, 210: 866–867; Double, J. A. and Workman, P.; A new high-glucuronidase mouse tumour curable by aniline mustard therapy; *Cancer Treatment Reports* 1977, 61: 909–911; Rubin, D. M. and Rubin. E. J.; A minimal toxicity approach to cancer therapy: Possible role of beta-glucuronidase. *Medical Hypotheses* 1980, 6: 85–92; Young, C. W., Yagoda, A., Bittar, E. S., Smith, S. W., Grabstald, H. and Whitmore, W.; Therapeutic trial of aniline mustard in patients with advanced cancer. Comparison of therapeutic response with cytochemical assessment of tumor cell beta-glucuronidase activity. *Cancer* 1976, 38: 1887–1895] activation of rooperol metabolites at the site of a tumour would result in selectivity in cancer chemotherapy.

The quantitative sequestration of rooperol metabolites in the bile of experimental animals such as mouse, rat and dog [Albrecht, C., Theron, E. and Kruger, P. (supra)] however, excluded their use as an in vivo anticancer model for hypoxoside. A phase I clinical trial was therefore conducted on 24 lung cancer patients for whom no alternative therapy was available. The first part of the trial included a study of the pharmacokinetic behaviour of the metabolites [Albrecht, C. F., Kruger P. B., Smit B. J., Freestone M., Gouws L., Koch H. P., Miller R. and van Jaarsveld P. The pharmacokinetic behaviour of hypoxoside taken orally by patients with lung cancer in a phase I trial; (Submitted for publication 1994)]. A wide interpatient variation in concentration-time relationships was found which can be explained by active enterohepatic recirculation, a lag phase in absorption and saturable conversion of hypoxoside to rooperol in the colon. However, the elimination of the metabolites follow predictable first order kinetics with acceptable t½=values (20–50 hours). To determine toxicity, maintenance doses were individualized for patients in order to obtain metabolite levels near 100 µg/ml. This concentration was found to be cytotoxic in vitro after enzymatic activation [Albrecht, C., Theron, E. and Kruger P. (supra)].

Materials and Methods

Medication and monitoring of metabolite serum levels

Hypoxoside was supplied as a standardized plant extract in capsule form, each containing 200 mg of plant extract. Quality control was assured by high performance liquid chromatography [Kruger, P. B., Albrecht, C., Liebenberg, R. W. and Van Jaarsveld, P. P. (supra); Albrecht, C. F., Kruger P. B., Smit B. J., Freestone M., Gouws L., Koch H. P., Miller R. and van Jaarsveld P. P. (supra)]. The hypoxoside content of the standardized plant extract ranged from 50–55% [Albrecht, C. F., Kruger P. B., Smit B. J., Freestone M., Gouws L., Koch H. P., Miller R. and van Jaarsveld P. P. (supra)]. Routine monitoring of metabolite serum levels was done by using high pressure liquid chromatography [Kruger, P. B., Albrecht, C. F. and Van Jaarsveld, P. P.; Use of guanidine hydrochloride and ammonium sulphate in comprehensive in-line sorption enrichment of xenobiotics in biological fluids by high performance liquid chromatography. *J. Chromat.*, 1993; 612: 191–198].

Study design

The patients were hospitalized for the duration of the pharmacokinetic studies. During the long term therapy stage, patients returned to hospital every 2 weeks and underwent full clinical examinations including X-ray and CAT-scanning according to the discretion of the principal investigator.

Results

Patient details

Of the 24 patients who entered the trial, 14 were male and 10 female with ages ranging from 43 to 77 years (56.4 average). Histologically proven diagnoses were adenocarcinoma for 9 patients, large cell carcinoma for 9 patients and squamous cell carcinoma for 6 patients. The average survival time for 19 of the patients was 4 months after entering the trial which agreed with their prognosis without any therapy. Most of them developed metastases of their primaries.

Long term therapy

Because the serum metabolite concentrations showed considerable interpatient variation [Albrecht C. F., Kruger P. B., Smith B. J., Freestone M., Gouws L., Koch H., Miller R., and van Jaarsveld P. P. (supra)] due to apparent zero order formation of rooperol, adjustment of the maintenance dose, when necessary, was made for each patient during hospital visits in order to achieve combined metabolite blood levels near 100 µg/ml. According to in vitro experiments [Albrecht, C., Theron, E. and Kruger, P. (supra)] this concentration was considered adequate for activation of the metabolites to tumouricidal rooperol concentrations. The minimum and maximum maintenance doses required were 1200 and 3200 mg standardized plant extract per day divided into 3 equal doses every 8 hours. For most patients a daily dose of 2400 mg plant extract (4 capsules t.i.d.) was sufficient.

Clinical chemistry and haematology

FIGS. 44–46 provide summaries of the clinical chemistry and haematology data collected from the patients while they were on long term therapy. The vertical bars in the figures represent the standard deviation of the parameter measured during intervals of approximately 30 days.

Since 19 of the 24 patients survived less than one year and the data was collected also during their terminal phases, it is clear that the standard deviations at times less than 400 days on the trial will be larger than those who survived longer. This is especially true for the liver enzyme profile (FIG. 44) which is sensitive for metastases.

The dotted line in each of FIGS. 44–46 represents a regression line for all the data points while the shaded area depicts the normal limits for the population. For the liver enzymes the values stayed within normal limits for ALT, AST and LD while the regression line approached normal limits with time for ALP and GGT (FIG. 44).

FIG. 45 shows the trend observed with serum proteins. The relatively low albumin and increased acute phase protein concentrations (notably α-globulins) are clearly linked to the disease state of the patients. Serum electrolytes ($Na^+$, $K^+$, $Cl^-$, $Ca^{2+}$) and serum creatinine and urea concentrations were mostly within normal limits except for sporadic deviations during terminal phases.

FIG. 46 summarizes the haematological profile of the patients. These parameters are usually grossly affected by chemotherapeutic agents used in the treatment of cancer. It is clear that hypoxoside had no negative effect on these parameters. Haemoglobin stayed constant while the white cell count actually increased marginally which is reflected in a rise of the neutrophil count together with a small decrease in lymphocyte number. The number of platelets stayed remarkably constant.

The absence of any adverse effect of hypoxoside on the parameters reported above has been verified by specialists of the Departments of Chemical Pathology and Haematology of Tygerberg Hospital.

Other measurements

Regular measurements of blood pressure and temperature showed no abnormalities. Body mass also stayed constant except when patients developed cachexia in their terminal phases. Serial electrocardiograms also failed to demonstrate any evidence of cardiotoxicity of hypoxoside.

Side effects

One patient experienced possible drug intolerance of day 171 on the trial when the serum concentration of hypoxoside metabolites rose to 163 µg/ml. The episode presented with anxiety, nausea, vomiting, diarrhoea, dyspnoea and rigors and was associated with a doubling in the LD and ALP values. The patient stopped taking the drug and the symptoms subsided after 4–6 hours. The dose was then reduced from 2400 mg to 1200 mg per day and it was tolerated without further incidents for another 36 days when the patient died of cardiorespiratory failure.

Clinical status of longest living patients

The two patients who survived the longest while on hypoxoside underwent a full neurological examination together with their normal regular clinical examinations during the 30th month. No evidence of neurotoxicity resultant to hypoxoside ingestion was found.

The longest living patient died of TB pneumonia after 5 years on hypoxoside therapy (approximately 1 g per day). During this period initial lesions of his ribs reversed to a large extent, together with a reduction in original tumour mass and his alkaline phosphatase levels reduced from abnormal to normal. Histology of tissue taken at autopsy showed normality of all organs (kidney, liver, bone marrow, colon, intestine, brain, and spleen). The trial thus clearly demonstrates that both short and long term therapy (up to 5 years) with relatively high hypoxoside doses, does not result in any obvious toxic effect.

| | COMPOUND NOMENCLATURE |
|---|---|
| I | E-1,5-bis(3',4'-dihydroxyphenyl)-pent-4-en-1-yne |
| II | E-1,5-bis(4'-hydroxyphenyl)-pent-4-en-1-yne |
| III | E-1-(4'-hydroxyphenyl)-5-(3",4"-dihydroxyphenyl)-pent-4-en-1-yne |
| IV | E-1-(3',4'-dihydroxyphenyl)-5-(4"-hydroxyphenyl)-pent-4-en-1-yne |
| V | E-1,5-bis(3'-hydroxy-4'O-β-D-glucopyranosylphenyl)-pent-4-en-1-yne |
| VI | E-1,5-bis(4'-O-β-D-glucopyranosylphenyl)-pent-4-en-1-yne |
| VII | E-1-(4'-o-β-D-glucopyranosylphenyl)-5-(3"-hydroxy-4"-O-β-D-glucopyranosylphenyl)-pent-4-en-1-yne |
| VIII | E-1-(3'-hydroxy-4'-O-β-D-glucopyranosylphenyl)-5-(4"-O-β-D-glucopyranosylphenyl)-pent-4-en-1-yne |
| IX | E-1,5-bis(3'-hydroxy-4'-O-β-D-tetrasulfatoglucopyranosylphenyl)-pent-4-en-1-yne |
| X | E-1,5-bis(4'O-β-D-tetrasulfatoglucopyranosylphenyl)-pent-4-en-1-yne |
| XI | E-1-(4'-O-β-D-tetrasulfatoglucopyranosylphenyl)-5-(3"-hydroxy-4"-O-β-D-tetrasulfatoglucopyranosylphenyl)-pent-4-en-1-yne |
| XII | E-1-(3'-hydroxy-4'-O-β-D-tetrasulfatoglucopyranosylphenyl)-5-(4"-O-β-D-tetrasulfatoglucopyranosylphenyl)-pent-4-en-1-yne |
| XIII | E-1,5-bis(3'-hydroxy-4'-O-β-D-glucuronodylphenyl)-pent-4-en-1-yne |
| XIV | E-1,5-bis(4'-O-β-D-glucuronodylphenyl)-pent-4-en-1-yne |
| XV | E-1-(4'-O-β-D-glucuronodylphenyl)-5-(3"-hydroxy-4"-O-β-D-glucuronodylphenyl)-pent-4-en-1-yne |
| XVI | E-1-(3'-hydroxy-4'-O-β-D-glucuronodylphenyl)-5-(4"-O-β-D-glucuronodylphenyl)-pent-4-en-1-yne |
| XVII | E-1,5-bis(3'-hydroxy-4'-sulfatophenyl)-pent-4-en-1-yne |
| XVIII | E-1,5-bis(4'-sulfatophenyl)-pent-4-en-1-yne |
| XIX | E-1-(4'-sulfatophenyl)-5-(3"-hydroxy-4"-sulfatophenyl)-pent-4-en-1-yne |
| XX | E-1-(3'-hydroxy-4'-sulfatophenyl)-5-(4"-sulfatophenyl)-pent-4-en-1-yne |
| XXI | E-1-(3'-hydroxy-4'-sulfatophenyl)-5-(3"-hydroxy-4"-O-β-D-glucuronodylphenyl)-pent-4-en-1-yne |
| XXII | E-1-(4'-sulfatophenyl)-5-(4"-O-β-D-glucuronodylphenyl)-pent-4-en-1-yne |
| XXIII | E-1-(4'-sulfatophenyl)-5-(3"-hydroxy-4"-O-β-D-glucuronodylphenyl)-pent-4-en-1-yne |
| XXIV | E-1-(3'-hydroxy-4'-sulfatophenyl)-5-(4"-O-β-D-glucuronodylphenyl)-pent-4-en-1-yne |
| XXV | E-1-(3'-hydroxy-4'-O-β-D-glucuronodylphenyl)-5-(3"-hydroxy-4"-sulfatophenyl)-pent-4-en-1-yne |
| XXVI | E-1-(4'-O-β-D-glucuronodylphenyl)-5-(4"-sulfatophenyl)-pent-4-en-1-yne |
| XXVII | E-1-(4'-O-β-D-glucuronodylphenyl)-5-(3"-hydroxy-4-sulfatophenyl)-pent-4-en-1-yne |
| XXVIII | E-1-(3'-hydroxy-4-O-β-D-glucuronodylphenyl)-5-(4"-sulfatophenyl)-pent-4-en-1-yne |

We claim:

1. A method of reducing the rate of decrease in CD4 lymphocyte counts in a subject having a human immunodeficiency viral infection, which method comprises administering to the subject a medicament which comprises an active therapeutic agent comprising a dried methanolic extract from a plant species which is a member of the plant family Hypoxidaceae, the administering being over a period time and at a dosage rate which is effective for reducing the rate of decrease in CD4 lymphocyte counts in the subject.

2. A method as claimed in claim 1, in which the plant species is a member of a plant genus selected from the plant genera Hypoxis, Spiloxene, Curcuglio and Campynema.

3. A method as claimed in claim 2, in which the plant species is selected from the group consisting of *Hypoxis nitida, H. obtusa, H. rigidula, H. villosa, H. interjecta, H. multiceps, H. nyasica, H. rooperi, H. accuminata, H. latifolia, Spiloxene schlechteri* and hybrids thereof.

4. A method as claimed in claim 1, in which the administering is over a period of at least 90 days at a dosage rate of the dried methanolic extract of 50–1500 mg/day.

5. A method as claimed in claim 4, in which the administering is at a dosage rate of 100–1000 mg/day.

6. A method as claimed in claim 4, in which the administering is by way of oral administration, the extract being administered at least twice daily at regular time intervals.

7. A method as claimed in claim 6, in which the extract is administered to the subject in a dosage form selected from tablets, powders, liquids and capsules containing the extract, said tablets, powders and capsules each containing 20–1000 mg of the extract and said liquids each containing 4–200 mg/ml of the extract.

8. A method as claimed in claim 1, in which the administering is selected from parenteral administration and oral administration.

9. A method as claimed in claim 8, in which the administering is by way of parenteral administration, the subject receiving an intravenous administration of the extract dissolved in sterile saline solution in which the total concentration of extract is 2–200 mg/ml.

10. A method as claimed in claim 9, in which said concentration is 40–60 mg/ml.

11. A method as claimed in claim 1, in which the active therapeutic agent further comprises a compound according to the general formula (1)

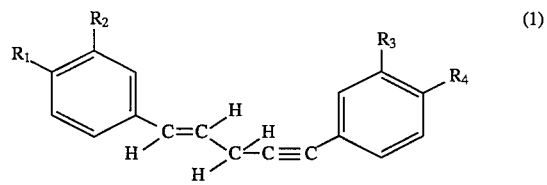

in which: $R_1, R_2, R_3$ and $R_4$ are the same or different and are selected from —H, —OH, A, B, C and D in which:

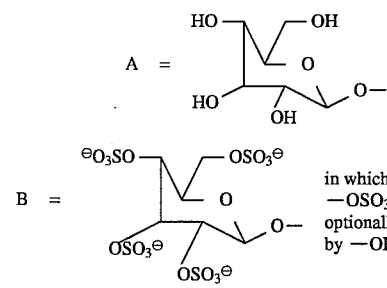

in which any 1-3 of the —OSO$_3^\ominus$ groups is optionally substituted by —OH -continued

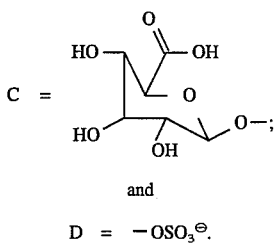

and $$D = -OSO_3^{\ominus}.$$

12. A method as claimed in claim 1 wherein the medicament includes a physiologically acceptable carrier.

13. A method of treating a human immunodeficiency viral infection in a subject in need of such treatment, which method comprises administering to the subject a medicament which comprises an active therapeutic agent comprising a dried methanolic extract from a plant species which is a member of the plant family Hypoxidaceae, the administering being over a period of time and at a dosage rate which is effective for treating the human immunodeficiency viral infection in the subject.

14. A method as claimed in claim 13, in which the plant species is a member of a plant genus selected from the plant genera Hypoxis, Spiloxene, Curcuglio and Campynema.

15. A method as claimed in claim 14, in which the plant species is selected from the group consisting of *Hypoxis nitida, H. obtusa, H. rigidula, H. villosa, H. interjecta, H. multeceps, H. nyasica, H. roopere, H. accuminata, H. latifolia, Spiloxene schlechteri* and hybrids thereof.

16. A method as claimed in claim 13, in which the administering is over a period of at least 90 days at a dosage rate of a dried methanolic extract of 50–1500 mg/day.

17. A method as claimed in claim 16, in which the administering is at a dosage rate of 100–1000 mg/day.

18. A method as claimed in claim 16, in which administering is by way of oral administration, the extract being administered at least twice daily at regular time intervals.

19. A method as claimed in claim 18, in which the extract is administered to the subject in a dosage form selected from tablets, powders, liquids and capsules containing the extract said tablets, powders and capsules each containing 20–1000 mg of the extract and said liquids each containing 4–200 mg/ml of extract.

20. A method as claimed in claim 13, in which the administering is selected from parenteral administration and oral administration.

21. A method as claimed in claim 20, in which the administering is by way of parenteral administration, the subject receiving an intravenous administration of the extract dissolved in sterile saline solution in which the concentration of dried methanolic extract is 2–200 mg/ml.

22. A method as claimed in claim 21, in which said concentration is 50–100 mg/ml.

23. A method as claimed in claim 13, in which the active therapeutic agent further comprises a compound according to the general formula (1)

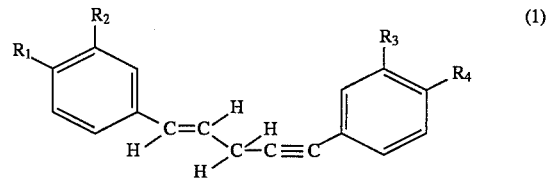

in which: $R_1, R_2, R_3$ and $R_4$ are the same or different and are selected from —H, —OH, A, B, C and D in which:

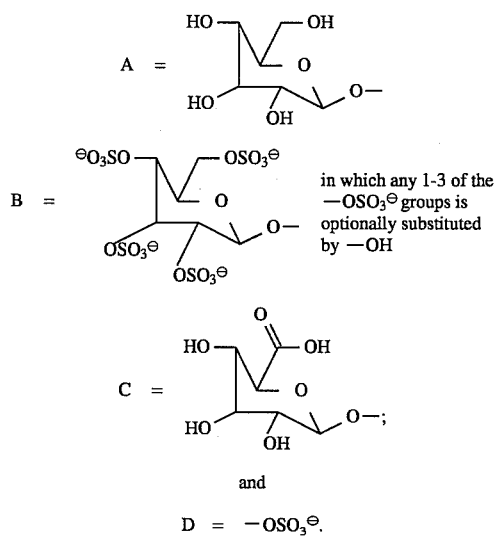

and $$D = -OSO_3^{\ominus}.$$

24. A method as claimed in claim 13, wherein the medicament includes a physiological acceptable carrier.

25. A method of reducing the rate of decrease in CD4 lymphocyte counts in a subject in need of such reduction, which method comprises administering to the subject a medicament which comprises an active therapeutic agent comprising a dried methanolic extract from a plant species which is a member of the plant family Hypoxidacea, the administering being over a period of time and at a dosage rate which is effective for reducing the rate of decrease in CD4 lymphocyte counts in the subject.

* * * * *